US009249131B2

(12) United States Patent
Hadida Ruah et al.

(10) Patent No.: US 9,249,131 B2
(45) Date of Patent: *Feb. 2, 2016

(54) MODULATORS OF ATP-BINDING CASSETTE TRANSPORTERS

(71) Applicant: Vertex Pharmaceuticals Incorporated, Boston, MA (US)

(72) Inventors: Sara S. Hadida Ruah, La Jolla, CA (US); Mark T. Miller, San Diego, CA (US); Ashvani K. Singh, San Diego, CA (US); Thomas Cleveland, San Diego, CA (US); Lewis R. Makings, Encinitas, CA (US); Matthew Hamilton, Missouri City, TX (US); Peter D. J. Grootenhuis, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/506,856

(22) Filed: Oct. 6, 2014

(65) Prior Publication Data

US 2015/0025076 A1 Jan. 22, 2015

Related U.S. Application Data

(60) Continuation of application No. 14/079,664, filed on Nov. 14, 2013, now Pat. No. 8,853,415, which is a division of application No. 13/848,970, filed on Mar. 22, 2013, now Pat. No. 8,741,939, which is a division of application No. 13/174,844, filed on Jul. 1, 2011, now Pat. No. 8,431,605, which is a division of application No. 10/936,448, filed on Sep. 7, 2004, now Pat. No. 7,973,169.

(60) Provisional application No. 60/500,444, filed on Sep. 6, 2003.

(51) Int. Cl.
*C07D 277/46* (2006.01)
*C07D 417/06* (2006.01)
*C07D 263/48* (2006.01)
*C07D 277/82* (2006.01)
*C07D 417/04* (2006.01)
*C07D 417/12* (2006.01)
*C07D 295/15* (2006.01)
*G01N 33/50* (2006.01)

(52) U.S. Cl.
CPC ............ *C07D 417/06* (2013.01); *C07D 263/48* (2013.01); *C07D 277/46* (2013.01); *C07D 277/82* (2013.01); *C07D 295/15* (2013.01); *C07D 417/04* (2013.01); *C07D 417/12* (2013.01); *G01N 33/5076* (2013.01)

(58) Field of Classification Search
CPC .................................................. C07D 277/46
See application file for complete search history.

(56) References Cited

U.S. PATENT DOCUMENTS

| | | | |
|---|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Hadida-Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Hadida-Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Hadida-Ruah et al. |
| 8,299,099 B2 | 10/2012 | Hadida-Ruah et al. |
| 8,314,239 B2 | 11/2012 | Binch et al. |
| 8,314,256 B2 | 11/2012 | Hadida-Ruah et al. |
| 8,318,733 B2 | 11/2012 | Hadida-Ruah et al. |
| 8,324,207 B2 | 12/2012 | Hadida-Ruah et al. |
| 8,324,242 B2 | 12/2012 | Hadida-Ruah et al. |
| 8,344,147 B2 | 1/2013 | Ambhaikar et al. |
| 8,354,427 B2 | 1/2013 | Van Goor et al. |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |

(Continued)

OTHER PUBLICATIONS

Jung et al. (Bioorganic & Medicinal Chemistry (2004), 12(3), 613-623).*

(Continued)

*Primary Examiner* — Robert Havlin
(74) *Attorney, Agent, or Firm* — Michael J. DiVerdi

(57) ABSTRACT

The present invention relates to modulator of ATP-Binding Cassette ("ABC") transporters or fragments thereof, including CF Transmembrane Regulator ("CFTR"), compositions thereof, and methods therewith. The present invention also relates to methods of treating ABC transporter mediated diseases using such modulators.

17 Claims, No Drawings

(56) References Cited

U.S. PATENT DOCUMENTS

| | | |
|---|---|---|
| 8,415,387 B2 | 4/2013 | Hadida Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel et al. |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Hadida-Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Hadida Ruah et al. |
| 8,524,910 B2 | 9/2013 | Hadida-Ruah et al. |
| 8,541,453 B2 | 9/2013 | Hadida Ruah et al. |
| 8,552,006 B2 | 10/2013 | Binch et al. |
| 8,552,034 B2 | 10/2013 | Verwijs et al. |
| 8,563,573 B2 | 10/2013 | Hadida-Ruah et al. |
| 8,563,593 B2 | 10/2013 | Alargova et al. |
| 8,575,209 B2 | 11/2013 | Hadida Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Hadida Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Hadida-Ruah et al. |
| 8,629,162 B2 | 1/2014 | Hadida Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young et al. |
| 8,722,704 B2 | 5/2014 | Hadida Ruah et al. |
| 8,741,922 B2 | 6/2014 | Zhang et al. |
| 8,741,925 B2 | 6/2014 | Hadida Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida-Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Hadida Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 2005/0113423 A1 | 5/2005 | VanGoor et al. |
| 2008/0306062 A1 | 12/2008 | Hadida-Ruah et al. |
| 2009/0105272 A1 | 4/2009 | Grootenhuis |
| 2009/0176839 A1 | 7/2009 | Keshavarz-Shokri et al. |
| 2009/0246820 A1 | 10/2009 | Singh et al. |
| 2010/0036130 A1 | 2/2010 | Siesel et al. |
| 2010/0074949 A1 | 3/2010 | Rowe et al. |
| 2010/0125090 A1 | 5/2010 | Hadida-Ruah et al. |
| 2010/0144798 A1 | 6/2010 | VanGoor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Van Goor et al. |
| 2011/0288122 A1 | 11/2011 | Van Goor et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0116238 A1 | 5/2013 | Looker et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0178471 A1 | 7/2013 | Hadida Ruah et al. |
| 2013/0184276 A1 | 7/2013 | Hadida Ruah et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0237569 A1 | 9/2013 | Hadida-Ruah et al. |
| 2013/0245010 A1 | 9/2013 | Hadida-Ruah et al. |
| 2013/0245011 A1 | 9/2013 | Hadida-Ruah et al. |
| 2013/0303484 A1 | 11/2013 | Grootenhuis et al. |
| 2013/0317020 A1 | 11/2013 | Hadida Ruah et al. |
| 2013/0324743 A1 | 12/2013 | Belmont et al. |
| 2013/0331567 A1 | 12/2013 | Hadida-Ruah et al. |
| 2014/0023706 A1 | 1/2014 | Verwijs et al. |
| 2014/0024672 A1 | 1/2014 | Hadida-Ruah et al. |
| 2014/0057906 A1 | 2/2014 | Hadida-Ruah et al. |
| 2014/0072995 A1 | 3/2014 | Hadida-Ruah et al. |
| 2014/0073653 A1 | 3/2014 | Binch et al. |
| 2014/0080825 A1 | 3/2014 | Hadida-Ruah et al. |
| 2014/0080826 A1 | 3/2014 | Hadida Ruah et al. |
| 2014/0088141 A1 | 3/2014 | Binch et al. |
| 2014/0088160 A1 | 3/2014 | Alargova et al. |
| 2014/0094499 A1 | 4/2014 | Alargova et al. |
| 2014/0112988 A1 | 4/2014 | Rowe et al. |
| 2014/0121208 A1 | 5/2014 | Van Goor |
| 2014/0121379 A1 | 5/2014 | Siesel et al. |
| 2014/0121381 A1 | 5/2014 | Hadida-Ruah et al. |
| 2014/0142138 A1 | 5/2014 | Van Goor et al. |
| 2014/0142312 A1 | 5/2014 | Luisi et al. |
| 2014/0155431 A1 | 6/2014 | Hadida Ruah et al. |
| 2014/0155626 A1 | 6/2014 | Hadida-Ruah et al. |
| 2014/0163011 A1 | 6/2014 | Hadida Ruah et al. |
| 2014/0163068 A1 | 6/2014 | Verwijs et al. |
| 2014/0187787 A1 | 7/2014 | Ambhaikar et al. |
| 2014/0206689 A1 | 7/2014 | Hadida Ruah et al. |
| 2014/0206720 A1 | 7/2014 | Young et al. |
| 2014/0221424 A1 | 8/2014 | Zha et al. |
| 2014/0221430 A1 | 8/2014 | Keshavarz-Shokri et al. |
| 2014/0235625 A1 | 8/2014 | Binch et al. |
| 2014/0235668 A1 | 8/2014 | Binch et al. |
| 2014/0242172 A1 | 8/2014 | Hurter et al. |
| 2014/0243289 A1 | 8/2014 | Grootenhuis et al. |
| 2014/0255483 A1 | 9/2014 | Dokou et al. |
| 2014/0256770 A1 | 9/2014 | DeMattei et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0080431 A1 | 3/2015 | Van Goor et al. |
| 2015/0203478 A1 | 7/2015 | Keshavarz-Shokri et al. |
| 2015/0218122 A1 | 8/2015 | Tanoury |

OTHER PUBLICATIONS

Database Chemcats, CAS, XP002316953, Accession No. 2000:928510 (publication date: Apr. 25, 2003).*

* cited by examiner

MODULATORS OF ATP-BINDING CASSETTE TRANSPORTERS

CROSS-REFERENCE TO RELATED APPLICATIONS

The present application is a continuation of U.S. patent application Ser. No. 14/079,664, filed Nov. 14, 2013, which is a divisional of U.S. Pat. No. 8,741,939, filed Mar. 22, 2013, which is a divisional of U.S. Pat. No. 8,431,605, filed Jul. 1, 2011, which is a divisional of U.S. Pat. No. 7,973,169, filed Sep. 7, 2004, which claims priority to U. S. Provisional patent application No. 60/500,444, filed Sep. 6, 2003, the entire contents of all applications being incorporated herein by reference.

TECHNICAL FIELD OF THE INVENTION

The present invention relates to modulators of ATP-Binding Cassette ("ABC") transporters or fragments thereof, including CF Transmembrane Regulator ("CFTR"), compositions thereof, and methods therewith. The present invention also relates to methods of treating ABC transporter mediated diseases using such modulators.

BACKGROUND OF THE INVENTION

ABC transporters are a group of membrane transporter proteins that play a major role in the transport and protection of cells against a wide variety of pharmacological agents, potentially toxic drugs, and xenobiotics. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. Up until the present time, 48 Human ABC Transporters have been identified, and these have been arranged into 7 families based on their sequence identity and function.

ABC transporters play a variety of important physiological roles within the body, as well as providing a defense against harmful compounds from the environment. Moreover they represent important potential drug targets both in their own right, as well as, because in many cases therapeutic drugs are also transported out of the target cell by these molecules.

One of the members of the ABC transporter family, namely, CFTR, is believed be the chloride channel responsible for cAMP-mediated chloride secretion in epithelial cells, and to play a key role in the secretion of chloride and maintenance of normal electrolyte transport throughout the body. CFTR is a protein of approximately 1480 amino acids made up of two repeated elements, each comprising six transmembrane segments and a nucleotide-binding domain. The two repeats are separated by a large, polar, regulatory (R)-domain containing multiple potential phosphorylation sites.

The gene associated with CFTR has been identified and sequenced (See Gregory, R. J. et al, (1990) Nature 347:382-386; Rich, D. P. et al. (1990) Nature 347:358-362), (Riordan, J. R. et al. (1989) Science 245:1066-1073). A defect in this gene leads to cystic fibrosis (hereinafter "CF"), the most common fatal genetic disease in humans affecting approximately one in every 2,500 infants born in the United States. Within the general United States population, up to 10 million people carry a single copy of the defective gene without apparent ill effects. In contrast, individuals with two copies of the CF associated gene suffer from the chronic effects of CF, including chronic lung destruction and death.

In patients with Cystic fibrosis, expression of the CF associated gene in airway cells, leads to reduced cellular apical chloride conductance causing an imbalance in ion and fluid transport. It is widely believed that this leads to the abnormal mucus secretion in pancreatic ductules and in the airways that ultimately results in the pulmonary infections and epithelial cell damage typically associated with disease progression in CF. In addition to respiratory problems, CF patients typically suffer from gastrointestinal problems, and pancreatic insufficiency. Males are almost uniformly infertile and fertility is decreased in females. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). At present, more than 1000 mutations in the CF gene have been identified (http://www.genet.sickkids.on.ca/cftr/), but population studies have indicated that the most common CF mutation, a deletion of the 3 nucleotides that encode phenylalanine at position 508 of the CFTR amino acid sequence, is associated with approximately 70% of the cases of cystic fibrosis. The mutated CFTR protein is referred to as ΔF508.

It is believed that the deletion of residue 508 in ΔF508-CFTR prevents the nascent protein from folding correctly, resulting in the inability of this mutant protein to exit the endoplasmic reticulum (hereinafter "ER"), and traffic to the plasma membrane. As a result, insufficient amounts of the mature protein are present at the plasma membrane and chloride transport within epithelial tissues is significantly reduced (Quinton, P. M. (1990), FASEB J. 4: 2709-2727). Hence, the cellular phenomenon of defective ER processing of other protein/s like CFTR, by the ER machinery, has been shown to be the underlying basis for a wide range of isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5 (7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. Studies have shown, however, that ΔF508-CFTR, when presented at the plasma membrane is functional as a cAMP-responsive Cl⁻ channel (Dalemans et al., (1991), Nature Lond. 354: 526-528; Denning at al., supra.; Pasyk and Foskett (1995), J. Cell. Biochem. 270: 12347-50).

Although CFTR transports a variety of molecules in addition to anions, it is clear that this role (the transport of anions) represents one element in an important mechanism of transporting ions and water across the epithelium. The other elements include the epithelial Na⁺ channel, ENaC, Na⁺/2Cl⁻/K⁺ co-transporter, Na⁺—K⁺-ATPase pump and the basolateral membrane K⁺ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na$^+$—K$^+$-ATPase pump and Cl— channels expressed on the basolateral surface of the cell. Secondary active transport of chloride from the luminal side leads to the accumulation of intracellular chloride, which can then passively leave the cell via Cl$^-$ channels, resulting in a vectorial transport. Arrangement of Na$^+$/2Cl$^-$/K$^+$ co-transporter, Na$^+$—K$^+$-ATPase pump and the basolateral membrane K$^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to CF, modulation of CFTR activity may be beneficial for other diseases not directly caused by mutations in CFTR, such as secretory diseases and other protein folding diseases mediated by CFTR. These include, but are not limited to, chronic obstructive pulmonary disease (hereinafter "COPD"), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimised periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in. the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5 (7), pp 745-751 (1999); Shastry, B. S., et al., Neurochem. International, 43, pp 1-7 (2003); Rutishauser, J., et al., Swiss Med Wkly, 132, pp. 211-222 (2002); Morello, J P et al., TIPS, 21, pp. 466-469 2000); Bross P., et al., Human Mut., 14, pp. 186-198 (1999)].

The diseases associated with the first class of ER malfunction are CF (due to in is folded ΔF508-CFTR), hereditary emphysema (due to α1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia. Type 1 chylomicronemia, abetalipoproteinemia, lysosomal storage diseases, such as I-cell disease/pseudo-Hurler, mucopolysaccharidoses (due to lysosomal processing enzymes) Sandhof/Tay-Sachs (due to β-hexosaminidase), Crigler-Najjar type II (due to UDF-glucuronyl-sialyc-transferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, Hereditary emphysema (due to α1-Antitrypsin (PiZ variant), Congenital hyperthyroidism, osteogenesis imperfecta (due to Type I, II, IV procollagen), hereditary hypofibrinogenemia (due to fibrinogen), ACT deficiency (due to α1-Antichymotrypsin), Diabetes insipidus (DI), neurophyseal DI (due to Vasopressin hormone/V2-receptor), neprogenic DI (due to aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebellar ataxia type I, spinal and bulbar muscular atrophy, dentatorubal pallidoluysian, and myotonic dystrophy, as well as Spongiform encephalopathies, such as hereditary Creutzfeldt-Jakob disease (due to Prion protein processing defect), Fabry disease (due to lysosomal α-galactosidase A) and Straussler-Scheinker syndrome (due to Prp processing defect).

In CP, chloride transport mediated by the CFTR is reduced resulting in the abnormal mucus secretion that characterizes the disease. By contrast in secretory diarrheas epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, death and impaired growth.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotavirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

There is a need for correctors that enhance the density of CFTR in the plasma membrane by facilitating the migration of the CFTR thereto.

SUMMARY OF THE INVENTION

The present invention provides a method of modulating ABC transporter activity, comprising the step of contacting said ABC transporter with a compound of formula I or formula I':

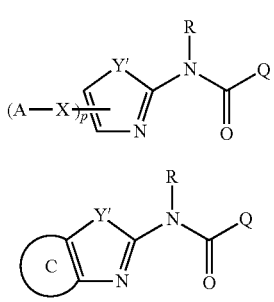

or a pharmaceutically acceptable salt thereof;
wherein:
Y' is O, S, or NR;
p is 0-2;
X is a bond, O, S, S(O), S(O)$_2$, CF$_2$, CH$_2$, —CHOR—, —C(O)—, —O—C(O)—, —C(O)—O, —C(O)—NR, —NR—C(O)—, —NR—C(O)—O—, —O—C(O)—NR—, —NR—C(O)—NR—, or NR;
R is H, R$^2$, or R$^6$;
A is aliphatic, aryl, heteroaryl, heterocyclic, or cycloalkyl;
C is a phenyl or 5-8 membered cycloaliphatic ring;

Q is selected from:

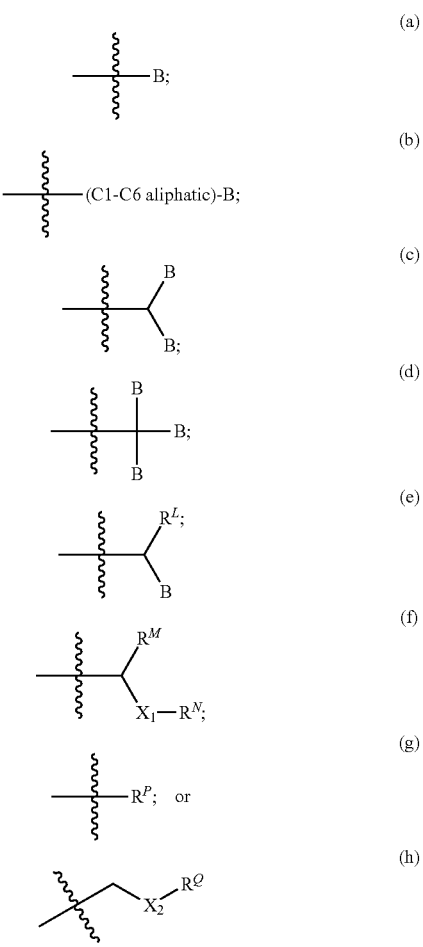

each B is independently selected from 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;

wherein each A, B, and C is independently and optionally substituted with up to 4 substituents independently selected from R$^1$, R$^2$, R$^3$, R$^4$, or R$^5$;

R$^L$ is —OR$^A$, —SR$^A$, or —N(R$^{AB}$)$_2$;

each R$^A$ is independently hydrogen, C1-C6 aliphatic, or a 3-7 membered carbocyclic or heterocyclic ring, saturated or unsaturated ring, having up to 3 heteroatoms selected from O, N, or S, wherein each R$^A$ is optionally substituted with up to 3 substituents independently selected from R$^1$, R$^4$ or R$^7$, each R$^{AB}$ is independently hydrogen, or C1-C6 aliphatic optionally substituted with up to 3 substituents independently selected from R$^1$, R$^4$ or R$^7$.

wherein up to two methylene units in R$^A$ or R$^{AB}$ are optionally replaced with —CO—, —CS—, —COCO—, —CONR—, —CO$_2$—, —OCO—, —NRCO$_2$—, —O—, —NRCONR—, —OCONR—, —NRCO—, —S—, 13 SO, —SO$_2$—, —NR—, —SO$_2$NR—, NRSO$_2$—, or —NRSO$_2$NR; or two R$^{AB}$, taken together with the nitrogen atom, is a 3-7 membered heterocyclic or heteroaryl ring containing up to 4 heteroatoms selected from O, N, or S, wherein said ring is optionally substituted with up to 2 substituents selected from oxo or $(C_{1-4}\text{aliphatic})_p$-Y;

$R^M$ is C1-C6 aliphatic, optionally substituted with up to two substituents selected from $R^1$, $R^2$, $R^3$, or $R^4$;

each of $X_1$ and $X_2$ is independently selected from O, S, or NR;

$R^N$ is C1-C6 aliphatic or phenyl, wherein $R^N$ is optionally substituted with up to two substituents selected from $R^1$, $R^2$, $R^3$, or $R^4$;

$R^P$ is C1-C6 aliphatic, optionally substituted with up to two substituents selected from $R^1$, $R^2$, $R^3$, or $R^4$;

$R^Q$ is C1-C6 aliphatic or aryl, wherein $R^Q$ is optionally substituted with up to two substituents selected from $R^1$, $R^2$, $R^3$, or $R^4$;

$R^1$ is oxo, $R^6$ or $((C1\text{-}C4)\text{aliphatic})_n$-Y;

n is 0 or 1;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)^2$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ optionally comprises up to 2 substituents independently selected from $R^1$, $R^4$, or $R^5$;

$R^3$ is a cycloaliphatic, aryl, heterocyclic, or heteroaryl ring optionally comprising up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^5C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^6SO_2SR^5R^6$, $NR^6SO_2N(R^5)_2$, $NR^5SO_2N(R^6)_2$, $NR^5S_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each $R^7$ optionally comprises up to 2 substituents independently chosen from H, $(C_1\text{-}C_6)$-straight or branched alkyl, $(C_2\text{-}C_6)$ straight or branched alkenyl or alkynyl, 1,2-methylenedioxy, 1,2-ethylenedioxy, or $(CH_2)_n$-Z;

Z is selected from halo, CN, $NO_2$, $CF_3$, $OCF_3$, OH, S-aliphatic, S(O)-aliphatic, $SO_2$-aliphatic, $NH_2$, NH-aliphatic, $N(\text{aliphatic})_2$, $N(\text{aliphatic})R^8$, $NHR^8$, $N(R^8)_2$, COOH, C(O)O(-aliphatic), or O-aliphatic; and $R^8$ is an amino-capping group.

The present invention also provides compositions comprising compounds of formula (I) and formula (I'), and methods of treating ABC transporter mediated diseases using compounds of formula (I) and formula (I').

DETAILED DESCRIPTION OF THE INVENTION

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111 (3), 477-90.

The term "CFTR" as used herein means cystic fibrosis transmembrane regulator or a mutation thereof capable of its regulator activity, in part or full, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

The phrase "optionally substituted" is used interchangeably with the phrase "substituted or unsubstituted."

The term "aliphatic" or "aliphatic group", as used herein, means a straight-chain or branched, hydrocarbon chain that is completely saturated (alkyl) or is unsaturated (alkenyl or alkynyl). Unless otherwise specified, an aliphatic group has 1 to 12 carbon atoms, preferably, 1-6 carbon atoms, and more preferably, 1-4carbon atoms. Up to three, and preferably two, —$CH_2$— in said aliphatic may be replaced with O, S, or —NR.

The term "alkylidene" as used herein means a straight-chain or branched hydrocarbon chain that is completely saturated or unsaturated, and is connected to the rest of the molecule through covalent bonds. Exemplary alkylidene groups include methylene, ethylene, or propylene. Unless otherwise specified, an alkylidene group has 1 to 12 carbon atoms, preferably, 1-6 carbon atoms, and more preferably, 1-4 carbon atoms.

The term "cycloaliphatic" means a saturated or partially unsaturated monocyclic or bicyclic hydrocarbon ring that has up to two points of attachment to the rest of the molecule. Unless otherwise specified, preferred cycloaliphatic rings are 3-8 membered monocyclic rings, more preferably 3-6, and even more preferably, 3, 5, or 6. Also preferred, unless otherwise specified, are 8-12 membered bicyclic hydrocarbon rings, more preferably 10 membered bicyclic hydrocarbon rings.

The term "heteroatom," unless otherwise specified, means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or as in N-substituted, pyrrolidinyl, The term "unsaturated", as used herein, means a double bond or a triple bond. Each such bond constitutes one unit of unsaturation.

The term "aryl" used alone or as part of a larger moiety as in "aralkyl", "aralkoxy", or "aryloxyalkyl", refers to monocyclic, bicyclic and tricyclic aromatic carbocyclic ring systems. Unless otherwise specified, preferred aryl rings have a total of five to fourteen ring members, wherein at least one ring, if bicyclic or tricyclic, in the system is aromatic and wherein each ring in the system contains up to 6 ring members. The term "aryl" may be used interchangeably with the term "aryl ring". Phenyl is an example of aryl.

The term "heterocycle", "heterocyclyl", or "heterocyclic" as used herein means non-aromatic, monocyclic, bicyclic or tricyclic ring systems wherein one or more ring members is a heteroatom. Unless otherwise specified, each ring in the system preferably contains contains 3 to 7 ring members with preferably 1-3 heteroatoms.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, and at least one ring in the system contains one or more heteroatoms. Unless otherwise specified, such ring systems preferably have a total of 5 to 15 ring members, wherein each ring in the system preferably contains 3 to 7 ring members, with preferably 1-3 heteroatoms. The term "heteroaryl" may be used interchangeably with the term "heteroaryl ring" or the term "heteroaromatic".

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

The present invention provides a method of modulating ABC transporter activity, comprising the step of contacting said ABC transporter with a compound of formula I or formula I':

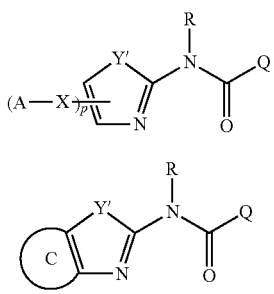

or a pharmaceutically acceptable salt thereof;
wherein:
Y' is O, S, or NR;
p is 0-2;
X is a bond, O, S, S(O), S(O)$_2$, CF$_2$, CH$_2$, —CHOR—, —C(O)—, —O—C(O)—, —C(O)-O, —C(O)—NR, —NR—C(O)—, —NR—C(O)—O—, —O—C(O)— NR—, —NR—C(O)—NR—, or NR;
R is H, R$^2$, or R$^6$;
A is aliphatic, aryl, heteroaryl, heterocyclic, or cycloalkyl;
C is a phenyl or 5-8 membered cycloaliphatic ring;
Q is selected from:

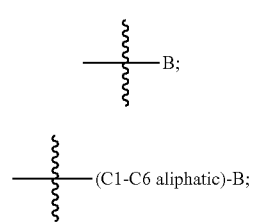

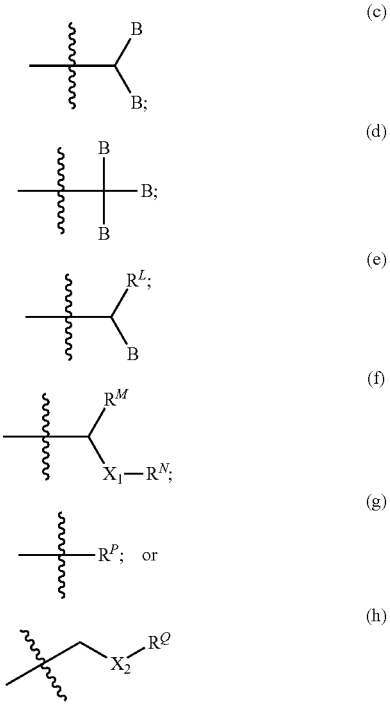

each B is independently selected from 3-7 membered monocyclic or 8-14 metered bicyclic or tricyclic, saturated, unsaturated or aromatic ring containing 0-4 heteroatoms in each ring, wherein each said heteroatom is independently selected from, N, NH, S, or O;
wherein each A, B, and C is independently and optionally substituted with op to 4 substituents independently selected from R$^1$, R$^2$, R$^3$, R$^4$, or R$^5$;
R$^L$ is —OR$^A$, —SR$^A$, or —N(R$^{AB}$)$_2$;
each R$^A$ is independently hydrogen, C1-C6 aliphatic, or a 3-7 membered carbocyclic or heterocyclic ring, saturated or unsaturated ring, having up to 3 heteroatoms selected from O, N, or S, wherein each R$^A$ is optionally substituted with up to 3 substituents independently selected from R$^1$, R$^4$ or R$^7$,
each R$^{AB}$ is independently hydrogen or C1-C6 aliphatic optionally substituted with up to 3 substituents independently selected from R$^1$, R$^4$ or R$^7$;
wherein up to two methylene units in R$^A$ or R$^{AB}$ are optionally replaced with —CO—, —CS—, —COCO—, —CONR—, —CO$_2$—, —OCO—, —NRCO$_2$—, —O—, —NRCONR—, —OCONR—, —NRCO—, —S—, —SO, —SO$_2$—, —NR—, —SO$_2$NR—, NRSO$_2$—, or —NRSO$_2$NR; or
two R$^{AB}$, taken together with the nitrogen atom, is a 3-7 membered heterocyclic or heteroaryl ring containing up to 4 heteroatoms selected from O, N, or S, wherein said ring is optionally substituted with up to 2 substituents selected from oxo or (C$_{1-4}$aliphatic)$_p$-Y;
R$^M$ is C1-C6 aliphatic, optionally substituted with up to two substituents selected from R$^1$, R$^2$, R$^3$, or R$^4$;
each of X$_1$ and X$_2$ is independently selected from O, S, or NR;
R$^N$ is C1-C6 aliphatic or phenyl, wherein R$^N$ is optionally substituted with up to two substituents selected from R$^1$, R$^2$, R$^3$, or R$^4$;

$R^P$ is C1-C6 aliphatic, optionally substituted with up to two substituents selected from $R^1$, $R^2$, $R^3$, or $R^4$;

$R^Q$ is C1-C6 aliphatic or aryl, wherein $R^Q$ is optionally substituted with up to two substituents selected from $R^1$, $R^2$, $R^3$, or $R^4$;

$R^1$ is oxo, $R^6$ or ((C1-C4)aliphatic)$_n$-Y;

n is 0 or 1;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)_2$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ optionally comprises up to 2 substituents independently selected from $R^1$, $R^4$, or $R^5$;

$R^3$ is a cycloaliphatic, aryl, heterocyclic, or heteroaryl ring optionally comprising up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each $R^7$ optionally comprises up to 2 substituents independently chosen from H, ($C_1$-$C_6$)-straight or branched alkyl, ($C_2$-$C_6$) straight or branched alkenyl or alkynyl, 1,2-methylenedioxy, 1,2-ethylenedioxy, or $(CH_2)_n$-Z;

Z is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, N(aliphatic)$R^8$, $NHR^8$, $N(R^8)_2$, COOH, C(O)O(-aliphatic, or O-aliphatic; and $R^8$ is an amino-capping group.

The term "amino capping group" refers to a suitable chemical group that may be attached to a nitrogen atom. The term "capping" refers to when the designated amino group is attached to a suitable chemical group (e.g., protecting group). Examples of suitable amino capping groups are described in T. W. Greene et al., *Protective Groups in Organic Synthesis*, 3d, Ed., John Wiley and Sons (1999); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

According to a preferred embodiment, Y' is S.

According to one embodiment, Y' is O.

According to another embodiment, Y' is NR. In one embodiment, R is H. Or, R is $R^2$. Or, R is $R^6$.

According to another embodiment, p is 1. Or, p is 1 and X is attached to the carbon adjacent to Y' atom. Or, p is 1 and X is attached to the carbon adjacent to the ring nitrogen atom.

According to another embodiment, p is 2.

According to another embodiment, X is a bond, O, S, $CH_2$, $CF_2$, CHOR, C(O)NR, C(O)O—, NRC(O), or NR. In certain embodiments, X is a bond, O, or $CH_2$. In other embodiments, X is $CH_2$.

According to another embodiment, A is an optionally substituted C3-C7 cycloaliphatic ring. Preferably, A is an optionally substituted cyclopropyl, cyclopentyl, or cyclohexyl.

According to another embodiment, A is optionally substituted (C1-C10)aliphatic. In certain embodiments, A is optionally substituted methyl, ethyl, propyl, butyl, pentyl, or hexyl.

According to another embodiment, A is optionally substituted C6-C10 aryl ring. In one embodiment, A is optionally substituted phenyl or naphthyl.

According to another embodiment, A is optionally substituted C5-C12 heteroaryl ring. In certain embodiments, A is selected from optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, acridinyl, phenazinyl, phenothiazinyl, or phenoxazinyl.

According to another embodiment, A is optionally substituted C3-C12 heterocyclic ring. In certain embodiments, A is selected from optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

In some embodiments, A, X, and the ring attached thereto, taken together, is selected from:

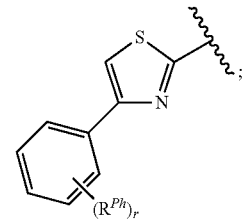

i

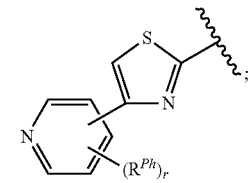

ii

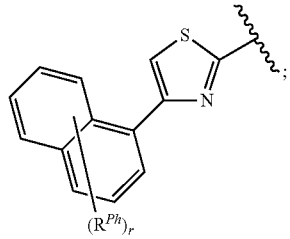

iii

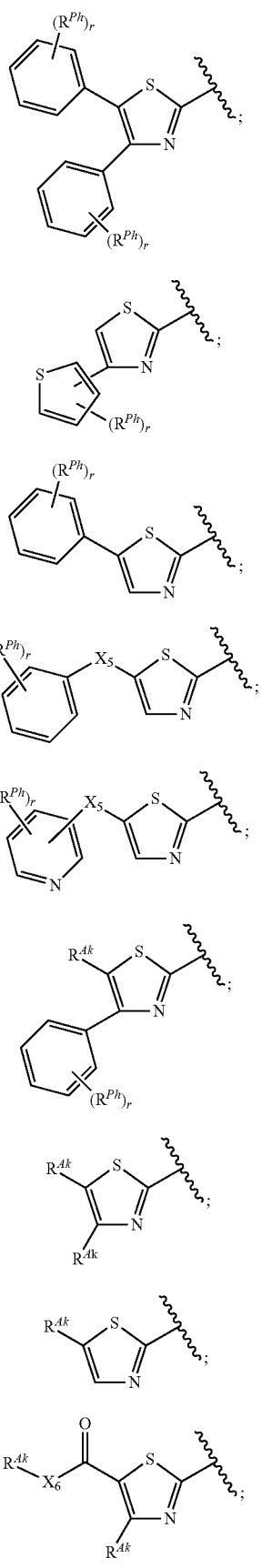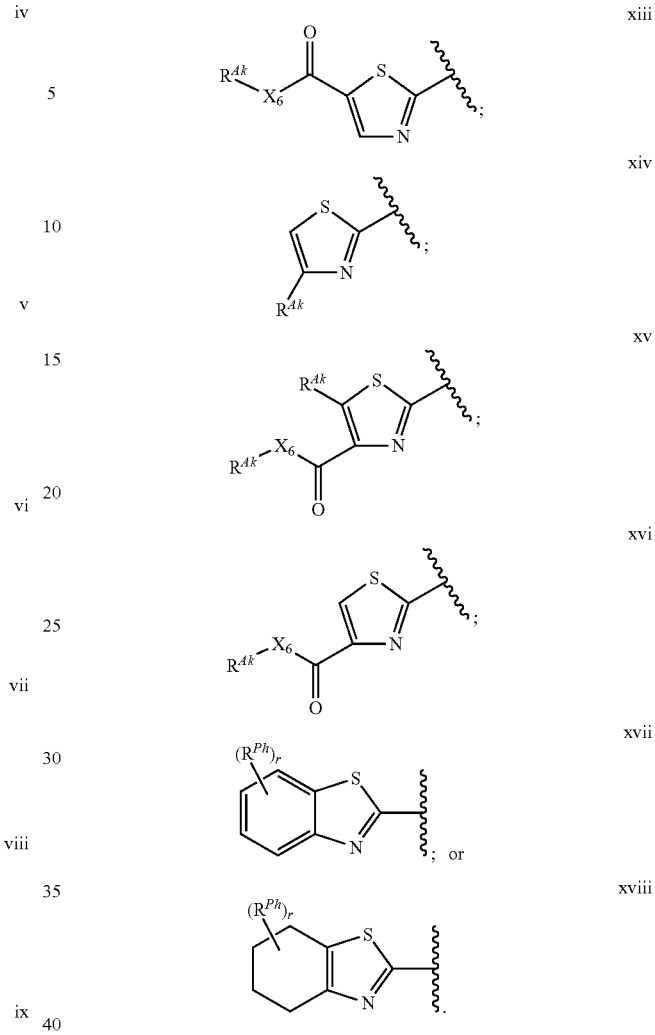

wherein:
$R^{Ph}$ is independently $R^1$, $R^2$, or $R^3$; and
r is 0-3.
$X_5$ is $CH_2$, C(O), or CHOR;
$X_6$ is O or $NR^2$; and
$R^{Ak}$ is C1-C6 aliphatic, optionally substituted with $R^1$, $R^2$, or $R^3$.

In another embodiment, A, X, and the ring attached thereto, taken together, is selected from any of the rings i to xviii, wherein the sulfur atom in each of the thiazole ring is replaced with an oxygen atom (to provide the corresponding oxazole).

According to another embodiment, each B is independently selected from optionally substituted C6-C10 aryl. In certain embodiments, each B is an optionally substituted phenyl or naphthyl. Or, each B is an unsubstituted phenyl.

According to another embodiment, each B is independently selected from optionally substituted C5-C12 heteroaryl. In certain embodiments, each B is independently an optionally substituted C5-C7 heteroaryl.

According to another embodiment, each B is independently selected from triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, carbazolyl, acridinyl, phenazinyl, phenothiazinyl, phenoxazinyl, indenyl, naphthyl, azulinyl, or anthracenyl.

According to another embodiment, $R^1$ is 1,2-methylene dioxy, or 1,2-ethylenedioxy.

According to another embodiment, $R^1$ is $R^6$, wherein $R^6$ is straight chain or branched (C1-C6)alkyl or (C2-C6) alkenyl or alkynyl, optionally substituted with $R^7$.

According to another embodiment, $R^1$ is (C1-C4 aliphatic)$_n$-Y, wherein n is 0 or 1, and Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;

According to another embodiment, $R^1$ is selected from halo, $CF_3$, $NH_2$, NH(C1-C4 alkyl), $NHC(O)CH_3$, OH, O(C1-C4 alkyl), OPh, O-benzyl, S—(C1-C4 alkyl), C1-C4 aliphatic, CN, methylenedioxy, ethylenedixoy, $SO_2NH$(C1-C4 alkyl), or $SO_2N$(C1-C4 alkyl)$_2$.

According to another embodiment, $R^1$ is selected from methyl, n-propyl, i-propyl, t-butyl, halo, $CF_3$, $NH_2$, $NH(CH_3)$, $NHC(O)CH_3$, OH, $OCH_3$, OPh, O-benzyl, S—$(C_2H_5)$, S—$CH_3$, $NO_2$, CN, methylenedioxy, $SO_2NH$(n-propyl), or $SO_2N$(n-propyl)$_2$.

According to one embodiment, $R^2$ is a straight chain or branched (C1-C6)alkyl or (C2-C6) alkenyl or alkynyl, optionally substituted with $R^1$, $R^4$, or $R^5$. In certain embodiments, $R^2$ is a straight chain or branched (C1-C4)alkyl or (C2-C4) alkenyl or alkynyl, optionally substituted with $R^1$, $R^4$, or $R^5$.

According to another embodiment, $R^3$ is optionally substituted phenyl, napthyl, C5-C10 heteroaryl or C3-C7 heterocyclyl. In certain embodiments, $R^3$ is an optionally substituted phenyl, C5-C6 heteroaryl, or C3-C6 heterocyclyl.

According to one embodiment, $R^4$ is selected from $OR^5$, $OR^6$, $SR^5$, $SR^6$, $NR^5COR^5$, $NR^5COR^6$, $NR^6COR^5$, or $NR^6COR^6$.

According to one embodiment, $R^5$ is C5-C6 cycloalkyl, C6 or C10 aryl, C5-C10 heteroaryl or C3-C7 heterocyclyl, optionally substituted with up to 2 $R^1$. In certain embodiments, $R^5$ is an optionally substituted cyclohexyl, phenyl, C5-C6 heteroaryl, or C3-C6 heterocyclyl.

According to one embodiment, $R^6$ is H.

According to another embodiment, $R^6$ is a straight chain or branched (C1-C6)alkyl or (C2-C6 alkenyl) or alkynyl, optionally substituted with $R^7$.

According to another embodiment, $R^6$ is a straight chain or branched (C1-C6)alkyl or (C2-C6 alkenyl) or alkynyl.

According to one embodiment, $R^7$ is C5-C6 cycloalkyl, phenyl, naphthyl, C5-C10 heteroaryl or C3-C7 heterocyclyl, optionally substituted with straight chain or branched (C1-C6)alkyl or (C2-C6 alkenyl) or alkynyl. Or, $R^7$ is C5-C6 cycloalkyl, phenyl, naphthyl, C5-C10 heteroaryl or C3-C7 heterocyclyl, optionally substituted with 1-2-methylenedioxy, 1,2-ethylenedioxy, or $(CH_2)_n$—Z. In certain embodiments, $R^7$ is an optionally substituted cyclohexyl, phenyl, C5-C6 heteroaryl, or C3-C6 heterocyclyl.

According to a preferred embodiment, $R^8$ is acetyl, arylsulfonyl or alkylsulfonyl.

In another embodiment, Q in compounds of formula I is selected from:

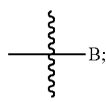

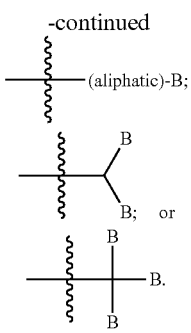

In one embodiment, the present invention provides compounds having formula I-a:

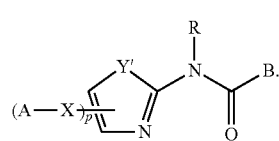

I-a

In certain embodiments, p is 1. Or, p is 2.

In certain embodiments, X is a bond, O, $CH_2$, CHOH, C(O), or C(O)O. Or, X is a bond, O, or $CH_2$.

In certain embodiments, p is 1 and X is a bond. In one embodiment, p is 1, and X-A is attached to the carbon adjacent to the ring nitrogen atom. Or, p is 1, and X-A is attached to the carbon adjacent to the Y'.

In certain embodiments, p is 1, X is $CH_2$, CHOH, or C(O), and A is an optionally substituted phenyl.

In certain -embodiments, X is a bond, and A is an optionally substituted phenyl.

In certain embodiments, p is 2, each X is a bond, and each A is an optionally substituted phenyl.

In certain embodiments, each B is independently and optionally substituted ring selected from:

i

ii

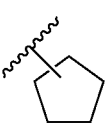

iii

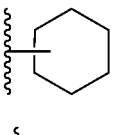

iv

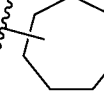

v

-continued

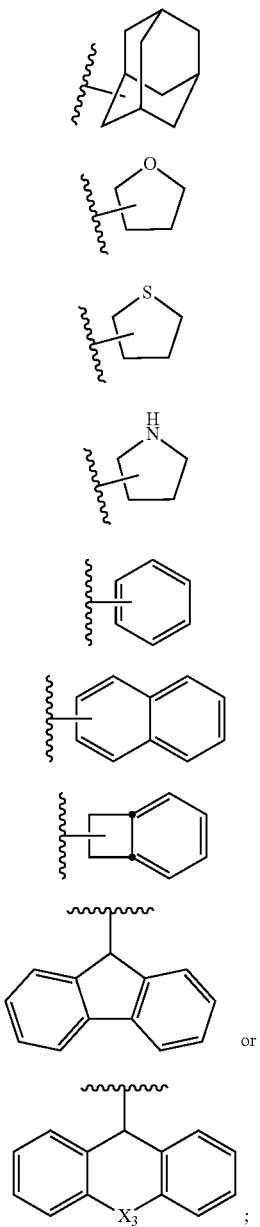

wherein X₃ is O, S, or NR.

Preferred substituents on B include C1-C4 alkyl, —O—C1-C4, alkyl, CN, halo, COOH, —C(O)NH₂, —C(O)O(C1-C4 alkyl), —C(O)NH(C1-C4 alkyl), —C(O)N(C1-C4 alkyl)₂, or phenyl optionally substituted with up to two substituents selected from C1-C4 alkyl, —O-C1-C4 alkyl, CN, halo, COOH, —C(O)NH₂, —C(O)O(C1-C4 alkyl), —C(O)NH(C1-C4 alkyl), —C(O)N(C1-C4 alkyl)₂.

In certain embodiments, each B is independently an optionally substituted ring selected from ring i, iii, iv, v, or vi. Or, wherein B is an optionally substituted ring vii.

In some embodiments, B is independently ring x optionally substituted with up to two substituents selected from R¹ or phenyl optionally substituted with up to two R¹. Preferably, B is phenyl optionally substituted with up to two substituents selected from C1-C4 alkyl, —O-C1-C4 alkyl, CN, halo, COOH, —C(O)NH₂, —C(O)O(C1-C4 alkyl), —C(O)NH(C1-C4 alkyl), —C(O)N(C1-C4 alkyl)₂, or phenyl optionally substituted with up to two substituents selected from C1-C4 alkyl, —O-C1-C4 alkyl, CN, halo, COOH, —C(O)NH₂, —C(O)O(C1-C4 alkyl), —C(O)NH(C1-C4 alkyl), —C(O)N(C1-C4 alkyl)₂.

Or, each B is an optionally substituted ring selected from ring xi, xii, xiii, or xiv.

In certain embodiments, p is 1. Or, p is 2.

In some embodiments, R is hydrogen.

In some embodiments, Y' is S. Or, Y' is O.

In certain embodiments, X is a bond and A is optionally substituted phenyl. In certain embodiments, A is attached to the carbon atom adjacent to the nitrogen ring atom.

In certain embodiments, A is phenyl optionally substituted with up to two substituents selected from C1-C4 alkyl, C1-C4 alkoxy, cyano, halo, N-pyrrolidinyl, N-piperidinyl, or methylenedioxy.

In certain embodiments, A is phenyl, methoxyphenyl, dimethoxyphenyl, cyanophenyl, N-pyrrolidinylphenyl, methylenedioxyphenyl, halophenyl, methylphenyl, or dimethylphenyl.

In certain embodiments, A is phenyl, 3-methoxyphenyl, 2-methoxyphenyl, 4-chlorophenyl, 4-cyanophenyl, 4-(N-pyrrolidinyl)phenyl, 4-tolyl, 3,4-methylenedioxyphenyl, 3-chlorophenyl, 2,4-dimethoxyphenyl, 2-chlorophenyl, 4-bromophenyl, or 2,4-dimethylphenyl.

In certain other embodiments, A is C3-C10 cycloaliphatic ring. Exemplary ring include cyclopropyl, cyclopentyl, cyclohexyl, cycloheptyl, or adamantyl. In certain embodiments, A is cyclohexyl or adamantyl.

In certain embodiments the compounds of the present invention have one of more of the following features:
a) R is hydrogen;
b) Y' is S;
c) A is phenyl optionally substituted with up to two substituents selected from C1-C4 alkyl, C1-C4 alkoxy, cyano, halo, N-pyrrolidinyl, N-piperidinyl, or methylenedioxy; and
d) B is phenyl optionally substituted with up to two substituents selected from C1-C4 alkyl, —O-C1-C4 alkyl, CN, halo, COOH, —C(O)NH₂, —C(O)O(C1-C4 alkyl), —C(O)NH(C1-C4 alkyl), —C(O)N(C1-C4 alkyl)₂, or phenyl optionally substituted with up to two substituents selected from C1-C4 alkyl, —O-C1-C4 alkyl, CN, halo, COOH, —C(O)NH₂, —C(O)O(C1-C4 alkyl), —C(O)NH(C1-C4 alkyl), —C(O)N(C1-C4 alkyl)₂.

In one embodiment, the present invention provides compounds having formula I-b:

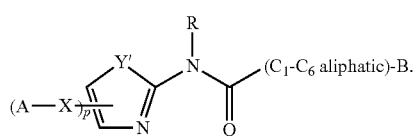

I-b

In certain embodiments, p is 1 and X is a bond. In one embodiment, p is 1, and X-A is attached to the carbon adjacent to the ring nitrogen atom. Or, p is 1, and X-A is attached to the cartoon adjacent to the Y'.

In certain embodiments, p is 1, X is CH₂, CHOH, or C(O), preferably CH₂, and A is an optionally substituted phenyl.

In certain embodiments, X is a bond, and A is an optionally substituted phenyl.

In certain embodiments, p is 2, each X is a bond, and each A is an optionally substituted phenyl.

In certain embodiments, said C1-C6 aliphatic is C1-C4 straight or branched alkylidene. Exemplary alkyl include —CH$_2$—, —CH(Me)-, —C(Me)$_2$-, —CH(Et)-, —C(Et)$_2$-, or —CH$_2$—CH(Me)-.

In certain embodiments, B is selected from optionally substituted C3-C8 cycloalkyl, phenyl, piperidyl, or pyrrolidinyl. Preferably, B is phenyl, cyclopentyl, cyclohexyl, or piperidyl, optionally substituted with up to two $R^1$ substituents.

In some embodiments, said (C1-C6 aliphatic)-B in formula I-b is selected from:

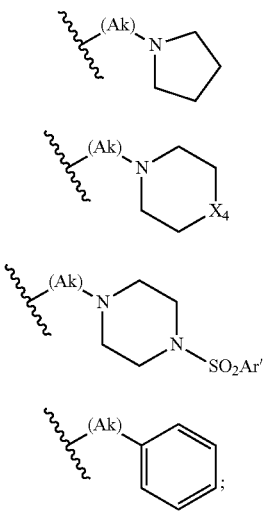

wherein:
Ak is C1-C6 straight or branched alkylidene;
$X_4$ is CH$_2$, O or S;
Ar' is phenyl optionally substituted with up to two $R^1$; and
B is optionally substituted with up to two $R^1$.

In some embodiments, Ak is selected from CH$_2$, CH(CH$_3$), C(CH$_3$)$_2$, CH(Et), C(Et)$_2$, CH(n-propyl), CH(i-Pr), CH(n-butyl), CH(but-2-yl), or CH(t-butyl).

In some embodiments, Ar' is phenyl optionally substituted with halo, C1-C4 alkyl, or O—(C1-C4 alkyl).

In some embodiments, $X_4$ is S. Or, $X_4$ is O.

In some embodiments, R is hydrogen.

In one embodiment, the present invention provides compounds of formula I-f:

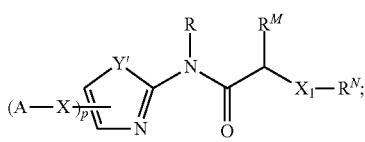

wherein:
Y' is O or S;
$X_1$ is O, S, or NR;
$R^M$ is C1-C6 aliphatic or phenyl, wherein $R^M$ is optionally substituted with up to two substituents independently selected from $R^1$, $R^2$, $R^3$;
$R^N$ is C1-C6 aliphatic or a 3-7 membered monocyclic, saturated, unsaturated or aromatic ring containing 0-4 heteroatoms in each ring, wherein each said heteroatom is independently selected from N, NH, S, or O;

wherein $R^N$ is optionally substituted with up to 4 substituents independently selected from $R^1$, $R^2$, $R^3$, $R^4$, or $R^5$.

In certain embodiments, p is 1 and X is a bond. In one embodiment, p is 1, and X-A is attached to the carbon adjacent to the ring nitrogen atom. Or, p is 1, and X-A is attached to the carbon adjacent to the Y'.

In certain embodiments, p is 1, X is CH$_2$, CHOH, or C(O), preferably CH$_2$, and A is an optionally substituted phenyl.

In certain embodiments, X is a bond, and A is an optionally substituted phenyl.

In certain embodiments, p is 2, each X is a bond, and each A is an optionally substituted phenyl.

In some embodiments, $X_1$ is NH or N(C1-C4 alkyl). Or, $X_1$ is O.

In some embodiments, $R^M$ is optionally substituted phenyl.

In some embodiments, $R^M$ is C1-C6 alkyl, optionally substituted with phenyl. In some embodiments, $R^M$ is C1-C4 alkyl.

In some embodiments, $R^N$ is optionally substituted C3-C7 cycloaliphatic, phenyl, or benzyl.

In some embodiments, $R^N$ is C1-C6 aliphatic.

In some embodiments, R is hydrogen.

In one embodiment, the present invention provides a compound of formula I-g:

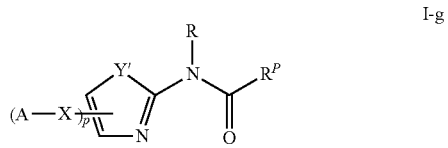

wherein:
Y' is O or S;
$R^P$ is C1-C8 aliphatic optionally substituted with up to two substituents independently selected from $R^1$, $R^2$, or $R^3$.

In certain embodiments, p is 1 and X is a bond. In one embodiment, p is 1, and X-A is attached to the carbon adjacent to the ring nitrogen atom. Or, p is 1, and X-A is attached to the carbon, adjacent to the Y'.

In certain embodiments, p is 1, X is CH$_2$, CHOH, or C(O), preferably CH$_2$, and A is an optionally substituted phenyl.

In certain embodiments, X is a bond, and A is an optionally substituted phenyl.

In certain embodiments, p is 2, each X is a bond, and each A is an optionally substituted phenyl.

In some embodiments, $R^P$ is C1-C4 alkyl, optionally substituted with up to two $R^1$.

In some embodiments, $R^P$ is selected from ethyl, n-propyl, i-propyl, n-butyl, but-2-yl, or t-butyl, isoamyl, optionally substituted with halo, CN, COOH, or CONH$_2$.

In some embodiments, R is hydrogen.

In certain embodiments, p is 1. Or, p is 2.

In certain embodiments, p is 2, and each A is optionally substituted phenyl. Or, p is 2, and each A is phenyl.

In certain embodiments, compounds of formula 1-g have one or more of the following features:
a) Y' is S;
b) R is hydrogen;
c) p is 2 and each A is phenyl;
d) $R^P$ is isoamyl, t-butyl, ethyl, isopropyl, n-propyl, 1-carboxy-prop-3-yl, or 1-carboxy-2-methyl-prop-3-yl.

In one embodiment, the present, invention provides compounds or formula I-h:

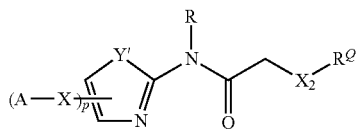

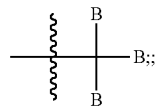

wherein:
Y' is O or S;
X$_2$ is O, B, or NR;
R$^Q$ is C1-C6 aliphatic or phenyl, optionally substituted with up to two substituents independently selected from R$^1$, R$^2$, or R$^3$.

In certain embodiments, p is 1 and X is a bond. In one embodiment, p is 1, and X-A is attached to the carbon adjacent to the ring nitrogen atom. Or, p is 1, and X-A is attached to the carbon adjacent to the Y'.

In certain, embodiments, p is 1, X is CH$_2$, CHOH, or C(O), preferably CH$_2$, and A is an optionally substituted phenyl.

In certain embodiments, X is a bond, and A is an optionally substituted phenyl.

In certain embodiments, p is 2, each X is a bond, and each A is an optionally substituted phenyl.

In some embodiments, X$_2$ is S. Or, X$_2$ is O.

In some embodiments, R$^Q$ is C1-C4 alkyl, optionally substituted with up to three R$^1$.

In some embodiments, R$^Q$ is phenyl optionally substituted with C1-C4 alkyl, or R$^1$.

According to another preferred embodiment, the methods of the present invention employ a compound having formula (IA):

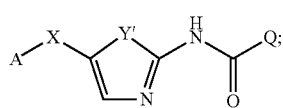

wherein:
Y' is O, S, or NR;
X is a bond, CH$_2$, CHOR, C(O)O, C(O), NR, or O;
A is aliphatic, aryl, heteroaryl, heterocyclic, or cycloaliphatic;
Q is selected from:

(a)

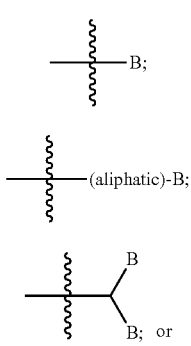

(b)

(c)

(d)

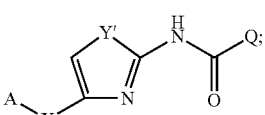

each B is independently selected from 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;

R is H, R$^2$, or R$^6$;

wherein each A and B is independently and optionally substituted with up to 4 substituents independently selected from R$^1$, R$^2$, R$^3$, R$^4$, or R$^5$; and R$^1$, R$^2$, R$^3$, R$^4$, or R$^5$ are as defined above for formula (I).

According to one embodiment of formula (IA), Y' is S.

According to another embodiment of formula (IA), Y' is O.

According to another embodiment of formula (IA), Y' is NR.

In one embodiment, X is a bond, CH$_2$, NR, or O;

According to another embodiment of formula (IA), X is CH$_2$. According to another embodiment of formula (IA), X is CF$_2$. According to yet another embodiment of formula (IA), X is a bond. According to yet another embodiment of formula (IA), X is O. According to yet another embodiment of formula (IA), X is NR.

According to another embodiment of formula (IA), A is phenyl or a 5-6 membered heteroaryl, preferably phenyl, wherein A is optionally substituted with up to 3 substituents selected from R$^1$, R$^2$, R$^3$, or R$^4$.

According to one embodiment of formula (IA), Q is B. Alternatively, Q is —(C1-C6)-aliphatic-B. Or, Q is CH(B)$_2$. According to another embodiment, Q is C(B)$_3$. Preferably, B is phenyl.

In one embodiment, X is a bond, —CHOR—, or —C(O)—.

Exemplary compounds of formula (IA) are those wherein:
(i) X is a bond, CH$_2$, or O;
(i) A is optionally substituted phenyl;
(iii) Q is diphenylmethyl.

Exemplary compounds of formula (IA) useful in the methods of the present invention are as shown below in Table 1.

According to another embodiment, the methods of the present invention employ a compound having formula (IB):

(IB)

wherein:
Y' is O, S, or NR;
X is a bond, CH$_2$, CHOR, C(O), C(O)O, NR, or O;
A is aliphatic, aryl, heteroaryl, heterocyclic, or cycloaliphatic;

Q is selected from:

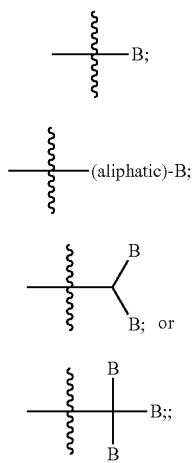

each B is independently selected from 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;

R is H, $R^2$, or $R^6$;

wherein each A and B is independently and optionally substituted with up to 4 substituents independently selected from $R^1$, $R^2$, $R^3$, $R^4$, or $R^5$; and $R^1$, $R^2$, $R^3$, $R^4$, or $R^5$ are as defined above for formula (I).

According to one embodiment of formula (IB), Y' is S.

According to another embodiment of formula (IB), Y' is O.

According to another embodiment of formula (IB), Y' is NR.

According to one embodiment of formula (IB), X is a bond, $CH_2$, NR, or O. Or, X is a bond or $CH_2$. According to another embodiment of formula (IB), X is $CF_2$. According to yet another embodiment of formula (IB), X is a bond. According to yet another embodiment of formula (IB), X is O. According to yet another embodiment of formula (IB), X is NR.

According to another embodiment of formula (IB), A is phenyl or a 5-6 membered heteroaryl, preferably phenyl, wherein A is optionally substituted with up to 3 substituents selected from $R^1$, $R^2$, $R^3$, or $R^4$.

According to another embodiment of formula (IB), Q is B. Alternatively, Q is —(C1-C6)-aliphatic-B. Or, Q is $CH(B)_2$. According to another embodiment, Q is $C(B)_3$. Preferably, B is phenyl.

Preferred compounds of formula IB are those wherein:
(i) X is a bond, $CH_2$, or O;
(ii) A is optionally substituted phenyl;
(iii) Q is diphenylmethyl.

According to another embodiment, the methods of the present invention employ a compound having formula (IC):

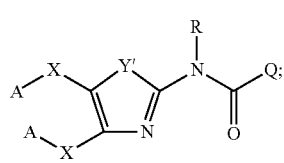

(IC)

wherein:
Y' is O, S, or NR;
each X is independently a bond, $CH_2$, —CHOR—, —C(O))—, —C(O)—, NR, or O;
A is aliphatic, aryl, heteroaryl, heterocyclic, or cycloaliphatic;
Q is selected from:

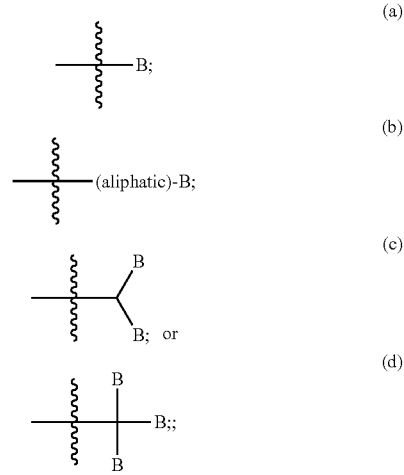

each B is independently selected from 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;

R is H, $R^2$, or $R^6$;

wherein each A and B is independently and optionally substituted with up to 4 substituents independently selected from $R^1$, $R^2$, $R^3$, $R^4$, or $R^5$; and $R^1$, $R^2$, $R^3$, $R^4$, or $R^5$ are as defined above for formula (I).

According to one embodiment of formula (IC), Y' is S.

According to another embodiment of formula (IC), Y' is O.

According to another embodiment of formula (IC), Y' is NR.

According to another embodiment of formula (IC), X is a bond or $CH_2$. According to another embodiment of formula (IC), X is $CH_2$. According to yet another embodiment of formula (IC), X is a bond. Or, X is —CHOR—. Or, X is —C(O)—. According to yet another embodiment of formula (IC), X is O. According to yet another embodiment of formula (IC), X is NR.

According to another embodiment of formula (IC), A is phenyl or a 5-6 membered heteroaryl, preferably phenyl, wherein A is optionally substituted with up to 3 substituents selected from $R^1$, $R^2$, $R^3$, or $R^4$.

According to another embodiment of formula (IC), Q is B. Alternatively, Q is —(C1-C6)-aliphatic-B. Or, Q is $CH(B)_2$. According to another embodiment, Q is $C(B)_3$. Preferably, B is phenyl.

Exemplary compounds of formula (IC) are those wherein:
(i) each X is a bond, —CHOR—, or —C(O)—;
(ii) each A is optionally substituted phenyl, (C1-C6)aliphatic, or $CF_3$;
(iii) Q is optionally substituted phenyl, (C1-C6)aliphatic, or diphenylmethyl.

According to another embodiment, the present invention provides a compound having formula (II):

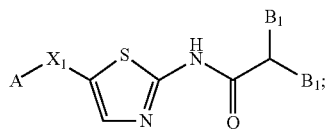

(II)

or a pharmaceutically acceptable salt thereof;
wherein:
$X_1$ is a bond, O, S, CHOR, C(O), C(O)O, $CF_2$, $CH_2$, or NR;
R is H or $R^2$
$A_1$ is (C2-C10) aliphatic, aryl, heteroaryl, heterocyclic, or cycloaliphatic;
each $B_1$ is independently selected from 3-7 membered monocyclic, saturated, unsaturated or aromatic ring containing 0-4 heteroatoms selected from N, NH, S, or O;
wherein each $A_1$ is optionally substituted with up to 4 substituents independently selected from $R^1, R^2, R^3, R^4$, or $R^5$;
$R^1$ is oxo, $R^6$ or $((C1-C4)aliphatic)_n$-Y;
n is 0 or 1;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)_2$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ optionally comprises up to 2 substituents independently selected from $R^1$, $R^4$, or $R^5$;
$R^3$ is a cycloaliphatic, aryl, heterocyclic, or heteroaryl ring optionally comprising up to 3 substituents, independently selected from $R^1, R^2, R^4$ or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;
$R^5$ is a cycloaliphatic, aryl, heterocyclic, or heteroaryl ring, optionally comprising up to 3 $R^1$ substituents;
$R^6$ is H or aliphatic, wherein $R^6$ optionally comprises a $R^7$ substituent;
$R^7$ is a cycloaliphatic, aryl, heterocyclic, or heteroaryl ring, and each $R^7$ optionally comprises up to 2 substituents independently chosen from H, $(C_1-C_6)$-straight or branched alkyl, $(C_2-C_6)$ straight or branched alkenyl or alkynyl, 1,2-methylenedioxy, 1,2-ethylenedioxy, or $(CH_2)_n$-Z;
Z is selected from halo, CN, $NO_2$, $CF_3$, $OCF_3$, OH, S-aliphatic, S(O)-aliphatic, $SO_2$-aliphatic, $NH_2$, NH-aliphatic, $N(aliphatic)_2$, $N(aliphatic)R^8$, $NHR^8$, $N(R^8)_2$, COOH, C(O)O(-aliphatic, or O-aliphatic; and
$R^8$ is an amino capping group.

provided that:
(i) when both $B_1$ are simultaneously phenyl and $X_1$ is $CH_2$, then A is not 4-fluoro-phenyl, 4-phenyl-piperidyl, phenyl, 2,4-dichloro-phenyl, 4-methoxy-phenyl, 3,4-dichloro-phenyl, 2,5-dichloro-phenyl, 4-nitro-phenyl, 4-bromo-phenyl, 4-methyl-phenyl, 2-chloro-phenyl, 1-naphthyl, 3-trifluoromethyl-phenyl, 2,3-dichlorophenyl, N-morpholinyl, 4-chloro-phenyl, 3-chloro-phenyl, or 3-nitro-phenyl;
(ii) when $X_1$ is a bond or $CH_2$, one $B_1$ is a substituted phenyl and the other $B_1$ is cycloaliphatic, then $A_1$ is not (C2-C8) aliphatic; and
(iii) when $X_1$ is a bond, then $A_1$ is not an optionally substituted 6-membered heteroaryl ring with 1-3 nitrogen ring atoms.

According to one embodiment of formula (II), $X_1$ is a bond, O, S, $CF_2$, $CH_2$, or NR. $X_1$ is $CH_2$, $CF_2$, or O. Or $X_1$ is $CH_2$ or O. In certain embodiments, $X_1$ is $CH_2$.

According to another embodiment, $A_1$ is an optionally substituted C3-C7 cycloaliphatic ring. In certain embodiments, $A_1$ is an optionally substituted cyclopropyl, cyclopentyl, or cyclohexyl.

According to another embodiment, $A_1$ is optionally substituted (C1-C10)aliphatic. In certain embodiments, $A_1$ is optionally substituted methyl, ethyl, propyl, butyl, pentyl, or hexyl.

According to another embodiment, $A_1$ is optionally substituted C6-C10 aryl ring. In certain embodiments, $A_1$ is optionally substituted phenyl or naphthyl.

According to another embodiment, $A_1$ is optionally substituted C5-C12 heteroaryl ring. In certain embodiments, A is selected from optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, acridinyl, phenazinyl, phenothiazinyl, or phenoxazinyl.

According to another embodiment, $A_1$ is optionally substituted C3-C12 heterocyclic ring. In certain embodiments, $A_1$ is selected from optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

According to another embodiment of formula (II), each $B_1$ is independently selected from optionally substituted C6-C10 aryl. In certain embodiments, each $B_1$ is independently an optionally substituted phenyl or naphthyl. Or, each $B_1$ is an unsubstituted phenyl.

According to another embodiment, each $B_1$ is independently selected from optionally substituted C5-C12 heteroaryl ring. In certain embodiments, each $B_1$ is independently and optionally substituted C5-C7 heteroaryl ring. Or, each $B_1$ is independently selected from optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, carbazolyl, carbazolyl, acridinyl, phenazinyl, phenothiazinyl, phenoxazinyl, indenyl, naphthyl, azulinyl, or anthracenyl.

According to another embodiment, each $B_1$ is independently an optionally substituted 3-12 membered heterocyclic ring having up to 4 heteroatoms selected from O, S, or NR. In certain embodiments, each $B_1$ is independently selected from optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

Embodiments of $R^1$, $R^2$, $R^3$, $R^4$, $R^5$, $R^6$, $R^7$, $R^8$, and Z in compound of formula (II) are as described above for compound of formula (I).

In certain embodiments, one $B_1$ is phenyl with up to two $R^1$ substituents, and the other $B_1$ is selected from pyrazolyl, pyrrolidinyl, piperidinyl, morpholinyl, thiomorpholinyl, or piperazinyl, optionally substituted with up to two $R^1$ substituents.

In certain embodiments, one $B_1$ is phenyl, and the other $B_1$ is selected from 1,2-pyrazol-1-yl, 1-piperidinyl, 2-carboethoxy-1-piperidinyl 4-morpholinyl, 3-carboethoxy-1-piperidinyl, 3-methyl-1-piperidinyl, 2-methyl-1-pyrrolidinyl, 3-hydroxymethyl-1-piperidinyl, 4-carboethoxy-1-piperidinyl, 4-methyl-1-piperidinyl, 1-pyrrolidinyl, 4-(pyrimidin-2-yl)-1piperazinyl, or 4-hydroxy-piperidinyl.

According to another embodiment, the present invention provides a compound of formula IIA:

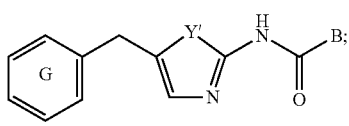

IIA wherein:
Y' is O or S;
B is a 3-8 membered, saturated, moncyclic, ring having 0-4 heteroatoms selected from O, S, or N; and
ring G and B are optionally substituted with up to four substituents independently selected from $R^1$, $R^2$, $R^3$, $R^4$, or $R^5$;
provided that when Y' is S, and:
a) when B is cyclohexyl, tetrahydrofuran-2-yl, or cyclopropyl, and ring G has 1-3 halo substituents, then ring G has at least one additional substituent other than halo; and
b) when B is tetrahydrofuran-2-yl, then ring G is not phenyl, trifluoromethylphenyl, methoxyphenyl, or tolyl;
c) when B is cyclohexyl, then ring G is not phenyl or trifluoromethylphenyl.

According to one embodiment, B is tetrahydrofuranyl, piperidyl, morpholinyl, or thiomorpholinyl.

According to another embodiment, B is C3-C8 saturated, carbocyclic, monocyclic ring. Exemplary rings include cyclopropyl, cyclopentyl, cyclohexyl, or cycloheptyl.

According to another embodiment, ring G is phenyl optionally substituted with $R^1$. Preferably, ring G is optionally substituted with up to two substituents selected from halo, cyano, C1-C4 alkyl, or O—(C1-C4 alkyl).

In one embodiment, compounds of formula IIA have one or more of the following features:
a) Y' is S;
b) ring G is halo-substituted phenyl;
c) B is phenyl optionally substituted with halo, cyano, C1-C4 alkyl, or O—(C1-C4 alkyl).

According to another embodiment, the present invention provides a compound of formula IIB:

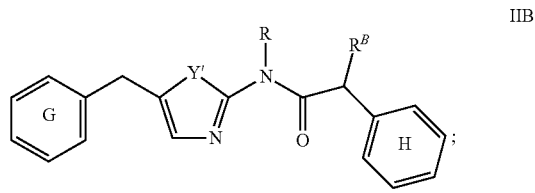

IIB wherein:
Y' is S or O;
R is H, $R^2$, or $R^6$;
$R^B$ is C1-C6 aliphatic or a 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O; wherein each of ring G, ring H, and $R^B$ is independently and optionally substituted with up to 4 substituents selected from $R^1$, $R^2$, $R^3$, $R^4$, or $R^5$; provided that when Y is S, and:
a) when $R^B$ is hydrogen, and ring G and ring H both have 1-3 halo substituents, then at least one of ring G and ring H has an additional substituent other than halo;
b) when $R^B$ is hydrogen and ring H is unsubstituted phenyl, then ring G is not phenyl or phenyl substituted with methyl, $CF_3$, —OMe, $NO_2$, or 1-3 halo;
c) when $R^B$ is hydrogen and ring H is phenyl, with methyl, 1-2 methoxy or 1-2 halo substituents, then ring G is not phenyl substituted with $CF_3$ or 1-2 halo;
d) when $R^B$ is methyl and ring H phenyl substituted with butyl, then ring G is not phenyl substituted with methyl, or 1-2 halo; and
e) when $R^B$ and ring H are both unsubstituted phenyl, then ring G is not unsubstituted phenyl, or phenyl substituted with methyl, $CF_3$, OMe, $NO_2$, or 1-2 halo.

In certain embodiments, ring G is phenyl optionally substituted with up to two $R^1$. Exemplary R1includes C1-C4 alkyl, O—(C1-C4 alkyl), halo, or cyano.

In one embodiment, $R^B$ is C1-6 aliphatic optionally substituted with up to 4 substituents selected from $R^1$, $R^2$, $R^3$, $R^4$, or $R^5$. In certain embodiments, $R^B$ is C1-C4 alkyl optionally substituted with up to 2 substituents selected from $R^1$. Exemplary $R^B$ include methyl, ethyl, n-propyl, isopropyl, sec-butyl, n-butyl, or t-butyl.

In other embodiments, $R^B$ is a 3-7 membered monocyclic saturated, unsaturated or aromatic ring containing 0-4 heteroatoms optionally substituted with up to 4 substituents selected from $R^1$, $R^2$, $R^3$, $R^4$, or $R^5$. In certain embodiments, $R^B$ is a 3-7 membered monocyclic saturated, carbocyclic ring optionally substituted with up to 2 substituents selected from $R^1$. Exemplary rings include cyclopropyl, cyclopentyl, cyclohexyl, or cycloheptyl.

In other embodiments, $R^B$ is a 3-7 membered monocyclic saturated, unsaturated or aromatic ring containing 1-3 heteroatoms optionally substituted with up to 4 substituents selected from $R^1$, $R^2$, $R^3$, $R^4$, or $R^5$. In certain embodiments, $R^B$ is a 3-7 membered monocyclic saturated ring containing 1-3 heteroatoms optionally substituted with up to 2 substituents selected from $R^1$. Exemplary rings include piperidinyl, morpholinyl, or thiomorpholinyl.

In other embodiments, $R^B$ is a 8-14 membered bicyclic or tricyclic, saturated, unsaturated or aromatic ring containing 0-4 heteroatoms in each ring, wherein each said heteroatom is independently selected from N, NH, S, or O, optionally substituted with up to 4 substituents selected from $R^1$, $R^2$, $R^3$, $R^4$, or $R^5$.

According to another embodiment, the present invention provides compounds of formula IIC:

(IIC)

wherein:
Y' is O or S;
$X_7$ is O, S, or NR';
R' is hydrogen, $R^2$, or $R^6$;
R is hydrogen, $R^2$, or $R^6$;
$R^B$ is C1-6 aliphatic or a 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;
$R^C$ is C1-C6 aliphatic;
wherein each of ring G, $R^B$, and $R^C$ is independently and optionally substituted with up to 4 substituents selected from $R^1$, $R^2$, $R^3$, $R^4$, or $R^5$, as defined above.

According to one embodiment, $X_7$ is O. Or, $X_7$ is S. Or, $X_7$ is NR'.

According to one embodiments, $R^C$ is C1-C6 alkyl, optionally substituted with up to two substituents selected from $R^1$, $R^2$, $R^3$, $R^4$, or $R^5$. Or, $R^C$ is C1-C6 alkyl. Exemplary $R^C$ includes methyl, ethyl, isopropyl, n-propyl, n-butyl, sec-butyl, or t-butyl.

According to another embodiment, $R^B$ is phenyl optionally substituted with up to two R1 substituents. Or, $R^B$ is phenyl.

According to another embodiment, $R^B$ is C1-C6 alkyl. Exemplary $R^B$ includes methyl, ethyl, isopropyl, n-propyl, n-butyl, sec-butyl, or t-butyl.

In one embodiment, compound of formula IIC includes one or more of the following features:
a) ring G is benzyl optionally substituted with one R1 substituent, preferably halo;
b) Y' is S and R is hydrogen;
c) $R^C$ is C1-C4 alkyl;
d) $X_7$ is NH or NR' wherein R' is C1-C4 alkyl; and
e) $R^B$ is C1-C4 alkyl.

According to another embodiment, the present invention provides a compound of formula IID:

(IID)

wherein:
Y' is O or S;
R is hydrogen or $R^2$;
$X_8$ is O, S, or NR';
R' is hydrogen, $R^2$, or $R^6$;
$R^{BB}$ is C1-6 aliphatic or a 3-7 membered monocyclic or 8-14 membered bicyclic or tricyclic, saturated, unsaturated, or aromatic ring containing 0-4 heteroatoms in each ring, wherein each said heteroatom is independently selected from N, S, or O;
wherein each of ring G and $R^{BB}$ is independently and optionally substituted with up to 4 substituents selected from $R^1$, $R^2$, $R^3$, $R^4$, or $R^5$, as defined above.

In certain embodiments, $X_8$ is O. Or, $X_B$ is S. Or, $X_8$ is NR'.

According to another embodiment, $R^{BB}$ is phenyl optionally substituted with up to two $R^1$ substituents. Or, $R^{BB}$ is phenyl.

According to another embodiment, $R^{BB}$ is C1-C6 alkyl. Exemplary $R^{BB}$ includes methyl, ethyl, isopropyl, n-propyl, n-butyl, sec-butyl, or t-butyl.

According to another embodiment, $R^{BB}$ is optionally substituted C3-C8 cycloalkyl, e.g., cyclopropyl, cyclopentyl, or cyclohexyl.

According to another embodiment, $R^{BB}$ is optionally substituted benzyl.

In one embodiment, compounds of formula IID have one or more of the following features:
a) Y' is S and R is hydrogen;
b) each ring G is unsubstituted phenyl;
d) $X_8$ is NR', and R' is hydrogen or C1-C4 alkyl; and
e) $R^{BB}$ is C1-C4 alkyl, benzyl, cyclopentyl, or cyclohexyl.

According to another preferred embodiment, the present invention provides a compound having formula (III):

(III)

or a pharmaceutically acceptable salt thereof;
wherein:
$X_1$ is a bond, O, S, CHOR, C(O), C(O)O, $CF_2$, $CH_2$, or NR;
R is H or $R^2$
$A_1$ is (C2-C10) aliphatic, aryl, heteroaryl, heterocyclic, or cycloaliphatic;
each $B_1$ is independently selected from 3-7 membered monocyclic, saturated, unsaturated or aromatic ring containing 0-4 heteroatoms selected from N, NH, S, or O;
wherein each $A_1$ is optionally substituted with up to 4 substituents independently selected from $R^1$, $R^2$, $R^3$, $R^4$, or $R^5$;
$R^1$ is $R^6$ or $((C1-C4)aliphatic)_n$-Y;
n is 0 or 1;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ optionally comprises up to 2 substituents independently selected from $R^1$, $R^4$, or $R^5$;
$R^3$ is a cycloaliphatic, aryl, heterocyclic, or heteroaryl ring optionally comprising up to 3 substituents, independently selected from $R^1$, $R^2$, $R^4$ or $R^5$;

R⁴ is OR⁵, OR⁶, OC(O)R⁶, OC(O)R⁵, OC(O)OR⁶, OC(O)OR⁵, OC(O)N(R⁶)₂, OC(O)N(R⁵)₂, OC(O)N(R⁶R⁵), SR⁶, SR⁵, S(O)R⁶, S(O)R⁵, SO₂R⁶, SO₂R⁵, SO₂N(R⁶)₂, SO₂N(R⁵)₂, SO₂NR⁵R⁶, SO₃R⁶, SO₃R⁵, C(O)R⁵, C(O)OR⁵, C(O)R⁶, C(O)OR⁶, C(O)N(R⁶)₂, C(O)N(R⁵)₂, C(O)N(R⁵R⁶), C(O)N(OR⁶)R⁶, C(O)N(OR⁵)R⁶, C(O)N(OR⁶)R⁵, C(O)N(OR⁵)R⁵, C(NOR⁶)R⁶, C(NOR⁶)R⁵, C(NOR⁵)R⁶, C(NOR⁵)R⁵, N(R⁶)₂, N(R⁵)₂, N(R⁵R⁶), NR⁵C(O)R⁵, NR⁶C(O)R⁶, NR⁵C(O)R⁵, NR⁶C(O)R⁶, NR⁵C(O)OR⁶, NR⁶C(O)OR⁵, NR⁵C(O)OR⁵, NR⁶C(O)N(R⁶)₂, NR⁶C(O)NR⁵R⁶, NR⁶C(O)N(R⁵)₂, NR⁵C(O)N(R⁶)₂, NR⁵C(O)NR⁵R⁶, NR⁵C(O)N(R⁵)₂, NR⁶SO₂R⁶, NR⁵SO₂R⁵, NR⁵SO₂R⁵, NR⁵SO₂R⁶, NR⁶SO₂N(R⁶)₂, NR⁶SO₂NR⁵R⁶, NR⁶SO₂N(R⁵)₂, NR⁵SO₂NR⁵R⁶, NR⁵SO₂N(R⁵)₂, N(OR⁶)R⁶, N(OR⁶)R⁵, N(OR⁵)R⁵, or N(OR⁵)R⁶;

R⁵ is a cycloaliphatic, aryl, heterocyclic, or heteroaryl ring, optionally comprising up to 3 R¹ substituents;

R⁶ is H or aliphatic, wherein R⁶ optionally comprises a R⁷ substituent;

R⁷ is a cycloaliphatic, aryl, heterocyclic, or heteroaryl ring, and each R⁷ optionally comprises up to 2 substituents independently chosen from H, (C₁-C₆)-straight or branched alkyl, (C₂-C₆) straight or branched alkenyl or alkynyl, 1,2-methylenedioxy, 1,2-ethylenedioxy, or (CH₂)ₙ—Z.

Z is selected from halo, CN, NO₂, CF₃, OCF₃, OH, S-aliphatic, S(O)-aliphatic, SO₂-aliphatic, NH₂, N-aliphatic, N(aliphatic)₂, N(aliphatic)R⁸, COOH, C(O)O(-aliphatic, or O-aliphatic; and R⁸ is an amino capping group;

provided that:

(i) when X₁ is a bond, one B₁ is phenyl and the other B₁ is N-piperidyl, then A is not:

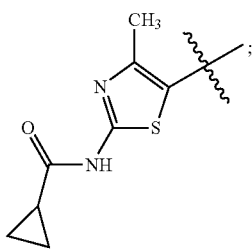 [SMILES: *c1sc(NC(=O)C2CC2)nc1C]

and (ii) when X₁ is a bond, then A₁ is not an optionally substituted 6-membered heteroaryl ring with 1-3 nitrogen ring atoms.

In certain embodiments, According to another embodiment of formula (III), X₁ is CH₂, CF₂, or O. In another embodiment, X₁ is a bond, O, S, CF₂, CH₂, or NR. Or, X₁ is CH₂ or O. Or, X₁ is CH₂.

According to another embodiment of formula (III), A₁ is an optionally substituted C3-C7 cycloaliphatic ring. In certain embodiments, A₁ is an optionally substituted cyclopropyl, cyclopentyl, or cyclohexyl.

According to another embodiment of formula (III), A₁ is optionally substituted (C1-C10)aliphatic. In certain embodiments, A₁ is optionally substituted methyl, ethyl, propyl, butyl, pentyl, or hexyl.

According to another embodiment of formula (III), A₁ is optionally substituted C6-C10 aryl ring. In certain embodiments, A₁ is optionally substituted phenyl or naphthyl.

According to another embodiment of formula (III), A₁ is optionally substituted C5-C12 heteroaryl ring. In certain embodiments, A is selected from optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, acridinyl, phenazinyl, phenothiazinyl, or phenoxazinyl.

According to another embodiment of formula (III), A₁ is optionally substituted C3-C12 heterocyclic ring. In certain embodiments, A₁ is selected from optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

According to another embodiment of formula (III), each B₁ is independently selected from optionally substituted C6-C10 aryl. In certain embodiments, each B₁ is independently an optionally substituted, phenyl or naphthyl. Or, each B₁ is an unsubstituted phenyl.

According to another embodiment of formula (III), each B₁ is independently selected from optionally substituted C5-C12 heteroaryl. In certain embodiments, each B₁ is independently and optionally substituted C5-C7 heteroaryl. Or, each B₁ is independently selected from optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, carbazolyl, acridinyl, phenazinyl, phenothiazinyl, phenoxazinyl, indenyl, naphthyl, azulinyl, or anthracenyl.

According to another embodiment of formula (III), each B₁ is independently an optionally substituted 3-12 membered heterocyclic ring having up to 4 heteroatoms selected from O, S, or NR. In certain embodiments, each B₁ is independently selected from optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

Exemplary embodiments of R¹, R², R³, R⁴, R⁵, R⁶, R⁷, R⁸ and Z in compounds of formula (III) are as described above for compound of formula (I).

According to another embodiment, the present invention provides compounds of formula IV:

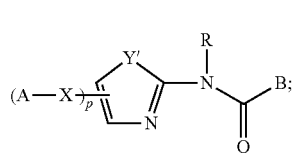

wherein:
B is selected from:

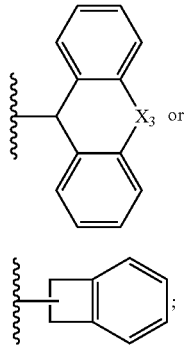

wherein:
Y is O or S; and
$X_3$ is O or S.

According to one embodiment, $X_3$ is O. Or, $X_3$ is S.
According to one embodiment, B is structure (i) above. Or, B is structure (ii) above.
According to another embodiment, R is hydrogen.
According to another embodiment, Y' is S. Or, Y' is O.
According to another embodiment, the present invention provides compounds of formula V:

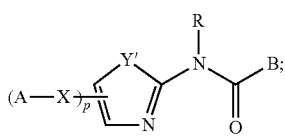

wherein:
Y' is O or S;
B is selected from:

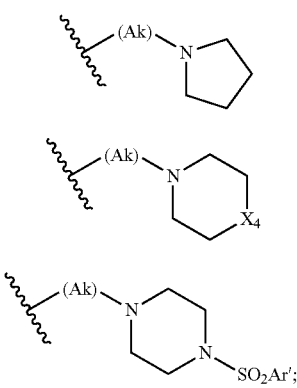

wherein:
Ak is C1-C6 alkylidene;
$X_4$ is $CH_2$, O or S;
Ar' is phenyl optionally substituted with up to two $R^1$; and
B is optionally substituted with up to two $R^1$.
In some embodiments, Ak is selected from $CH_2$, $CH(CH_3)$, $C(CH_3)_2$, CH(Et), $C(Et)_2$, CH(n-propyl), CH(i-Pr), CH(n-butyl), CH(but-2yl), or CH(t-butyl).

In some embodiments, Ar' is phenyl optionally substituted with halo, C1-C4 alkyl, or O—(C1-C4 alkyl).
In some embodiments, $X_4$ is $CH_2$. $X_4$ is S. Or, $X_4$ is O.
In some embodiments, R is hydrogen.
In certain, embodiments, p is 2, X is a bond, and each A is optionally substituted phenyl.
In other embodiments, the compounds have one or more of the following features:
a) Y' is S;
b) R is hydrogen;
c) p is 2, X is a bond, and each A is phenyl;
d) B is ring (iii) above, wherein Ak is $CH(CH_3)$ and Ar' is phenyl optionally substituted with halo, C1-C4 alkyl, or O—(C1-C4 alkyl).
According to another embodiment, the present invention provides a compound of formula VI:

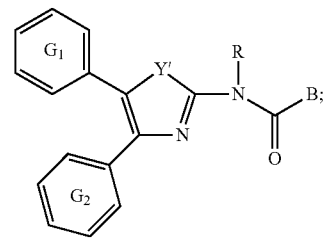

Y' is O or S;
R is hydrogen or $R^2$;
B is phenyl, 3-7 membered, monocyclic, saturated, carbocyclic ring, or 3-10 membered saturated or unsaturated, monocyclic or bicyclic heterocyclic ring having up to 4 heteroatoms selected from O, S, or N, or 5-10 membered monocyclic or bicyclic heteroaryl ring having up to 4 heteroatoms selected from O, S, or N;
  wherein each ring $G_1$, $G_2$, and B is independently substituted with up to 4 substituents selected from $R^1$, $R^2$, $R^3$, $R^4$, or $R^5$;
$R^1$ is oxo, $R^6$ or ((C1-C4)aliphatic)$_n$-Y;
n is 0 or 1;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)_2$, COOH, $COOR^6$ or $OR^6$; or
two $R^1$ on adjacent ring atoms, taken together, form 1,2-methylenedioxy or 1,2-ethylenedioxy;
$R^2$ is aliphatic, wherein each $R^2$ optionally comprises up to 2 substituents independently selected from $R^1$, $R^4$, or $R^5$;
$R^3$ is a cycloaliphatic, aryl, heterocyclic, or heteroaryl ring optionally comprising up to 3 substituents, independently selected from $R^1$, $R^2$, $R^4$ or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^5C(O)R^6$, $NR^6C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, NR⁶SO₂N(R⁶)₂, NR⁶SO₂NR⁵R⁶, NR⁶SO₂N(R⁵)₂, NR⁵SO₂N(R⁶)₂, NR⁵SO₂NR⁵R⁶, NR⁵SO₂N(R⁵)₂, N(OR⁶)R⁶, N(OR⁶)R⁵, N(OR⁵)R⁵, or N(OR⁵)R⁶;

R⁵ is a cycloaliphatic, aryl, heterocyclic, or heteroaryl ring, optionally comprising up to 3 R¹ substituents;

R⁶ is H or aliphatic, wherein R⁶ optionally comprises a R⁷ substituent;

R⁷ is a cycloaliphatic, aryl, heterocyclic, or heteroaryl ring, and each R⁷ optionally comprises up to 2 substituents independently chosen from H, (C₁-C₆)-straight or branched alkyl, (C₂-C₆) straight or branched alkenyl or alkynyl, 1,2-methylenedioxy, 1,2-ethylenedioxy, or (CH₂)ₙ—Z;

Z is selected from halo, CN, NO₂, CF₃, OCF₃, OH, S-aliphatic, S(O)-aliphatic, SO₂-aliphatic, NH₂, NH-aliphatic, N(aliphatic)₂, N(aliphatic)R⁸, NHR⁸, N(R⁸)₂, COOH, C(O)O(-aliphatic, or O-aliphatic; and R⁸ is an amino capping group.

In certain embodiments of formula VI, when R is hydrogen, then the following compounds are excluded:

a) B is not quinolin-2-yl or 1,2-dihydro-2-oxo-quinolin-4-yl;

b) when G₁ and G₂ both are phenyl, and Y' is S, then B is not 1,4-benzodioxin-2-yl, cyclopropyl, cyclohexyl, thien-2-yl, 1H-thieno[2,3-c]pyrazol-1-phenyl-3-methyl-5-yl, 5-methyl-thien-3-yl, 2,5-dichloro-thien-3-yl, 2-phenyl-quinolin-4-yl, furan-2-yl, thien-5-(4,5-diphenyl-2-thiazolyl-carboxamide)-2-yl, benzo[b]thiophen-2-yl, pyridin-2-(4,5-diphenyl-2-thiazolyl-carboxamide)-6-yl, 5-nitro-thien-2-yl, 3-chloro-benzo[b]thiophen-2-yl, 4H-1-benzopyran-3-yl or 2H-1-benzopyran-3,4-dihydro-3-oxo-4-yl, 4H-1-benzopyran-3-yl or 2H-1-benzopyran-3,4-dihydro-3oxo-4-yl;

c) when G₁ and G₂ both are phenyl, and Y' is O, then B is not 1,2-dihydro-2-oxo-quinolin-4-yl or 3,4-dihydro-3-phenyl-phthalazin-1-yl or thien-2-yl;

d) the following compounds are excluded:

| Y' | G₁ | G₂ | B |
|---|---|---|---|
| S | Ph | 4-Me—Ph | 2-Cl-thien-5-yl or 2,5-dichloro-thien-3-yl |
| S | Ph or 3,4-dimethyl phenyl | 3,4-dimethyl phenyl or Ph | pyridin-3-yl |
| S | 3,4-dimethyl phenyl | Ph | pyridin-4-yl |
| S | 4-Cl—Ph | Ph | thien-2-yl |
| S | 3,4-dimethyl phenyl | Ph | pyridin-4-yl |
| S | Ph | 4-Me-phenyl | thien-2-yl or benzothiazol-2-yl |
| S | 4-NO₂—Ph or 4-Me—Ph | Ph or 4-OMe—Ph or 2,4-dimethylphenyl | thien-2-yl or furan-2-yl |
| S | 4-OMe—Ph or 2,4-dimethylphenyl | 4-NO₂—Ph | furan-2-yl or thien-2-yl |
| S | 4-OMe—Ph or Ph | 4-OMe—Ph | furan-2-yl or thien-2-yl |
| S | Ph | 4-Me—Ph | furan-2-yl |
| S | Ph | 4-Me—Ph | 5-nitro-thien-2-yl |
| S | 4-Me—Ph | 4-Me—Ph | 2-chloro-pyridin-3-yl |
| S | Ph | 4-Me—Ph | 3-chloro-benzo[b]thiophen-2-yl |
| S | 4-Me—Ph or Ph | 4-NO₂—Ph | thien-2-yl or furan-2-yl |
| S | 2,4-dimethylphenyl | 4-NO₂—Ph | pyridin-3-yl or thien-2-yl |
| S | 4-Cl—Ph | 4-NO₂—Ph | thien-2-yl |

| Y' | G₁ | G₂ | B |
|---|---|---|---|
| S | Ph or 2-OMe—Ph or 3-OMe—Ph or 4-OMe—Ph | 2,4-dimethoxy-phenyl | 1H-indol-2-yl. | d) when Y' is S, G₁ and G₂ are both phenyl, then B is not

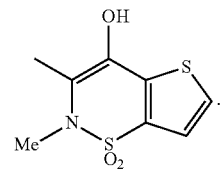

In one embodiment, G₁ and G₂ are both phenyl. Or, each is independently and optionally substituted with up to two substituents selected from halo, or C1-C4 alkyl.

In certain embodiments of formula VI, B is phenyl optionally substituted with up to two substituents selected from halo, C1-C4 alkyl, O—(C1-C4 alkyl), COOH, COO(C1-C4 alkyl), or cyano.

In other embodiments, B is 3,4-dichlorophenyl, 4-chlorophenyl, 4-methoxyphenyl, 4-methylphenyl, 2,6-difluorophenyl, 2-methylphenyl, 3-methylphenyl, phenyl-2-carboxylic acid, 2-chlorophenyl, 4-cyanophenyl, or 3-methoxyphenyl.

In another embodiment, B is 3-7 membered, monocyclic, saturated, carbocyclic ring. Exemplary rings include cyclopropyl, cyclopentyl, cyclohexyl, or cycloheptyl.

In another embodiment, B is a 3-10 membered saturated or unsaturated, monocyclic or bicyclic heterocyclic ring having up to 4 heteroatoms selected from O, S, or N. Exemplary rings include tetrahydrofuranyl, thienyl, or pyrrolyl.

In another embodiment, B is a 5-10 membered monocyclic or bicyclic heteroaryl ring having up to 4 heteroatoms selected from O, S, or N.

According to another embodiment, the present invention provides a compound of formula VII:

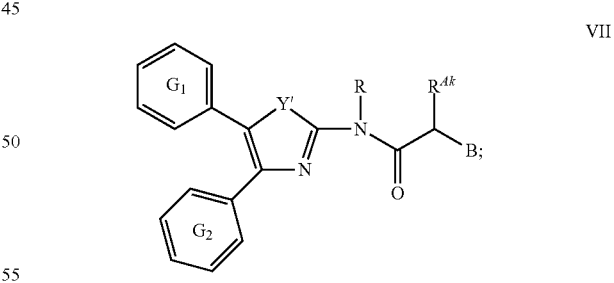

wherein:
Y' is O or S;
R is hydrogen or R²;
R^{Ak} is C1-C6 aliphatic, optionally substitute with up to 3 substituents independently selected from R¹, R², or R³;
B is phenyl, 3-7 membered, monocyclic, saturated, carbocyclic ring, or 3-10 membered saturated or unsaturated, monocyclic or bicyclic heterocyclic ring having up to 4 heteroatoms selected from O, S, or N, or 5-10 membered monocyclic or bicyclic heteroaryl ring having up to 4 heteroatoms selected from O, S, or N;

wherein each ring $G_1$, $G_2$, and B is independently substituted with up to 4 substituents selected from $R^1$, $R^2$, $R^3$, $R^4$, or $R^5$;

$R^1$ is oxo, $R^6$ or ((C1-C4)aliphatic)$_n$-Y;

n is 0 or 1;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, $N(R^8)_2$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ optionally comprises up to 2 substituents independently selected from $R^1$, $R^4$, or $R^5$;

$R^3$ is a cycloaliphatic, aryl, heterocyclic, or heteroaryl ring optionally comprising up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^5SO_2R^6$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each optionally comprises up to 2 substituents independently chosen from H, ($C_1$-$C_6$)-straight or branched alkyl, ($C_2$-$C_6$) straight or branched alkenyl or alkynyl, 1,2-methylenedioxy, 1,2-ethylenedioxy, or $(CH)_n$—Z;

Z is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, N(aliphatic)$R^8$, $NHR^8$, $N(R^8)_2$, COOH, C(O)O(-aliphatic, or O-aliphatic; and $R^8$ is an amino-capping group.

In one embodiment of formula VII, when each of $G_1$, $G_2$, and B is unsubstituted phenyl, and R is hydrogen, then B is not 3,4,5-trimethoxyphenyl.

In one embodiment, $R^{Ak}$ is C1-C6 alkyl. Exemplary $R^{Ak}$ include methyl, ethyl, isopropyl, n-propyl, sec-butyl, n-butyl, or t-butyl.

In one embodiment, B is optionally substituted phenyl.

In another embodiment, B is 3-7 membered, monocyclic, saturated, carbocyclic ring. Exemplary rings include cyclopropyl, cyclopentyl, cyclohexyl, or cycloheptyl.

In another embodiment, B is a 3-10 numbered saturated or unsaturated, monocyclic or bicyclic heterocyclic ring having up to 4 heteroatoms selected from O, S, or N. Exemplary rings include tetrahydrofuranyl, tetrahydrothiophenyl, pyrrolidinyl, or piperazinyl.

In another embodiment, B is a 5-10 membered monocyclic or bicyclic heteroaryl ring having up to 4 heteroatoms selected from O, S, or N.

According to another embodiment, the present invention provides a compound having formula I':

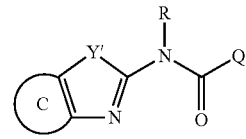

I' or a pharmaceutically acceptable salt thereof;

wherein:

Y' is O, S, or NR; R is H, $R^2$, or $R^6$;

C is a phenyl or 5-8 membered cycloaliphatic ring;

Q is selected from:

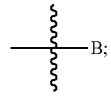

(a)

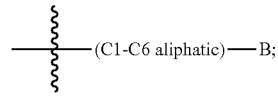

(b)

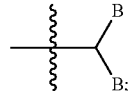

(c)

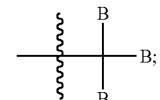

(d)

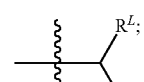

(e)

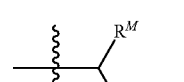

(f)

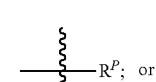

(g)

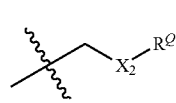

(h)

each B is independently selected from 3-7 membered monocyclic or 8-14 membered bicyclic or tricyclic, saturated, unsaturated or aromatic ring containing 0-4 heteroatoms in each ring, wherein each said heteroatom is independently selected from N, NH, S, or O;

wherein each A, B, and C is independently and optionally substituted with up to 4 substituents independently selected from $R^1$, $R^2$, $R^3$, $R^4$, or $R^5$;

$R^L$ is —$OR^A$, —$SR^A$, or —$N(R^{AB})_2$;

each $R^A$ is independently hydrogen, C1-C6 aliphatic, or a 3-7 membered carbocyclic or heterocyclic ring, saturated or unsaturated ring, having up to 3 heteroatoms selected from O, N, or S, wherein each $R^A$ is optionally substituted with up to 3 substituents independently selected from $R^1$, $R^4$ or $R^7$, each $R^{AB}$ is independently hydrogen or C1-C6 aliphatic optionally substituted with up to 3 substituents independently selected from $R^1$, $R^4$ or $R^7$;

wherein up to two methylene units in $R^A$ or $R^{AB}$ are optionally replaced with —CO—, —CS—, —COCO—, —CONR—, —CO$_2$—, —OCO—, —NRCO$_2$—, —O—, —NRCONR—, —OCONR—, —NRCO—, —S—, —SO, —SO$_2$—, —NR—, —SO$_2$NR—, NRSO$_2$—, or —NRSO$_2$NR; or two $R^{AB}$, taken together with the nitrogen atom, is a 3-7 membered heterocyclic or heteroaryl ring containing up to 4 heteroatoms selected from O, N, or S, wherein said ring is optionally substituted with up to 2 substituents selected from oxo or $(C_{1-4}\text{aliphatic})_p$-Y;

$R^M$ is C1-C6 aliphatic, optionally substituted with up to two substituents selected from $R^1$, $R^2$, $R^3$, or $R^4$;

each of $X_1$ and $X_2$ is independently selected from O, S, or NR;

$R^N$ is C1-C6 aliphatic or phenyl, wherein $R^N$ is optionally substituted with up to two substituents selected from $R^1$, $R^2$, $R^3$, or $R^4$;

$R^P$ is C1-C6 aliphatic, optionally substituted with up to two substituents selected from $R^1$, $R^2$, $R^3$, or $R^4$;

$R^Q$ is C1-C6 aliphatic or aryl, wherein $R^Q$ is optionally substituted with up to two substituents selected from $R^1$, $R^2$, $R^3$, or $R^4$;

$R^1$ is oxo, $R^6$ or $((C1\text{-}C4)\text{aliphatic})_n$-Y;

n is 0 or 1;

Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, N(R$^8$)$^2$, COOH, COOR$^6$ or OR$^6$; or two $R^1$ on adjacent ring atoms, taken together, form 1,2-methylenedioxy or 1,2-ethylenedioxy;

$R^2$ is aliphatic, wherein each $R^2$ optionally comprises up to 2 substituents independently selected from $R^1$, $R^4$, or $R^5$;

$R^3$ is a cycloaliphatic, aryl, heterocyclic, or heteroaryl ring optionally comprising up to 3 substituents, independently selected from $R^1$, $R^2$, $R^4$ or $R^5$;

$R^4$ is OR$^5$, OR$^6$, OC(O)R$^6$, OC(O)R$^5$, OC(O)OR$^6$, OC(O) OR$^5$, OC(O)N(R$^6$)$_2$, OC(O)N(R$^5$)$_2$, OC(O)N(R$^6$R$^5$), SR$^6$, SR$^5$, S(O)R$^6$, S(O)R$^5$, SO$_2$R$^6$, SO$_2$R$^5$, SO$_2$N(R$^6$)$_2$, SO$_2$N(R$^5$)$_2$, SO$_2$NR$^5$R$^6$, SO$_3$R$^6$, SO$_3$R$^5$, C(O)R$^5$, C(O) OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O) N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^5$C(O)R$^5$, NR$^6$C(O)R$^6$, NR$^6$C(O)R$^5$, NR$^5$C(O)R$^6$, NR$^6$C(O)OR$^6$, NR$^5$C(O)OR$^6$, NR$^6$C(O)OR$^5$, NR$^5$C(O) OR$^5$, NR$^6$C(O)N(R$^6$)$_2$, NR$^6$C(O)NR$^5$R$^6$, NR$^6$C(O)N (R$^5$)$_2$, NR$^5$C(O)N(R$^6$)$_2$, NR$^5$C(O)NR$^5$R$^6$, NR$^5$C(O)N (R$^5$)$_2$, NR$^6$SO$_2$R$^6$, NR$^6$SO$_2$R$^5$, NR$^5$SO$_2$R$^5$, NR$^5$SO$_2$R$^6$, NR$^6$SO$_2$N(R$^6$)$_2$, NR$^6$SO$_2$NR$^5$R$^6$, NR$^6$SO$_2$N(R$^5$)$_2$, NR$^5$SO$_2$N(R$^6$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, or N(OR$^5$)R$^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each $R^7$ optionally comprises up to 2 substituents independently chosen from H, $(C_1\text{-}C_6)$-straight or branched alkyl, $(C_2\text{-}C_6)$ straight or branched alkenyl or alkynyl, 1,2-methylenedioxy, 1,2-ethylenedioxy, or $(CH_2)_n$—Z;

Z is selected from halo, CN, NO$_2$, CF$_3$, OCF$_3$, OH, S-aliphatic, S(O)-aliphatic, SO$_2$-aliphatic, NH$_2$, NH-aliphatic, N(aliphatic)$_2$, N(aliphatic)R$^8$, NHR$^8$, N(R$^8$)$_2$, COOH, C(O)O(-aliphatic, or O-aliphatic; and $R^8$ is an amino-capping group.

In one embodiment, Y' is O. Or, Y' is S.

In another embodiment, R is hydrogen.

In one embodiment, Q in formula I' is B (structure (a)). Preferred B include optionally substituted phenyl, or C3-C8 cycloaliphatic. In one embodiment, B in formula I' is phenyl or C3-C8 cycloalkyl optionally substituted with up to two substituents selected from $R^1$, $R^2$, or phenyl optionally substituted with up to two substituents selected from $R^1$ or $R^2$.

In another embodiment, Q in formula I' is —(C1-C6 aliphatic)-B (structure (b)).

In certain embodiments, said C1-C6 aliphatic is C1-C4 straight or branched alkylidene. Exemplary alkylidenes include —CH$_2$—, —CH(Me)-, —C(Me)$_2$-, —CH(Et)-, —C(Et)$_2$-, or —CH$_2$—CH (Me)-.

In certain embodiments, B is selected from optionally substituted C3-C8 cycloalkyl, phenyl, piperidyl, or pyrrolidinyl. Preferably, B is phenyl, cyclopentyl, cyclohexyl, or piperidyl, optionally substituted with up to two $R^1$ or $R^2$ substituents.

In one embodiment, ring C is phenyl optionally substituted with up to two $R^1$. Or ring C is cyclohexenyl optionally substituted with up to two $R^1$.

According to a preferred embodiment, $R^1$ is 1,2-methylene dioxy, or 1,2-ethylenedioxy.

According to another preferred embodiment, $R^1$ is $R^6$, wherein $R^6$ is straight chain or branched (C1-C6)alkyl or (C2-C6) alkenyl or alkynyl, optionally substituted with $R^7$.

According to another preferred embodiment, $R^1$ is (C1-C4 aliphatic)$_n$-Y, wherein n is 0 or 1, and Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$;

According to another preferred embodiment, $R^1$ is selected from halo, CF$_3$, NH$_2$, NH(C1-C4 alkyl), NHC(O)CH$_3$, OH, O(C1-C4 alkyl), OPh, O-benzyl, S—(C1-C4 alkyl), C1-C4 aliphatic, CN, methylenedioxy, ethylenedioxy, SO$_2$NH(C1-C4 alkyl), or SO$_2$N(C1-C4 alkyl)$_2$.

According to another more preferred embodiment, $R^1$ is selected from methyl, n-propyl, i-propyl, t-butyl, halo, CF$_3$, NH$_2$, NH(CH$_3$), NHC(O)CH$_3$, OH, OCH$_3$, OPh, O-benzyl, S—(C$_2$H$_5$), S—CH$_3$, NO$_2$, CN, methylenedioxy, SO$_2$NH(n-propyl), or SO$_2$N(n-propyl)$_2$.

According to a preferred embodiment, $R^2$ is a straight chain or branched (C1-C6)alkyl or (C2-C6) alkenyl or alkynyl, optionally substituted with $R^1$, $R^4$, or $R^5$. More preferably, $R^2$ is a straight chain or branched (C1-C4)alkyl or (C2-C4) alkenyl or alkynyl, optionally substituted with $R^1$, $R^4$, or $R^5$.

In formula I', other embodiments of B, $R^L$, $R^M$, $R^N$, $R^P$, $R^Q$, $X_1$, $X_2$, and R are as described above for formula I.

Exemplary compounds of the present invention are shown below in Table 1.

TABLE 1

| Cmpd # | Compound |
|---|---|
| 1 |  |

TABLE 1-continued

| Cmpd # | Compound |
|---|---|
| 2 | 4-(2,4-dimethylphenyl)-N-benzoyl-thiazol-2-amine |
| 3 | 4-(2,5-dimethylphenyl)-2-(pentanoylamino)thiazole |
| 4 | 4-(2-methoxyphenyl)-2-(4-methylbenzoylamino)thiazole |
| 5 | 4-(2-methoxyphenyl)-2-(3-methylbenzoylamino)thiazole |
| 6 | 4-(2-methoxyphenyl)-2-(4-methoxybenzoylamino)thiazole |
| 7 | 4-(2-methoxyphenyl)-2-(3-methoxybenzoylamino)thiazole |
| 8 | N-(4,5,6,7-tetrahydrobenzothiazol-2-yl)-3-bromobenzamide |
| 9 | N-(4-(thiophen-2-yl)thiazol-2-yl)-3-bromobenzamide |
| 10 | N-(benzothiazol-2-yl)-4-ethylbenzamide |
| 11 | N-(benzothiazol-2-yl)-4-propylbenzamide |
| 12 | N-(benzothiazol-2-yl)-4-butylbenzamide |
| 13 | N-(thiazol-2-yl)-4'-methoxybiphenyl-4-carboxamide |
| 14 | N-(benzothiazol-2-yl)-4'-methoxybiphenyl-4-carboxamide |

TABLE 1-continued

| Cmpd # | Compound |
|---|---|
| 15 | |
| 16 | |
| 17 | |
| 18 | |
| 19 | |
| 20 | |
| 21 | |
| 22 | |
| 23 | |
| 24 | |
| 25 | |

TABLE 1-continued
| Cmpd # | Compound |
|---|---|
| 26 | 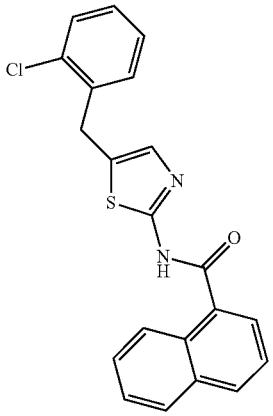 [SMILES: O=C(Nc1ncc(Cc2ccccc2Cl)s1)c1cccc2ccccc12] |
| 27 | 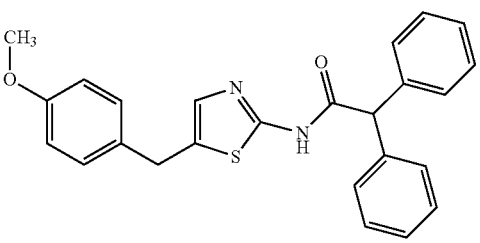 [SMILES: COc1ccc(Cc2cnc(NC(=O)C(c3ccccc3)c3ccccc3)s2)cc1] |
| 28 | 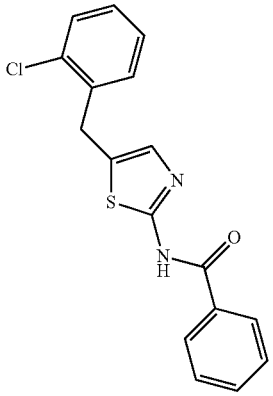 [SMILES: O=C(Nc1ncc(Cc2ccccc2Cl)s1)c1ccccc1] |
| 29 | 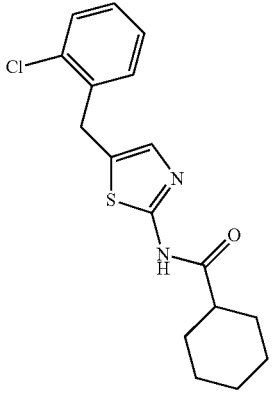 [SMILES: O=C(Nc1ncc(Cc2ccccc2Cl)s1)C1CCCCC1] |
| 30 | 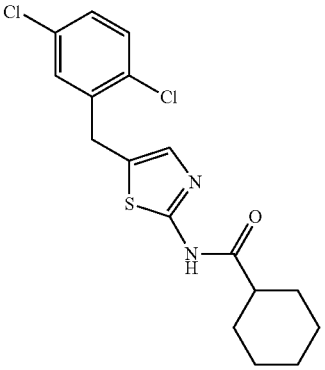 [SMILES: O=C(Nc1ncc(Cc2cc(Cl)ccc2Cl)s1)C1CCCCC1] |
| 31 | 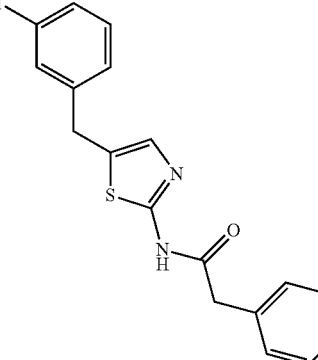 |
| 32 | 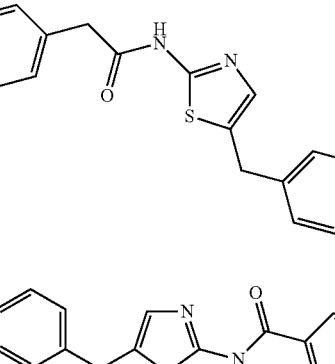 |
| 33 | 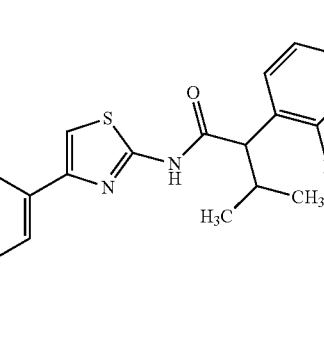 |
| 34 | 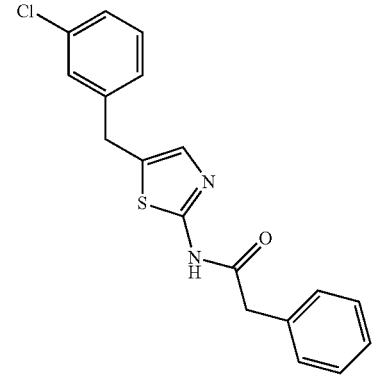 [SMILES: O=C(Cc1ccccc1)Nc1ncc(Cc2cccc(Cl)c2)s1] |

TABLE 1-continued

| Cmpd # | Compound |
| --- | --- |
| 35 | |
| 36 | |
| 37 | |
| 38 | |
| 39 | |
| 40 | |
| 41 | |
| 42 | |

TABLE 1-continued
| Cmpd # | Compound |
|---|---|
| 43 | |
| 44 | |
| 45 | |
| 46 | |
| 47 | |
| 48 | |
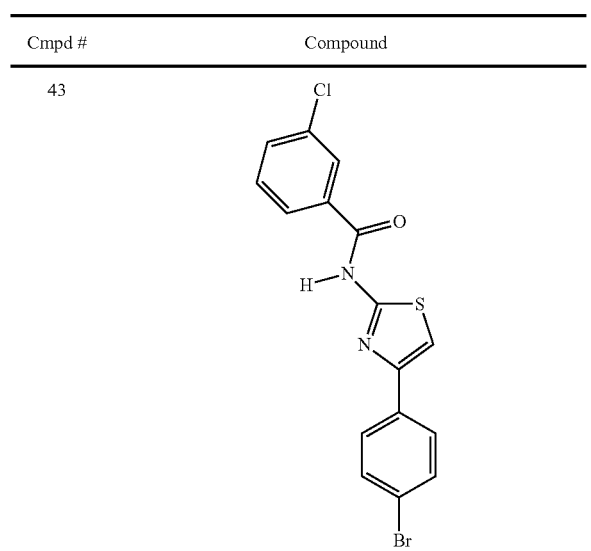
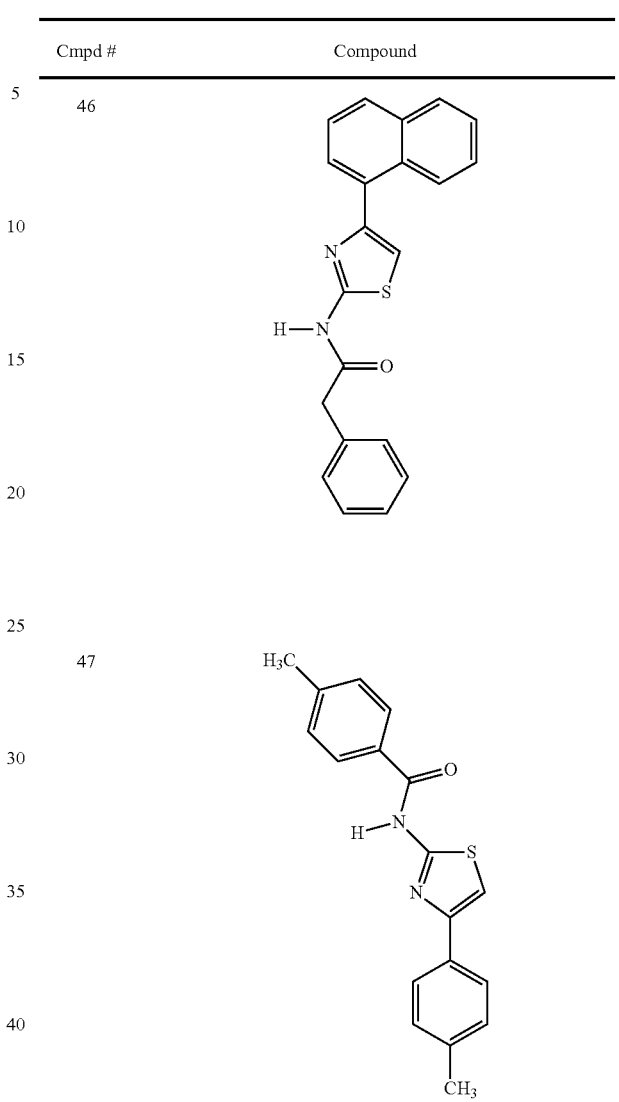

TABLE 1-continued
| Cmpd # | Compound |
|---|---|
| 49 | 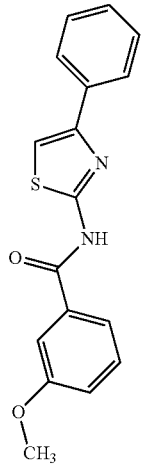 [SMILES: COc1cccc(C(=O)Nc2nc(-c3ccccc3)cs2)c1] |
| 50 | 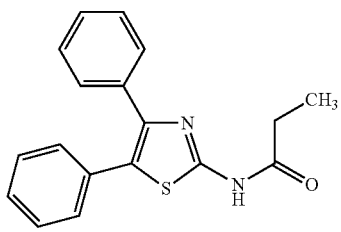 [SMILES: CCC(=O)Nc1nc(-c2ccccc2)c(-c2ccccc2)s1] |
| 51 | 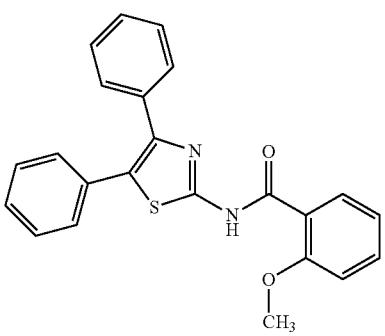 [SMILES: COc1ccccc1C(=O)Nc1nc(-c2ccccc2)c(-c2ccccc2)s1] |
| 52 | 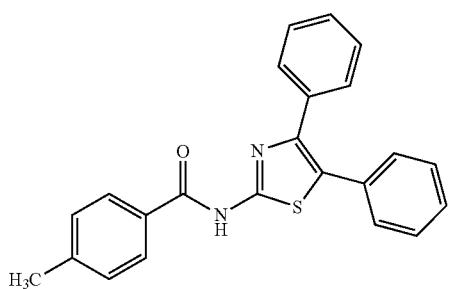 [SMILES: Cc1ccc(C(=O)Nc2nc(-c3ccccc3)c(-c3ccccc3)s2)cc1] |
| 53 | 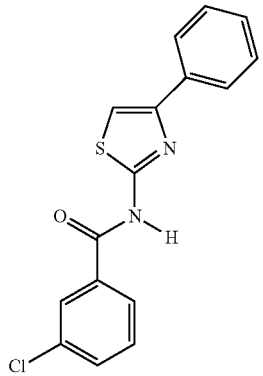 [SMILES: O=C(Nc1nc(-c2ccccc2)cs1)c1cccc(Cl)c1] |
| 54 | 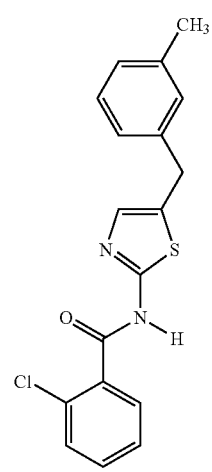 [SMILES: Cc1cccc(Cc2cnc(NC(=O)c3ccccc3Cl)s2)c1] |
| 55 | 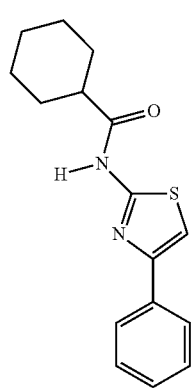 [SMILES: O=C(Nc1nc(-c2ccccc2)cs1)C1CCCCC1] |

TABLE 1-continued

| Cmpd # | Compound |
|---|---|
| 56 | *(structure)* |
| 57 | *(structure)* |
| 58 | *(structure)* |
| 59 | *(structure)* |
| 60 | *(structure)* |
| 61 | *(structure)* |
| 62 | *(structure)* |
| 63 | *(structure)* |
| 64 | *(structure)* |

TABLE 1-continued
| Cmpd # | Compound |
|---|---|
| 65 | 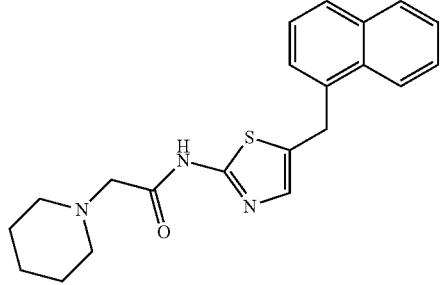 [SMILES: O=C(CN1CCCCC1)Nc1ncc(Cc2cccc3ccccc23)s1] |
| 66 | 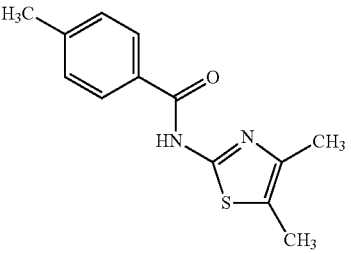 |
| 67 | 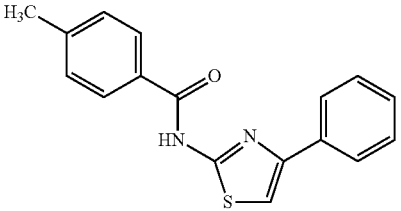 [SMILES: Cc1ccc(C(=O)Nc2nc(-c3ccccc3)cs2)cc1] |
| 68 | 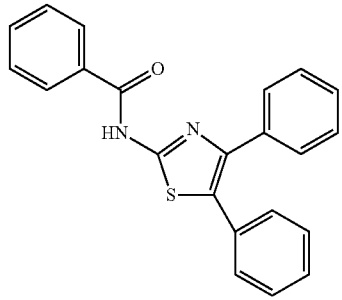 [SMILES: O=C(Nc1nc(-c2ccccc2)c(-c2ccccc2)s1)c1ccccc1] |
| 69 | 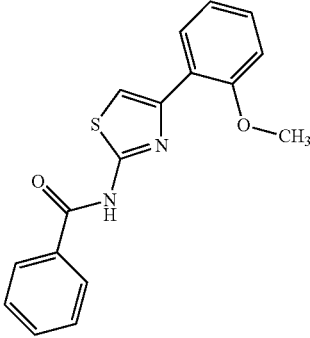 [SMILES: COc1ccccc1-c1csc(NC(=O)c2ccccc2)n1] |
| 70 | 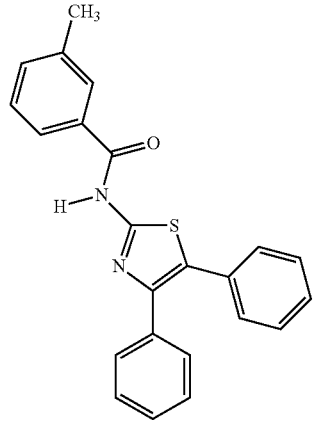 [SMILES: Cc1cccc(C(=O)Nc2nc(-c3ccccc3)c(-c3ccccc3)s2)c1] |
| 71 | 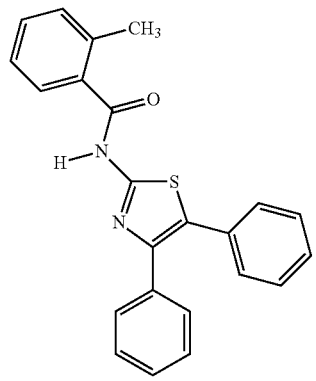 [SMILES: Cc1ccccc1C(=O)Nc1nc(-c2ccccc2)c(-c2ccccc2)s1] |
| 72 | 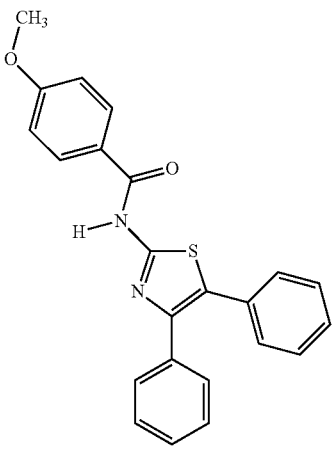 [SMILES: COc1ccc(C(=O)Nc2nc(-c3ccccc3)c(-c3ccccc3)s2)cc1] |

TABLE 1-continued
| Cmpd # | Compound |
|---|---|
| 73 | 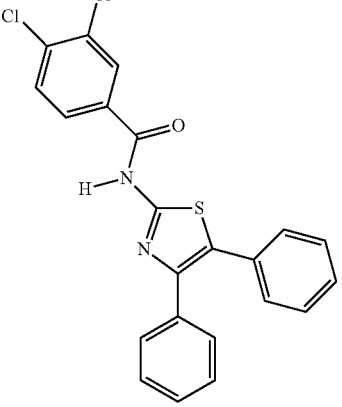 |
| 74 | 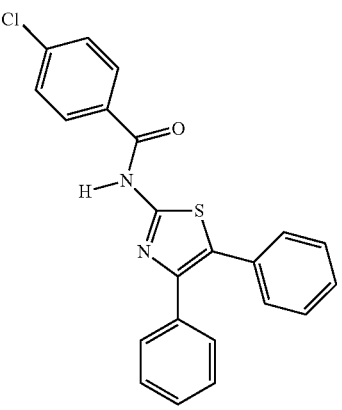 [SMILES: O=C(Nc1nc(-c2ccccc2)c(-c2ccccc2)s1)c1ccc(Cl)cc1] |
| 75 | 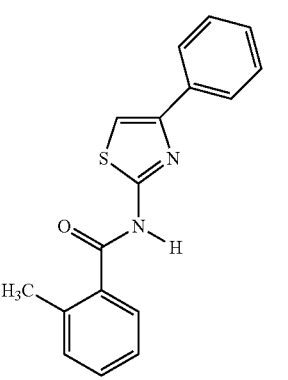 [SMILES: Cc1ccccc1C(=O)Nc1nc(-c2ccccc2)cs1] |
| 76 | 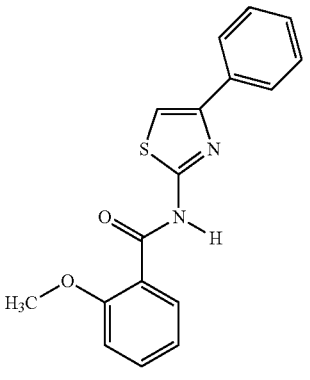 [SMILES: COc1ccccc1C(=O)Nc1nc(-c2ccccc2)cs1] |
| 77 | 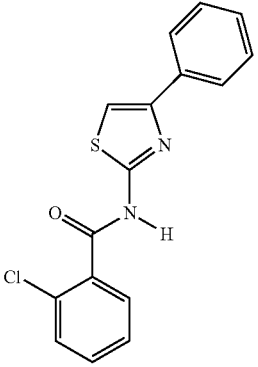 [SMILES: O=C(Nc1nc(-c2ccccc2)cs1)c1ccccc1Cl] |
| 78 | 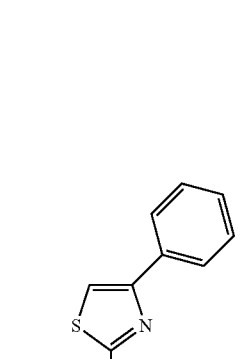 |
| 79 | 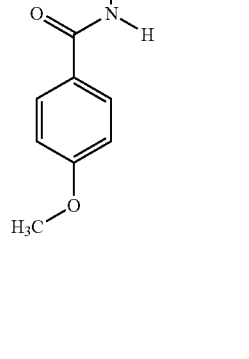 |

TABLE 1-continued
| Cmpd # | Compound |
|---|---|
| 80 | |
| 81 | 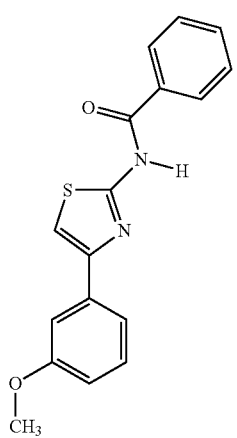 [SMILES: COc1cccc(-c2csc(NC(=O)c3ccccc3)n2)c1] |
| 82 | 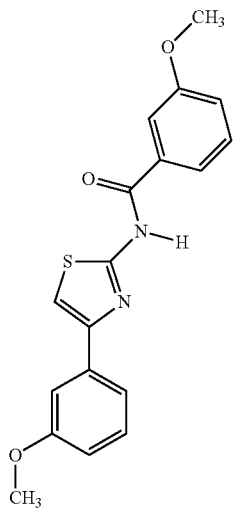 [SMILES: COc1cccc(C(=O)Nc2nc(-c3cccc(OC)c3)cs2)c1] |
TABLE 1-continued
| Cmpd # | Compound |
|---|---|
| 83 | |
| 84 | |
| 85 | |
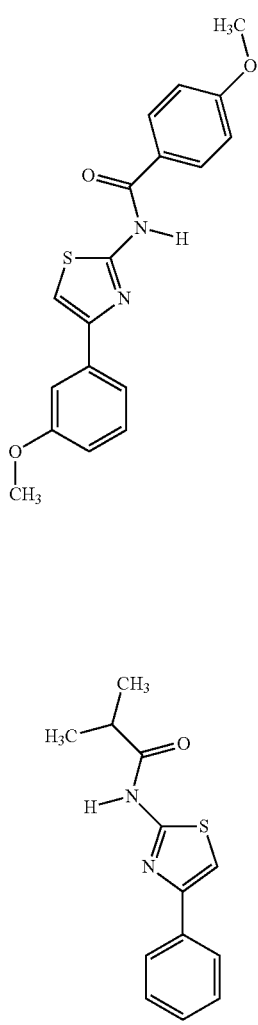

TABLE 1-continued
| Cmpd # | Compound |
|---|---|
| 86 | 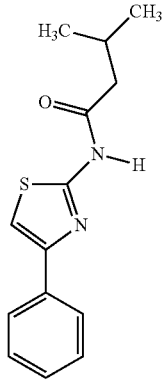 [SMILES: CC(C)CC(=O)Nc1nc(-c2ccccc2)cs1] |
| 87 | 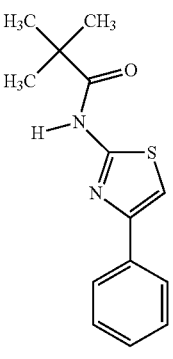 [SMILES: CC(C)(C)C(=O)Nc1nc(-c2ccccc2)cs1] |
| 88 | 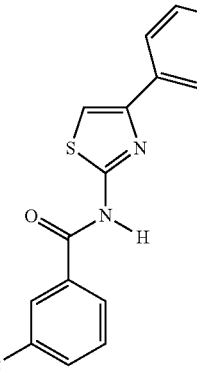 |
| 89 | 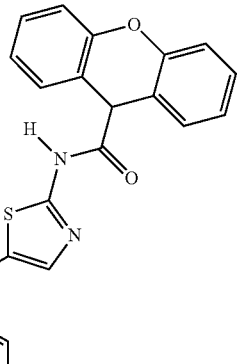 |
| 90 | 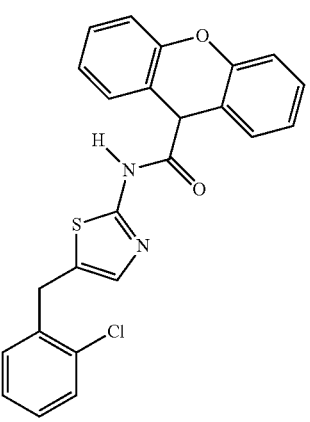 [SMILES: O=C(Nc1ncc(Cc2ccccc2Cl)s1)C1c2ccccc2Oc2ccccc21] |
| 91 | 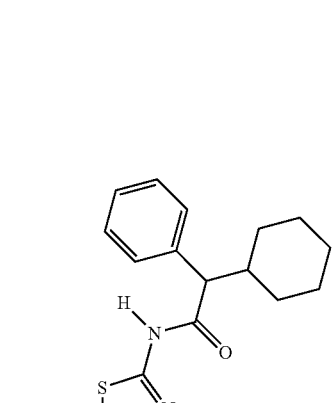 |
| 92 | 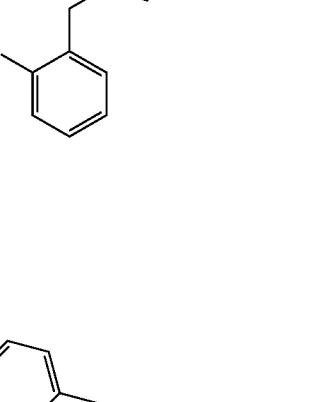 |

TABLE 1-continued
| Cmpd # | Compound |
|---|---|
| 93 | 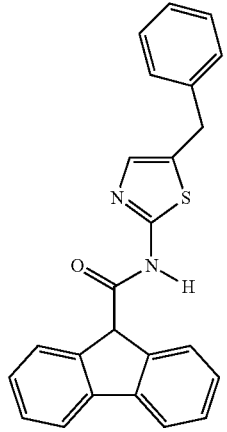 [SMILES: O=C(Nc1ncc(Cc2ccccc2)s1)C1c2ccccc2-c2ccccc21] |
| 95 | 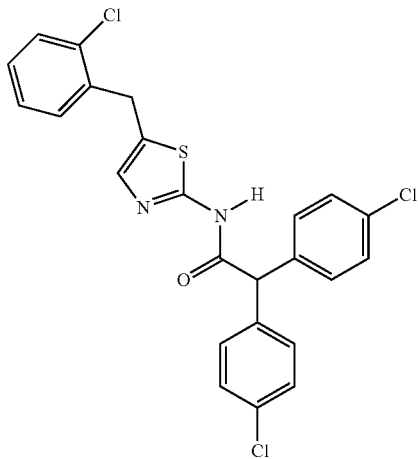 [SMILES: O=C(Nc1ncc(Cc2ccccc2Cl)s1)C(c1ccc(Cl)cc1)c1ccc(Cl)cc1] |
| 96 | 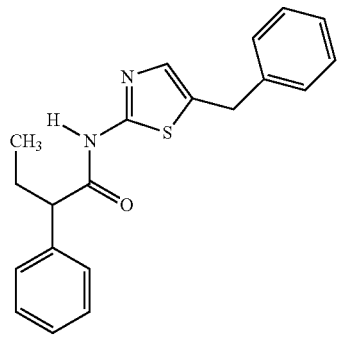 [SMILES: CCC(C(=O)Nc1ncc(Cc2ccccc2)s1)c1ccccc1] |
TABLE 1-continued
| Cmpd # | Compound |
|---|---|
| 97 | 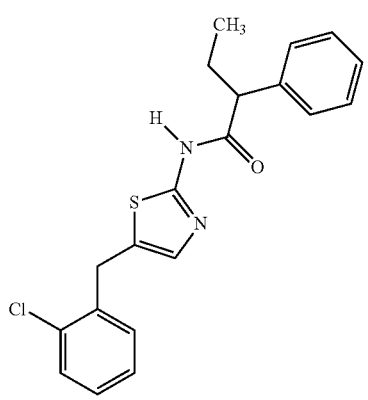 |
| 98 | 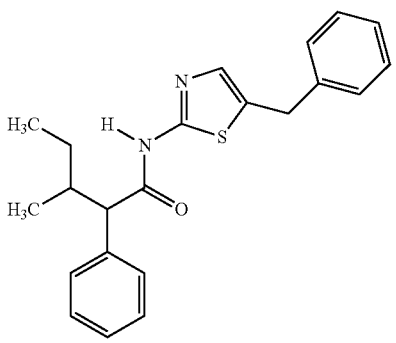 [SMILES: CCC(C)C(C(=O)Nc1ncc(Cc2ccccc2)s1)c1ccccc1] |
| 99 | 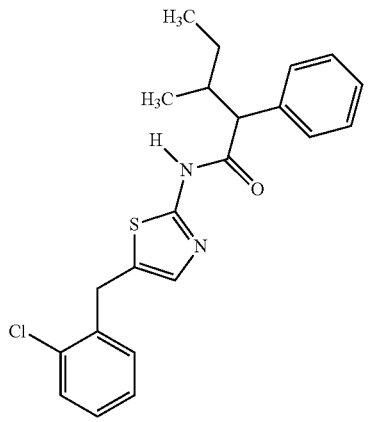 [SMILES: CCC(C)C(C(=O)Nc1ncc(Cc2ccccc2Cl)s1)c1ccccc1] |
| 100 | 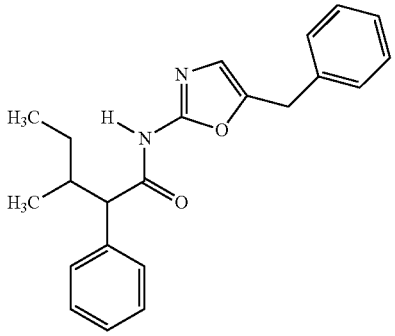 [SMILES: CCC(C)C(C(=O)Nc1ncc(Cc2ccccc2)o1)c1ccccc1] |

TABLE 1-continued
| Cmpd # | Compound |
|---|---|
| 101 | 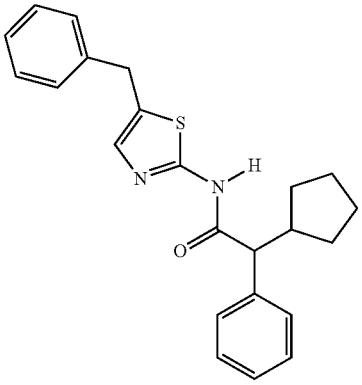 [SMILES: O=C(Nc1ncc(Cc2ccccc2)s1)C(c1ccccc1)C1CCCC1] |
| 102 | 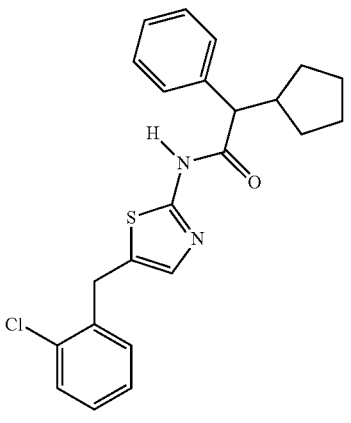 |
| 103 | 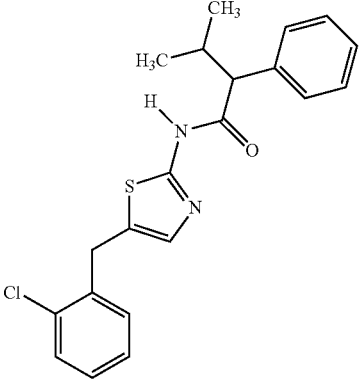 [SMILES: CC(C)C(C(=O)Nc1ncc(Cc2ccccc2Cl)s1)c1ccccc1] |
| 104 | 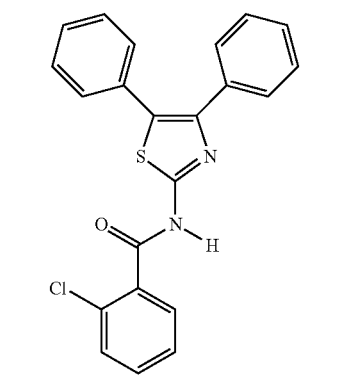 [SMILES: O=C(Nc1nc(-c2ccccc2)c(-c2ccccc2)s1)c1ccccc1Cl] |
TABLE 1-continued
| Cmpd # | Compound |
|---|---|
| 105 | 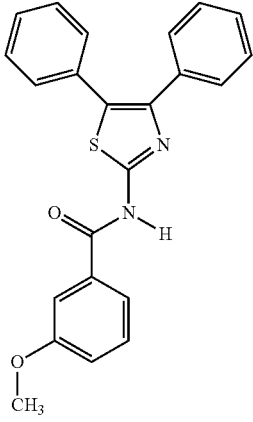 [SMILES: COc1cccc(C(=O)Nc2nc(-c3ccccc3)c(-c3ccccc3)s2)c1] |
| 106 | 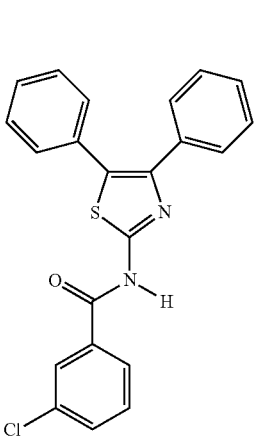 [SMILES: O=C(Nc1nc(-c2ccccc2)c(-c2ccccc2)s1)c1cccc(Cl)c1] |
| 107 | 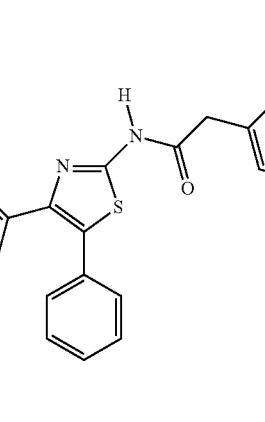 |
| 108 | 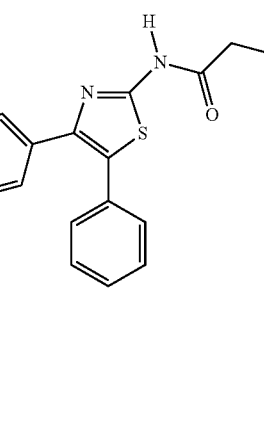 |

TABLE 1-continued

| Cmpd # | Compound |
|---|---|
| 109 | N-(4,5-diphenylthiazol-2-yl)isobutyramide |
| 110 | N-(4,5-diphenylthiazol-2-yl)-3-methylbutanamide |
| 111 | N-(4,5-diphenylthiazol-2-yl)cyclopropanecarboxamide |
| 112 | N-(4,5-diphenylthiazol-2-yl)pivalamide |
| 113 | N-(4,5-diphenylthiazol-2-yl)cyclopentanecarboxamide |
| 114 | N-(4,5-diphenylthiazol-2-yl)cyclohexanecarboxamide |
| 115 | N-(4,5-diphenylthiazol-2-yl)tetrahydrofuran-2-carboxamide |
| 116 | N-(4,5-diphenylthiazol-2-yl)tetrahydrofuran-3-carboxamide |
| 117 | 2-cyclohexyl-N-(5-(4-chlorobenzyl)thiazol-2-yl)-2-phenylacetamide |

TABLE 1-continued
| Cmpd # | Compound |
|---|---|
| 118 | 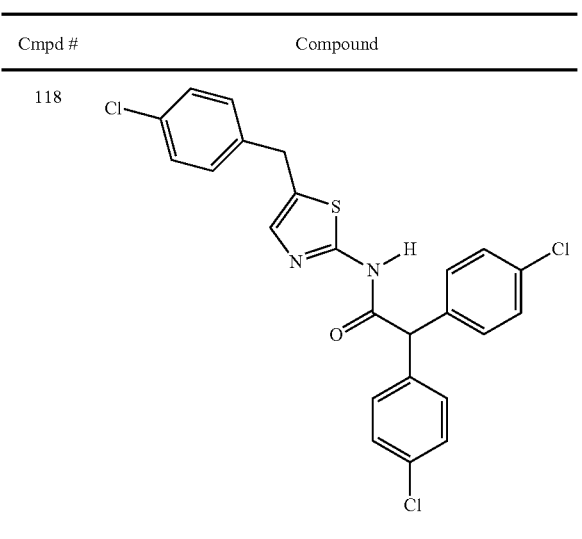 |
| 119 | 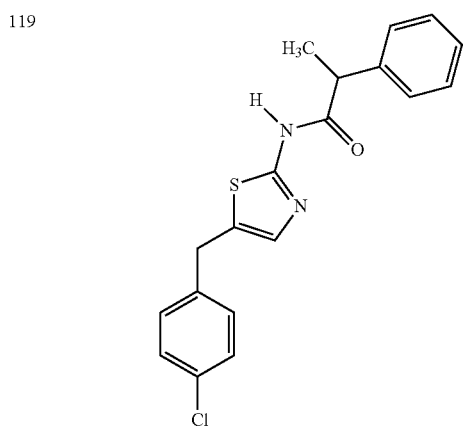 |
| 120 | 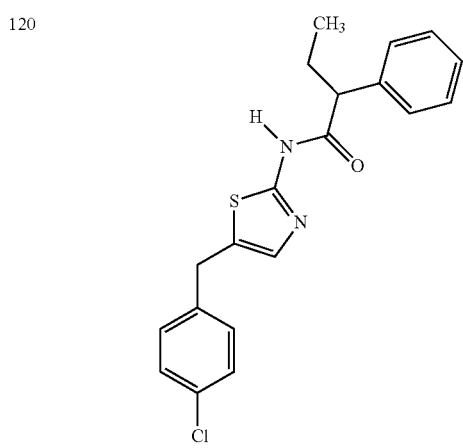 |
TABLE 1-continued
| Cmpd # | Compound |
|---|---|
| 121 | 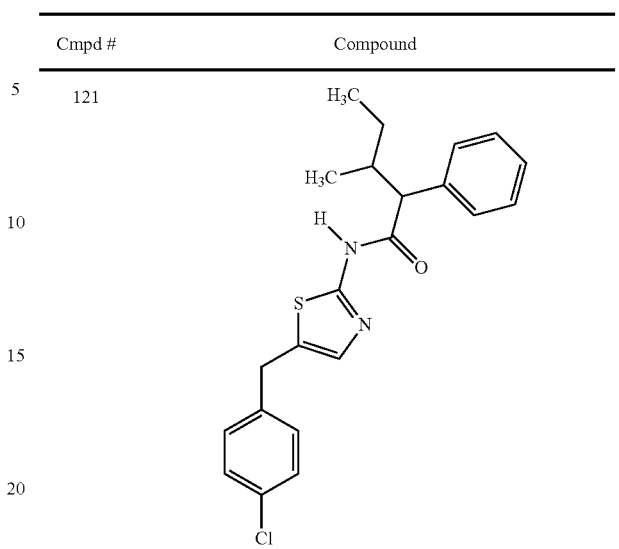 |
| 122 | 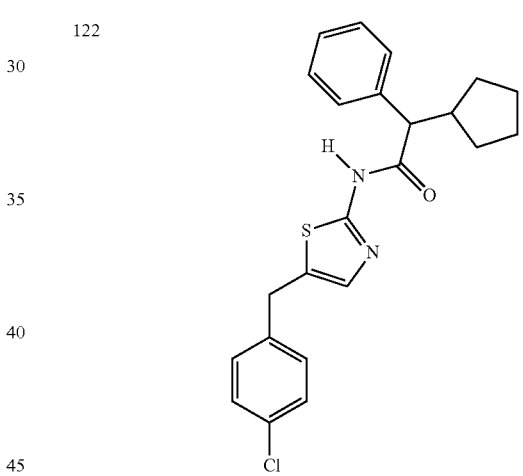 |
| 123 | 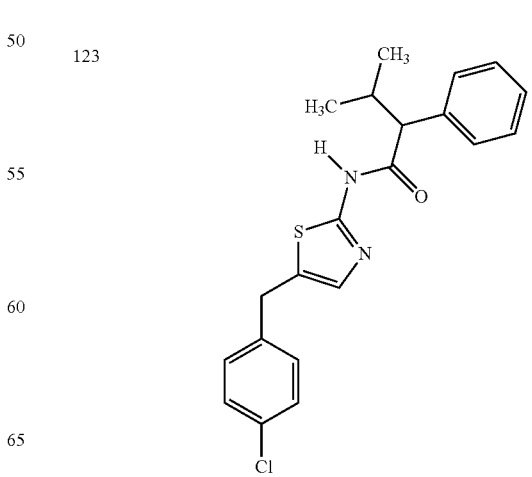 |

TABLE 1-continued

| Cmpd # | Compound |
|---|---|
| 124 | |
| 125 | |
| 126 | |
| 127 | |
| 128 | |
| 129 | |
| 130 | |

TABLE 1-continued
| Cmpd # | Compound |
|---|---|
| 131 | 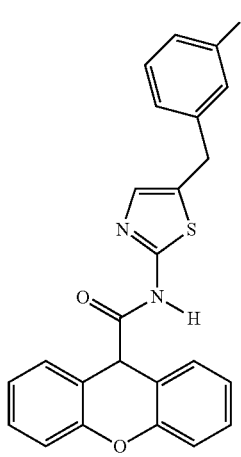 |
| 132 | 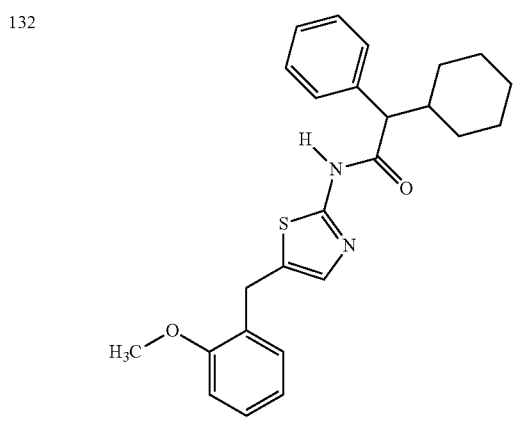 |
| 133 | 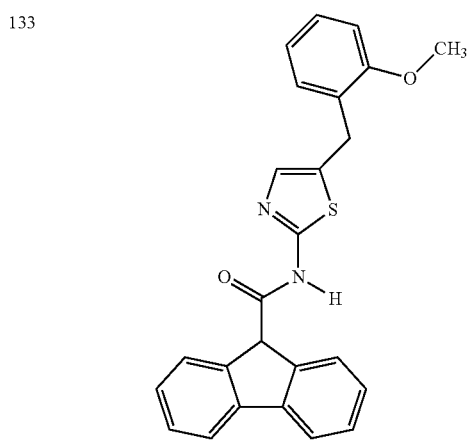 |
TABLE 1-continued
| Cmpd # | Compound |
|---|---|
| 134 | 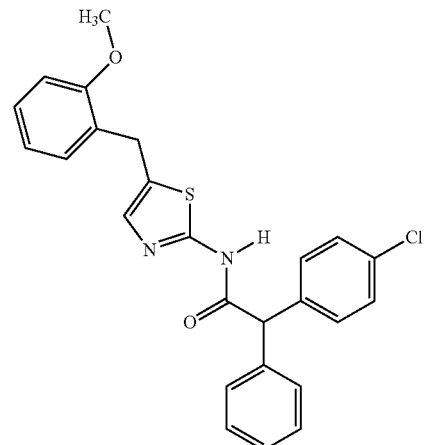 |
| 135 | 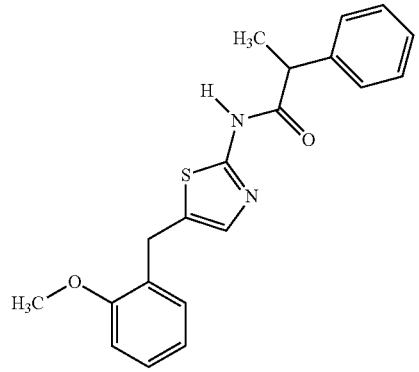 |
| 136 | 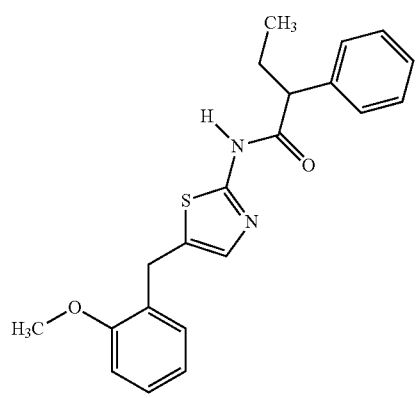 |

TABLE 1-continued

| Cmpd # | Compound |
|---|---|
| 137 | (structure) |
| 138 | (structure) |
| 139 | (structure) |
| 140 | (structure) |
| 141 | (structure) |
| 142 | (structure) |
| 143 | (structure) |
| 145 | (structure) |

TABLE 1-continued
| Cmpd # | Compound |
|---|---|
| 146 | 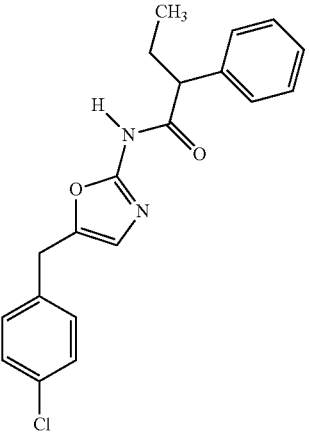 [SMILES: CCC(C(=O)Nc1ncc(Cc2ccc(Cl)cc2)o1)c1ccccc1] |
| 147 | 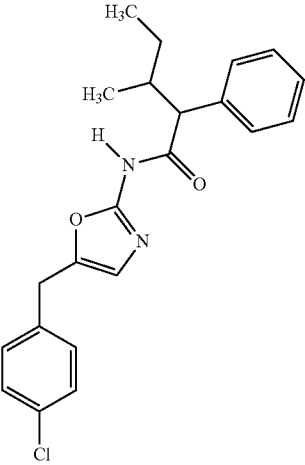 [SMILES: CCC(C)C(C(=O)Nc1ncc(Cc2ccc(Cl)cc2)o1)c1ccccc1] |
| 148 | 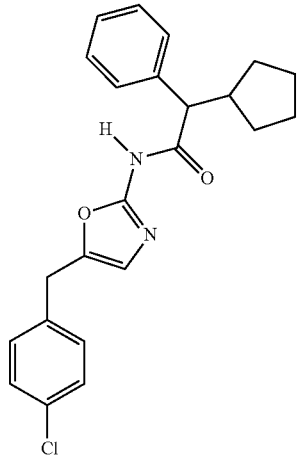 [SMILES: O=C(Nc1ncc(Cc2ccc(Cl)cc2)o1)C(c1ccccc1)C1CCCC1] |
| 149 | 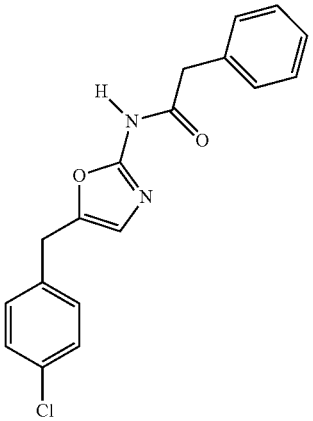 [SMILES: O=C(Cc1ccccc1)Nc1ncc(Cc2ccc(Cl)cc2)o1] |
| 150 | 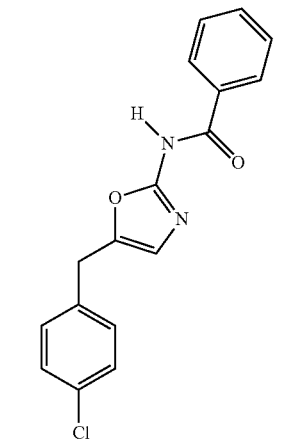 [SMILES: O=C(Nc1ncc(Cc2ccc(Cl)cc2)o1)c1ccccc1] |
| 151 | 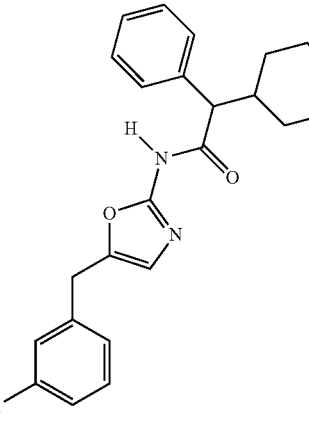 |
| 152 | 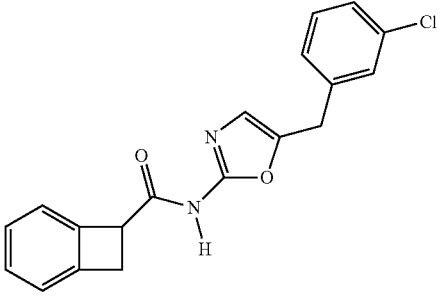 [SMILES: O=C(Nc1ncc(Cc2cccc(Cl)c2)o1)C1Cc2ccccc21] |

TABLE 1-continued

| Cmpd # | Compound |
|---|---|
| 153 | (structure) |
| 154 | (structure) |
| 155 | (structure) |
| 156 | (structure) |
| 157 | (structure) |
| 158 | (structure) |
| 159 | (structure) |

TABLE 1-continued
| Cmpd # | Compound |
|---|---|
| 160 | 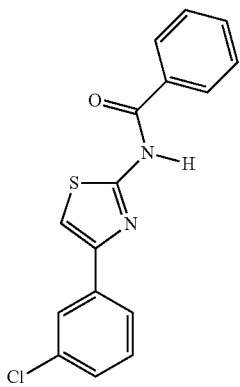 [SMILES: O=C(Nc1nc(-c2cccc(Cl)c2)cs1)c1ccccc1] |
| 161 | 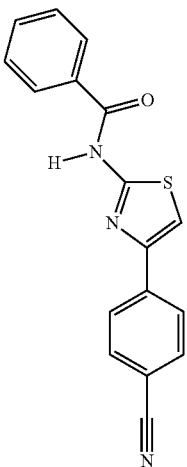 [SMILES: N#Cc1ccc(-c2csc(NC(=O)c3ccccc3)n2)cc1] |
| 162 | 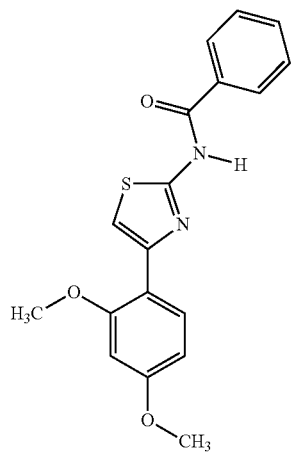 [SMILES: COc1ccc(-c2csc(NC(=O)c3ccccc3)n2)c(OC)c1] |
TABLE 1-continued
| Cmpd # | Compound |
|---|---|
| 163 | 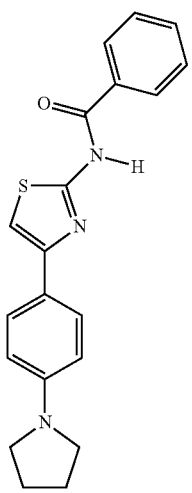 [SMILES: O=C(Nc1nc(-c2ccc(N3CCCC3)cc2)cs1)c1ccccc1] |
| 164 | 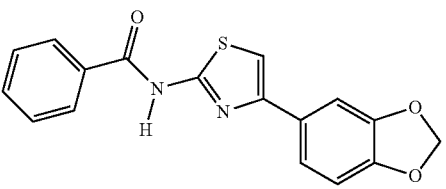 [SMILES: O=C(Nc1nc(-c2ccc3c(c2)OCO3)cs1)c1ccccc1] |
| 165 | 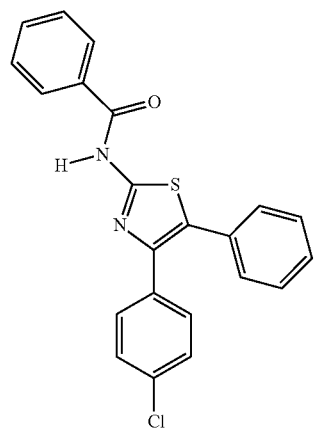 [SMILES: O=C(Nc1nc(-c2ccc(Cl)cc2)c(-c2ccccc2)s1)c1ccccc1] |
| 166 | 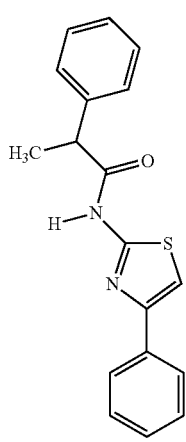 [SMILES: CC(C(=O)Nc1nc(-c2ccccc2)cs1)c1ccccc1] |

TABLE 1-continued
| Cmpd # | Compound |
|---|---|
| 167 | 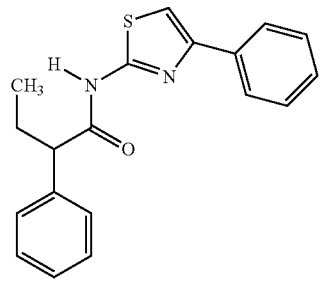 [SMILES: CCC(C(=O)Nc1nc(-c2ccccc2)cs1)c1ccccc1] |
| 168 | 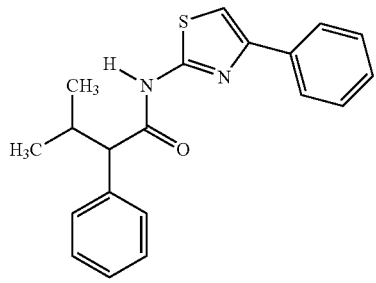 [SMILES: CC(C)C(C(=O)Nc1nc(-c2ccccc2)cs1)c1ccccc1] |
| 169 | 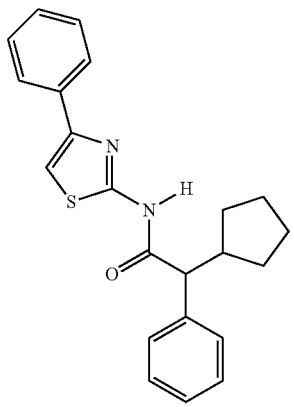 [SMILES: O=C(Nc1nc(-c2ccccc2)cs1)C(c1ccccc1)C1CCCC1] |
| 170 | 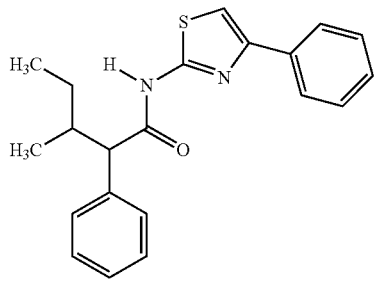 [SMILES: CCC(C)C(C(=O)Nc1nc(-c2ccccc2)cs1)c1ccccc1] |
TABLE 1-continued
| Cmpd # | Compound |
|---|---|
| 171 | 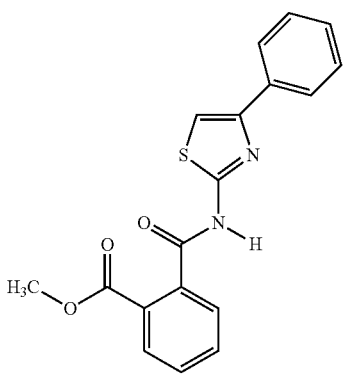 [SMILES: COC(=O)c1ccccc1C(=O)Nc1nc(-c2ccccc2)cs1] |
| 172 | 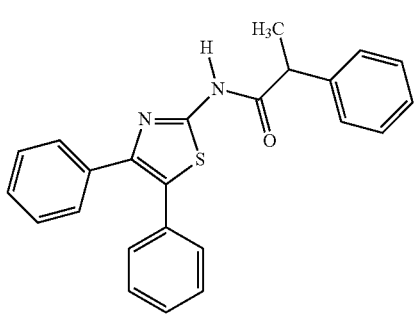 [SMILES: CC(C(=O)Nc1nc(-c2ccccc2)c(-c2ccccc2)s1)c1ccccc1] |
| 173 | 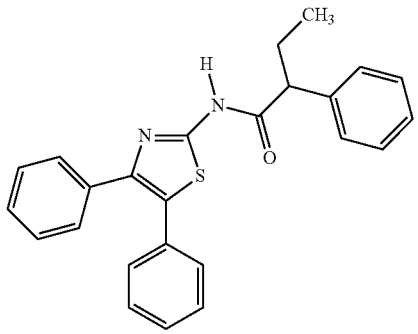 [SMILES: CCC(C(=O)Nc1nc(-c2ccccc2)c(-c2ccccc2)s1)c1ccccc1] |
| 174 | 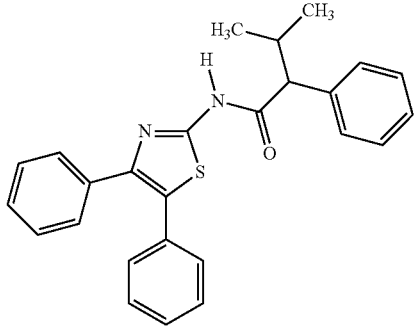 [SMILES: CC(C)C(C(=O)Nc1nc(-c2ccccc2)c(-c2ccccc2)s1)c1ccccc1] |

TABLE 1-continued

| Cmpd # | Compound |
|---|---|
| 175 | |
| 176 | |
| 177 | |
| 178 | |
| 179 | |
| 180 | |
| 181 | |
| 182 | |

TABLE 1-continued

| Cmpd # | Compound |
|---|---|
| 183 | |
| 184 | |
| 185 | |
| 186 | |
| 187 | |
| 188 | |
| 189 | |
| 190 | |

TABLE 1-continued
| Cmpd # | Compound |
|---|---|
| 191 | 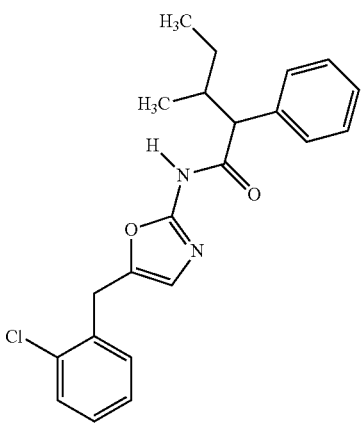 |
| 192 | 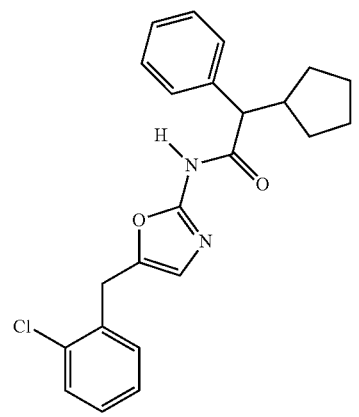 [SMILES: O=C(Nc1ncc(Cc2ccccc2Cl)o1)C(c1ccccc1)C1CCCC1] |
| 193 | 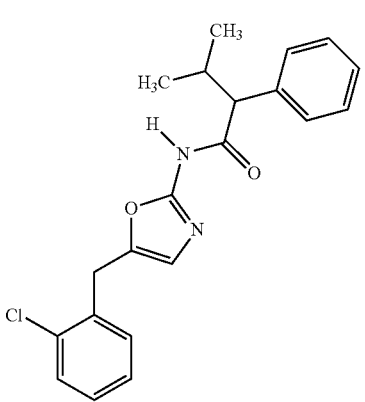 [SMILES: CC(C)C(C(=O)Nc1ncc(Cc2ccccc2Cl)o1)c1ccccc1] |
TABLE 1-continued
| Cmpd # | Compound |
|---|---|
| 194 | 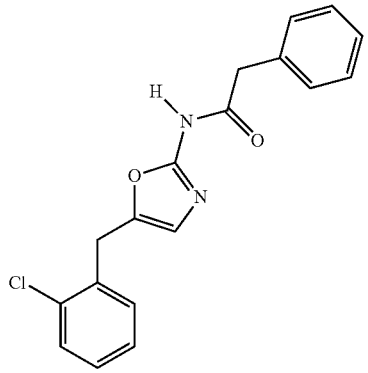 [SMILES: O=C(Cc1ccccc1)Nc1ncc(Cc2ccccc2Cl)o1] |
| 195 | 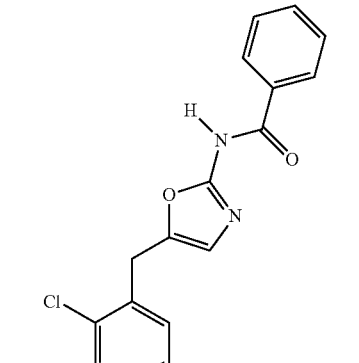 |
| 196 | 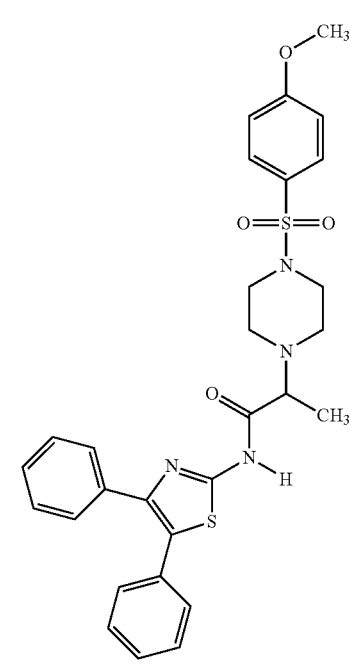 [SMILES: COc1ccc(S(=O)(=O)N2CCN(C(C)C(=O)Nc3nc(-c4ccccc4)c(-c4ccccc4)s3)CC2)cc1] |

TABLE 1-continued
| Cmpd # | Compound |
|---|---|
| 197 | 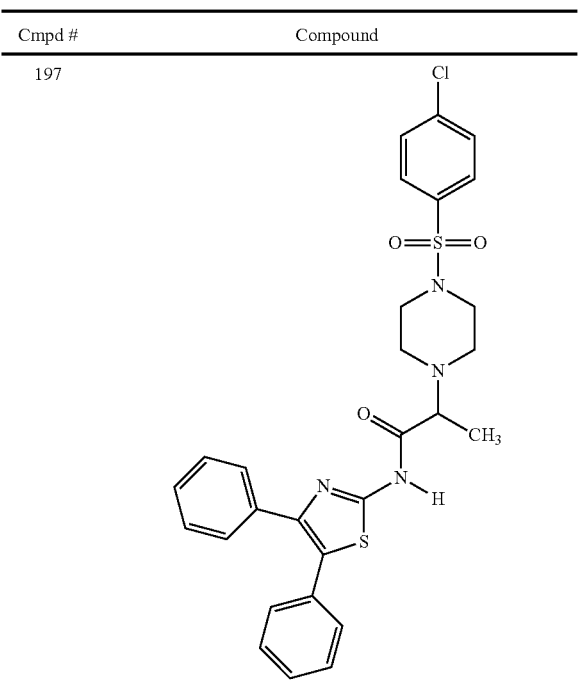 |
| 198 | 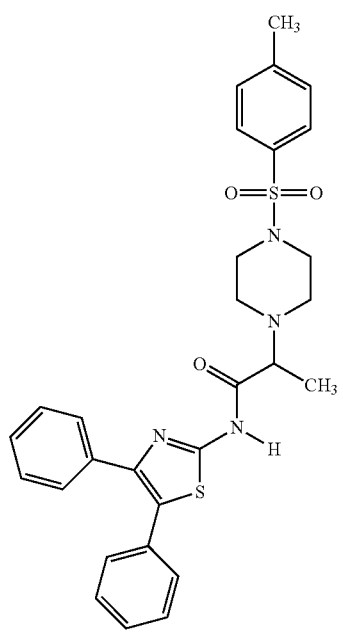 [SMILES: Cc1ccc(S(=O)(=O)N2CCN(C(C)C(=O)Nc3nc(-c4ccccc4)c(-c4ccccc4)s3)CC2)cc1] |
TABLE 1-continued
| Cmpd # | Compound |
|---|---|
| 199 | 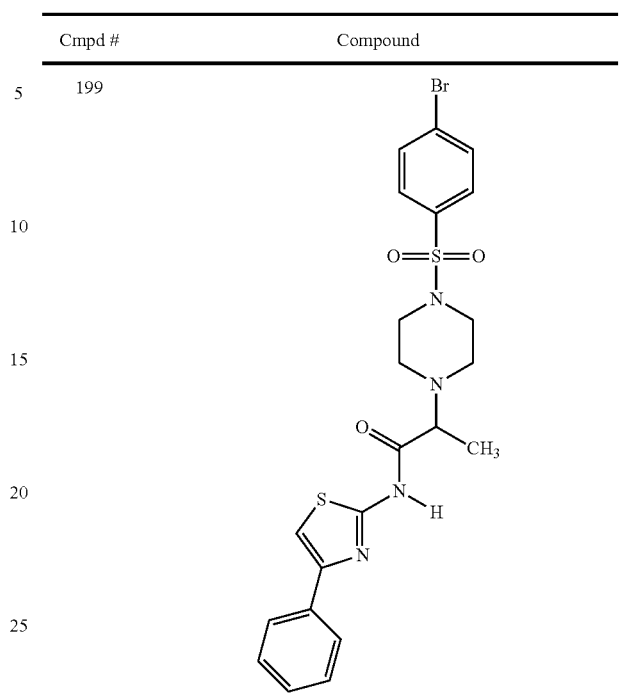 |
| 201 | 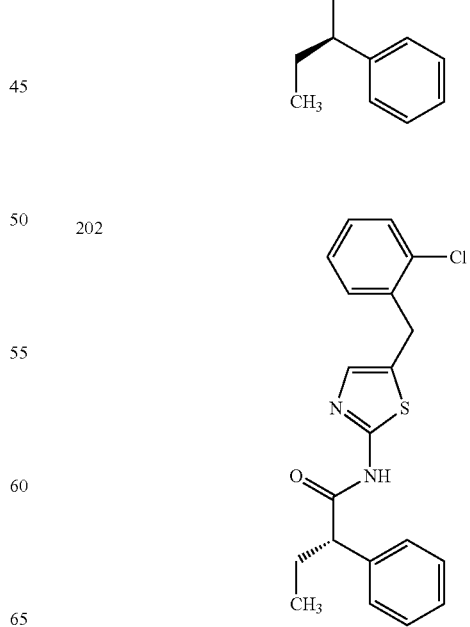 |
| 202 | |

TABLE 1-continued

| Cmpd # | Compound |
|---|---|
| 203 | (5-(3-chlorobenzyl)thiazol-2-yl)-NH-C(=O)-CH(CH₂CH₃)-phenyl (S) |
| 204 | (5-(3-chlorobenzyl)thiazol-2-yl)-NH-C(=O)-CH(CH₂CH₃)-phenyl (R) |
| 205 | (5-(4-chlorobenzyl)thiazol-2-yl)-NH-C(=O)-CH(CH₂CH₃)-phenyl (S) |
| 206 | N-(5-(2-chlorobenzyl)thiazol-2-yl)-3-methylbutanamide |
| 207 | N-(5-(2-chlorobenzyl)thiazol-2-yl)cyclopropanecarboxamide |
| 208 | N-(5-(2-chlorobenzyl)thiazol-2-yl)propanamide |
| 209 | N-(5-(2-chlorobenzyl)thiazol-2-yl)cyclopentanecarboxamide |

TABLE 1-continued
| Cmpd # | Compound |
|---|---|
| 210 | 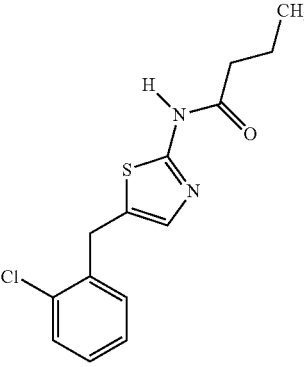 |
| 211 | 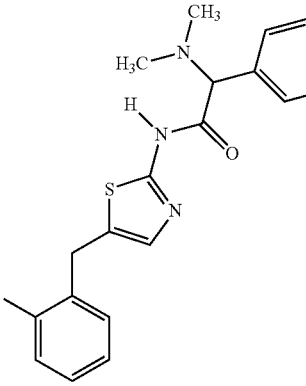 |
| 212 | 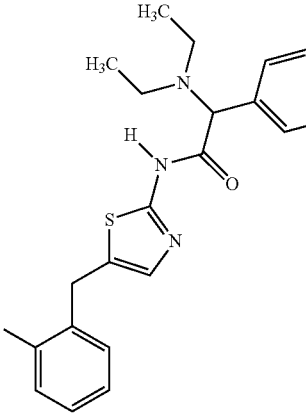 |
| 213 | 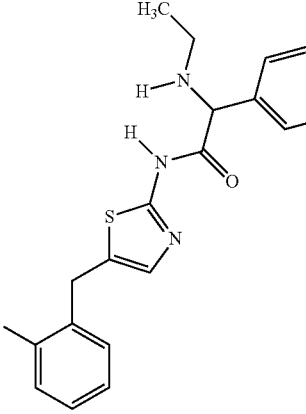 |
| 214 | 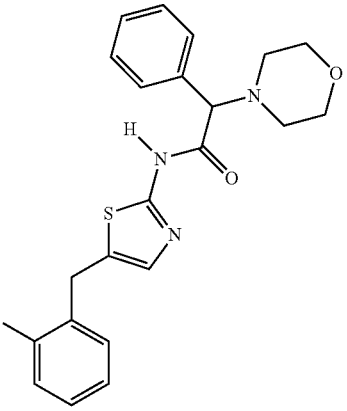 |
| 215 | 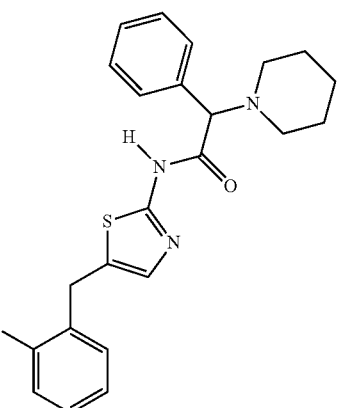 |
| 216 | 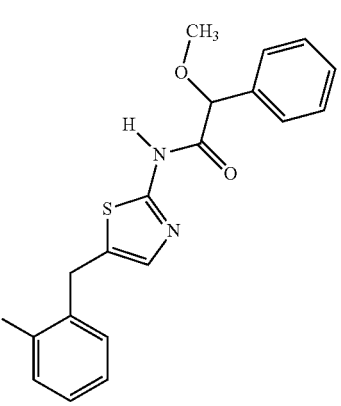 |
| 217 | 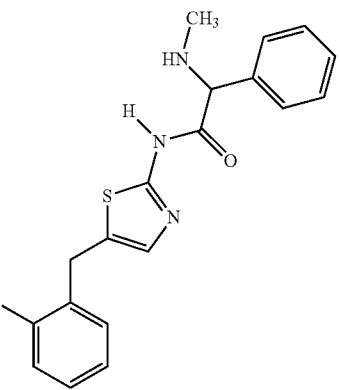 |

TABLE 1-continued

| Cmpd # | Compound |
|---|---|
| 218 | 2-(methylamino)butanamide, N-(5-(2-chlorobenzyl)thiazol-2-yl) |
| 219 | 2-methoxybutanamide, N-(5-(2-chlorobenzyl)thiazol-2-yl) |
| 220 | 2-(ethylamino)butanamide, N-(5-(2-chlorobenzyl)thiazol-2-yl) |
| 221 | 2-(diethylamino)butanamide, N-(5-(2-chlorobenzyl)thiazol-2-yl) |
| 222 | 2-(dimethylamino)butanamide, N-(5-(2-chlorobenzyl)thiazol-2-yl) |
| 223 | 2-morpholinobutanamide, N-(5-(2-chlorobenzyl)thiazol-2-yl) |
| 224 | 2-thiomorpholinobutanamide, N-(5-(2-chlorobenzyl)thiazol-2-yl) |
| 225 | 2-(piperidin-1-yl)butanamide, N-(5-(2-chlorobenzyl)thiazol-2-yl) |

TABLE 1-continued
| Cmpd # | Compound |
|---|---|
| 226 | 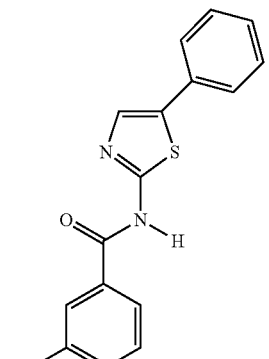 |
| 227 | |
| 228 | |
TABLE 1-continued
| Cmpd # | Compound |
|---|---|
| 229 | 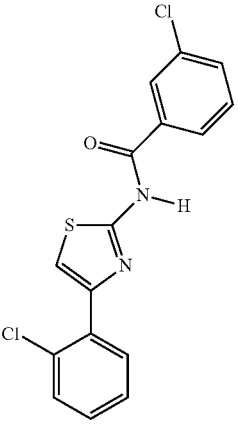 [SMILES: O=C(Nc1nc(-c2ccccc2Cl)cs1)c1cccc(Cl)c1] |
| 230 | |
| 231 | |

TABLE 1-continued
| Cmpd # | Compound |
|---|---|
| 232 | 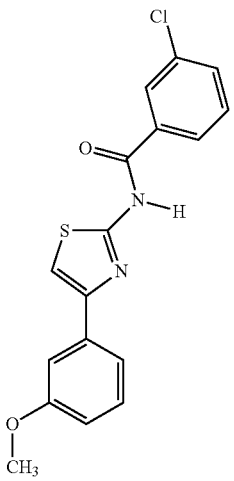 [SMILES: COc1cccc(-c2csc(NC(=O)c3cccc(Cl)c3)n2)c1] |
| 233 | |
| 234 | |
| 235 | |
| 237 | |
| 238 | |

TABLE 1-continued

| Cmpd # | Compound |
|---|---|
| 239 | |
| 240 | |
| 241 | |
| 242 | |
| 243 | |
| 244 | |

TABLE 1-continued
| Cmpd # | Compound |
|---|---|
| 245 | 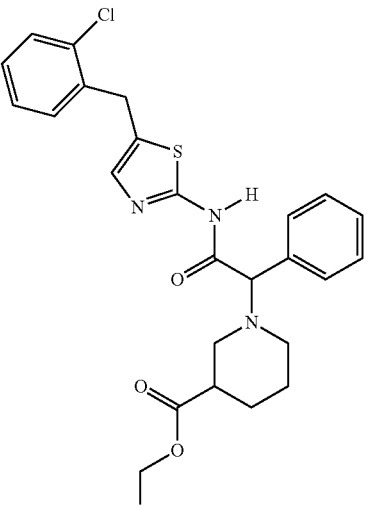 |
| 246 | 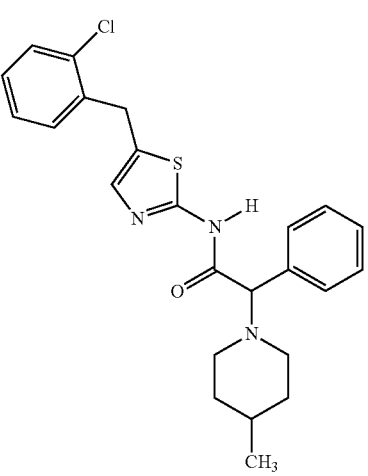 [SMILES: CC1CCN(C(C(=O)Nc2ncc(Cc3ccccc3Cl)s2)c2ccccc2)CC1] |
| 247 | 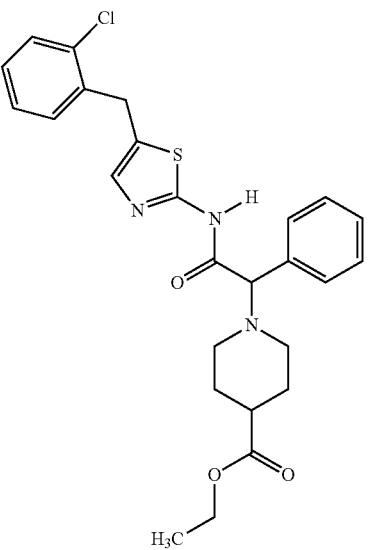 [SMILES: CCOC(=O)C1CCN(C(C(=O)Nc2ncc(Cc3ccccc3Cl)s2)c2ccccc2)CC1] |"
TABLE 1-continued
| Cmpd # | Compound |
|---|---|
| 248 | 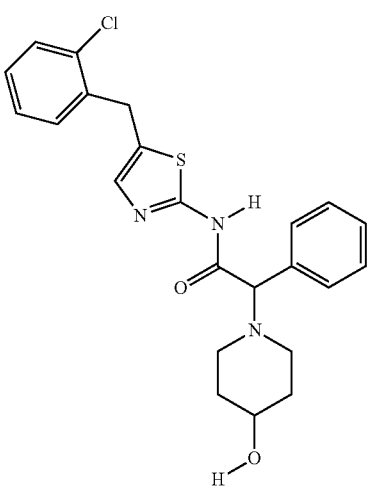 [SMILES: O=C(Nc1ncc(Cc2ccccc2Cl)s1)C(c1ccccc1)N1CCC(O)CC1] |
| 249 | 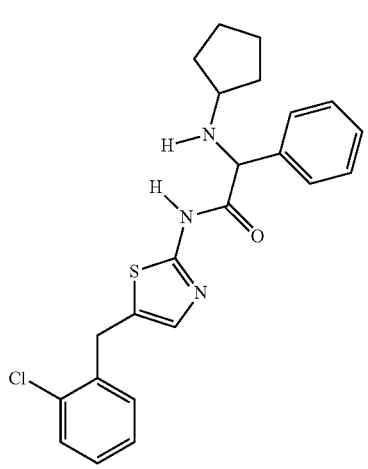 [SMILES: O=C(Nc1ncc(Cc2ccccc2Cl)s1)C(NC1CCCC1)c1ccccc1] |
| 250 | |

TABLE 1-continued
| Cmpd # | Compound |
|---|---|
| 251 | 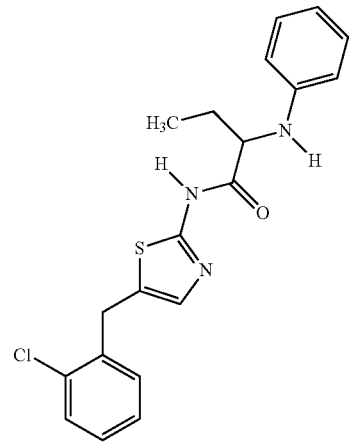 [SMILES: CCC(Nc1ccccc1)C(=O)Nc1ncc(Cc2ccccc2Cl)s1] |
| 252 | 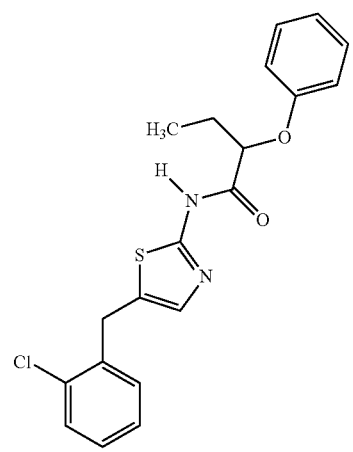 [SMILES: CCC(Oc1ccccc1)C(=O)Nc1ncc(Cc2ccccc2Cl)s1] |
| 253 | 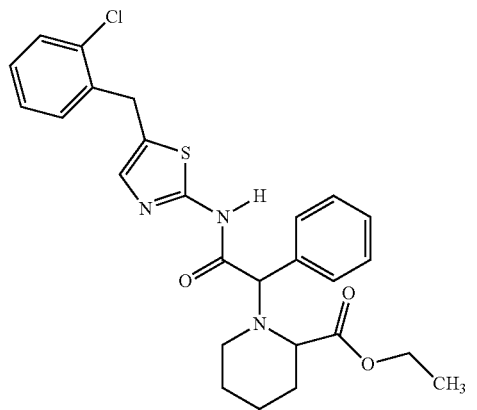 [SMILES: CCOC(=O)C1CCCCN1C(C(=O)Nc1ncc(Cc2ccccc2Cl)s1)c1ccccc1] |
| 254 | 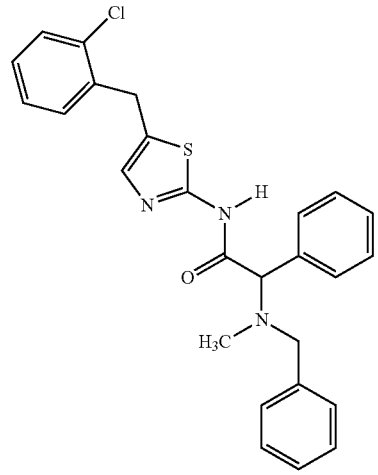 [SMILES: CN(Cc1ccccc1)C(C(=O)Nc1ncc(Cc2ccccc2Cl)s1)c1ccccc1] |
| 255 | 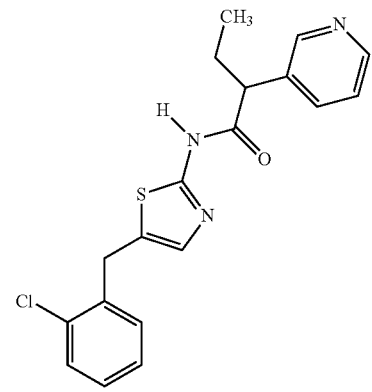 |
| 256 | 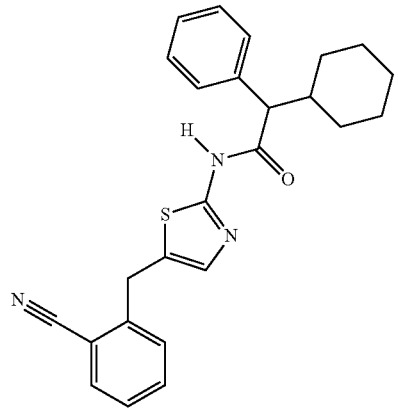 [SMILES: N#Cc1ccccc1Cc1cnc(NC(=O)C(c2ccccc2)C2CCCCC2)s1] |

TABLE 1-continued

| Cmpd # | Compound |
|---|---|
| 257 | |
| 258 | |
| 259 | |
| 260 | |
| 261 | |
| 262 | |
| 263 | |
| 264 | |

TABLE 1-continued

| Cmpd # | Compound |
|---|---|
| 265 | 6-ethoxy-benzothiazol-2-yl 2-phenylbutanamide |
| 266 | 6-methoxy-benzothiazol-2-yl 2-phenylbutanamide |
| 267 | 5,6-dimethyl-benzothiazol-2-yl 2-phenylbutanamide |
| 268 | 7-methyl-benzothiazol-2-yl 2-phenylbutanamide |
| 269 | methyl 3-phenyl-4-oxo-4-[5-(2-chlorobenzyl)thiazol-2-ylamino]butanoate |
| 270 | N-[5-(2-chlorobenzyl)thiazol-2-yl] 2-(4-methoxyphenyl)butanamide |
| 271 | N-[5-(2-chlorobenzyl)thiazol-2-yl] 3-phenylbutanamide |
| 272 | N-[5-(2-chlorobenzyl)thiazol-2-yl] 2-(dimethylamino)-3-phenylpropanamide |
| 273 | N-[5-(2-methoxybenzyl)thiazol-2-yl] 2-(4-methoxyphenyl)butanamide |
| 274 | N-[5-(2-methoxybenzyl)thiazol-2-yl] 3-phenylbutanamide |

TABLE 1-continued

| Cmpd # | Compound |
|---|---|
| 275 | |
| 276 | |
| 277 | |
| 278 | |
| 279 | |
| 280 | |
| 281 | |
| 282 | |
| 283 | |

TABLE 1-continued

| Cmpd # | Compound |
|---|---|
| 284 | (structure) |
| 285 | (structure) |
| 286 | (structure) |
| 287 | (structure) |
| 288 | (structure) |
| 289 | (structure) |

According to an alternative embodiment, preferred compounds of the present invention are those that measurably increase the activity of an ABC-transporter or of a fragment thereof, and preferably CFTR activity.

According to another alternative embodiment, preferred compounds of the present invention are those that measurably decrease the activity of an ABC-transporter or of a fragment thereof.

One of skill in the art would be well aware of techniques and assays useful in measuring the increase or decrease of activity of an ABC-transporter or of a fragment thereof.

According to an alternative preferred embodiment, the present invention provides a method of modulating CFTR activity in a cell membrane of a mammal in need thereof, comprising the step of administering to said mammal a composition comprising a compound of the present invention as defined above.

The preferred embodiments of compound of formula (I) useful in potentiating the activity of CFTR include the preferred embodiments of the present invention described above.

According to an alternative embodiment, the present invention provides a method of increasing the number of functional ABC transporters in a membrane of a cell, comprising the step of contacting said cell with a compound of the present invention. The term "functional ABC transporter" as used herein means an ABC transporter that is capable of transport activity.

According to a preferred embodiment, said functional ABC transporter is CFTR.

The preferred embodiments of compounds of formula (I) useful in increasing the number of functional ABC transporters include preferred embodiments of the compounds of the present invention as described above.

Unless otherwise stated, structures depicted, herein are also meant to include all stereochemical forms of the structure i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in. the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The compounds of the present invention may be readily prepared using methods known in the art. One such synthetic route is illustrated in Scheme 1 below:

Scheme 1

Step 1:

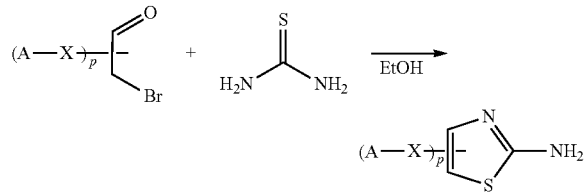

2-Aminothiazoles. The appropriate bromoketone was dissolved in a minimum of ethanol or methanol with 1.1 equivalents of thiourea. The reaction mixture was stirred overnight at room temperature, evaporated to dryness, and then dissolved in either dichloromethane or ethyl acetate. The reaction mixture was then extracted with 1M sodium hydroxide followed by a saturated aqueous sodium chloride solution. The organic layer was then separated, dried over sodium sulfate, and evaporated to dryness to yield the desired 2-aminothiazole.

Step 2:

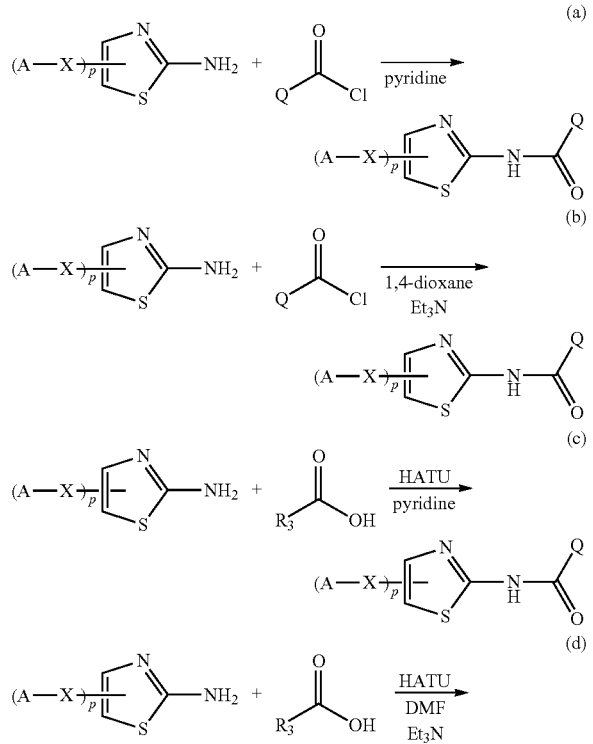

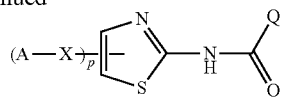

Amides. (a) If the appropriate acid chloride was commercially available, it was added to one equivalent of the appropriate amine in minimum of pyridine. The reaction mixture was allowed to stir overnight at room temperature. The reaction mixture was then filtered and evaporated to dryness. The crude product was purified by reverse phase preparative liquid chromatography.

(b) Alternatively, the acid chloride was added to one equivalent of the appropriate amine in minimum of 1,4-dioxane containing an excess of triethylamine. The reaction mixture was then either allowed to stir overnight at room temperature or subjected to microwave irradiation for 5 minutes at 200° C. The crude product was then filtered, evaporated to dryness, dissolved in a minimum of dimethylsulfoxide and then purified by reverse phase preparative liquid chromatography.

(c) If the appropriate acid chloride was not commercially available the appropriate carboxylic acid was added to a solution containing one equivalent of the appropriate amine in a minimum of pyridine. O-(7-Azabenzotriazol-1-yl)-N,N,N',N'-tetramethyluronium hexafluorophosphate (HATU, 1.4 eq.) is added, and the reaction is stirred overnight. The crude product was purified by reverse phase preparative liquid chromatography.

(d) If the appropriate acid chloride was not commercially available the appropriate carboxylic acid was added to a solution containing one equivalent of the appropriate amine in a minimum of N,N-dimethylformamide with an excess of triethylamine. O-(7-Azabenzotriazol-1-yl)-N,N,N',N'-tetramethyluronium hexafluorophosphate (HATU, 1.4 eq.) is added, and the reaction is stirred overnight. The crude product was purified by reverse phase preparative liquid chromatography.

One of skill in the art will recognize that the above two synthetic routes are generic and can be readily exploited for any embodiment of compound formula (I).

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to an alternative embodiment, the present invention provides a method of treating a ABC transporter mediated disease in a mammal, comprising the step of administering to said mammal a composition comprising a compound of the present invention, or a preferred embodiment thereof as set forth above.

According to a preferred embodiment, the ABC transporter mediated disease is selected from immunodeficiency disorder, inflammatory disease, allergic disease, autoimmune disease, destructive bone disorder, proliferative disorder, infectious disease or viral disease.

In certain preferred embodiments, the present invention provides a method of treating cystic fibrosis, hereditary emphysema, hereditary hemochromatosis, coagulation-fibrinolysis deficiencies, such as protein C deficiency, Type-1 hereditary angioedema, lipid processing deficiencies, such as Familial hypercholesterolemia, Type-1 chylomicronemia, abetalipoproteinemia, lysosomal storage diseases, such as I-cell disease/Pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebellar ataxia type I, Spinal and bulbar muscular atrophy, dentatorubal pallidoluysian, and myotonic dystrophy, as well as spongiform encephalopathies, such as hereditary Crentzfeldt-Jakob disease (due to prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of the present invention, or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of any one of the above diseases.

The compounds and compositions, according to the method of the present invention, may be administered using any amount and any route administration effective for treating or lessening the severity of of any one of the above diseases.

In one embodiment, the compounds of the present invention are useful in treating cystic fibrosis.

According to a more preferred embodiment, the disease so treated is selected from Tangier's disease, stargardt disease 1, age related macular dystrophy 2, retinintis pigmentosa, bare lymphocyte syndrome, PFIC-3, anemia, progressive intrahepatic cholestasis-2, Dublin-Johnson syndrome, Pseudoxanthoma elasticum, cystic fibrosis, familial persistent hyperinsulinemic hyproglycemia of infancy, adrenolecukodystrophy, sitosterolemia, chronic obstructive pulmonary disease, asthma, disseminated bronchiectasis, chronic pancreatitis, male infertility, emphysema, or pneumonia.

According to another more preferred embodiment, the ABC transporter mediated disease is secretory diarrhea, or polycystic kidney disease in a mammal.

According to an alternative preferred embodiment, the present invention provides a method of treating cystic fibrosis or secretory diahrrea comprising the step of administering to said mammal a composition comprising the step of administering to said mammal a composition comprising a compound of the present invention, or a preferred embodiment thereof as set forth above. Most preferably, said disease is cystic fibrosis.

According to another embodiment, the present invention provides a method of modulating activity of an anion channel in vitro or in vivo, comprising the step of contacting said channel with a compound of the present invention. Preferably, said anion channel is a chloride channel or a bicarbonate channel. More preferably, said anion channel, is a chloride channel.

According to yet another embodiment, the present invention provides a method of treating an anion channel mediated disease in a mammal, comprising the step of administering to said mammal a composition comprising a compound according to the present invention.

According to another embodiment, the present invention provides a pharmaceutical composition comprising:
 (i) a compound of the present invention as described above;
 (ii) a pharmaceutically acceptable carrier; and
 (iii) an additional agent selected from a mucolytic agent, bronchodialator, an antibiotic, an anti-infective agent, an anti-inflammatory agent, a CFTR modulator, or a nutritional agent.

Preferred embodiments of compounds the present invention in the above pharmaceutical composition are those as described above.

According to another embodiment, the present invention provides a kit for use in measuring the activity of a ABC transporter or a fragment thereof in a biological sample in vitro or in vivo, comprising;
 (i) a composition comprising a compound of the present invention; and
 (ii) instructions for:
   a) contacting the composition with the biological sample;
   b) measuring activity of said ABC transporter or a fragment thereof.

According to a preferred embodiment, the kit is useful in measuring the activity of CFTR.

According to another preferred embodiment, the activity of the ABC transporter is measured by measuring the transmembrane voltage potential.

Means for measuring the voltage potential across a membrane in the biological sample may employ any of the known methods in the art, such as optical membrane potential assay or other electrophysiological methods.

123

The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69 (4): 1272-80, and Gonzalez, J. E. and R. Y. Tsien (1997) "Improved indicators of cell membrane potential that use fluorescence resonance energy transfer" Chem Biol 4 (4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4 (9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

Preferred ABC transporters in the kit of the present invention include CFTR.

In order that the invention described herein may be more fully understood, the following examples are set forth. It should be understood that these examples are for illustrative purposes only and are not to be construed as limiting this invention in any manner.

EXAMPLE 1

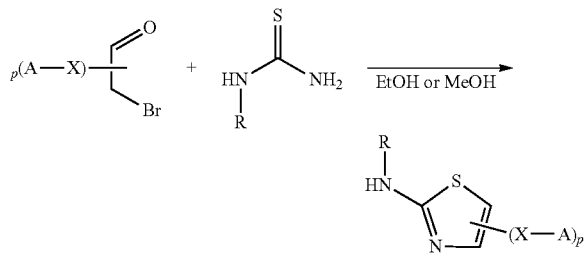

General Procedure: The appropriate bromoketone was dissolved in a minimum of ethanol or methanol with 1.1 equivalents of thiourea. The reaction mixture was stirred overnight at room temperature, evaporated to dryness, and then dissolved in either dichloromethane or ethyl acetate. The reaction mixture was then extracted with 1 M sodium hydroxide followed by a saturated aqueous solution of sodium chloride. The organic layer was then separated, dried over sodium sulfate, and evaporated to dryness to yield the desired 2-aminothiazole.

EXAMPLE 2

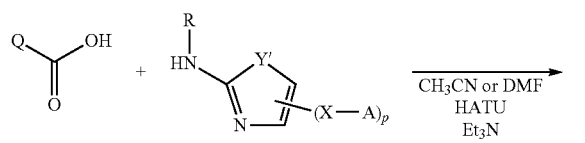

124

-continued

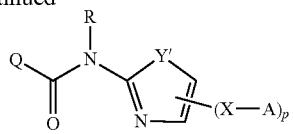

General Procedure: One equivalent of the appropriate carboxylic acid and one equivalent of the appropriate amine were dissolved in N,N-dimethylformamide (DMF) containing triethylamine (3 equivalents). O-(7-Azabenzotriazol-1-yl)-N,N,N',N'-tetramethyluronium hexafluorophosphate (HATU) was added and the solution was allowed to stir. The crude product was purified by reverse-phase preparative liquid chromatography to yield the pure product.

EXAMPLE 3

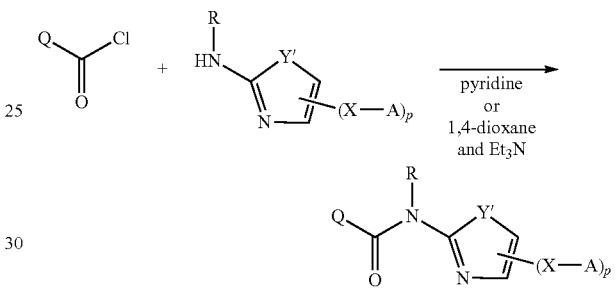

General Procedure: The appropriate acid chloride was added to one equivalent of the appropriate amine in minimum of pyridine. The reaction mixture was allowed to stir overnight at room temperature. The reaction mixture was then filtered and evaporated to dryness. The crude product was purified by reverse-phase preparative liquid chromatography. Alternatively, the acid chloride was added to one equivalent of the appropriate amine in minimum of 1,4-dioxane containing an excess of triethylamine. The reaction mixture was then either allowed to stir overnight at room temperature or subjected to microwave irradiation for 5 minutes at 200° C. The crude product was then filtered, evaporated to dryness, dissolved in a minimum of dimethylsulfoxide and then purified by reverse-phase preparative liquid chromatography.

EXAMPLE 4

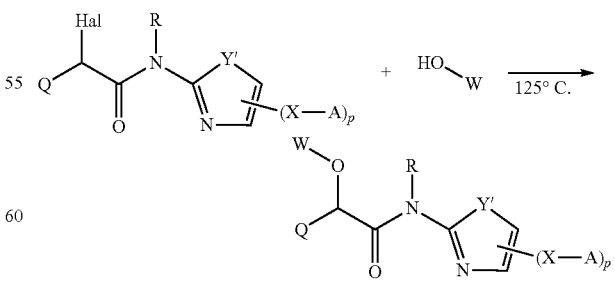

Hal = Cl, Br, I wherein W is a group as described in the compounds of the present invention.

General Procedure: One equivalent of the halide was dissolved in a minimum of the alcohol. The reaction vessel was sealed and then subjected to microwave irradiation for 15 minutes at 125° C. The crude mixture was evaporated to dryness, dissolved in 1 mL of dimethylsulfoxide and purified by reverse-phase preparative liquid chromatography.

EXAMPLE 5

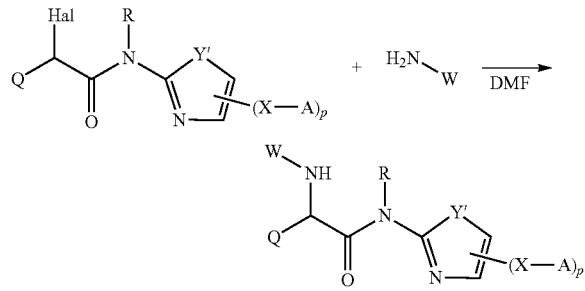

wherein W is a group as described in the compounds of the present invention.

General Procedure: One equivalent of the halide was dissolved in a minimum of N,N-dimethylformamide (DMF) containing 20 equivalents of amine. The reaction vessel was sealed and then subjected to microwave irradiation for 5 minutes at 80° C. The crude mixture was evaporated to dryness and purified by reverse-phase preparative liquid chromatography.

1)

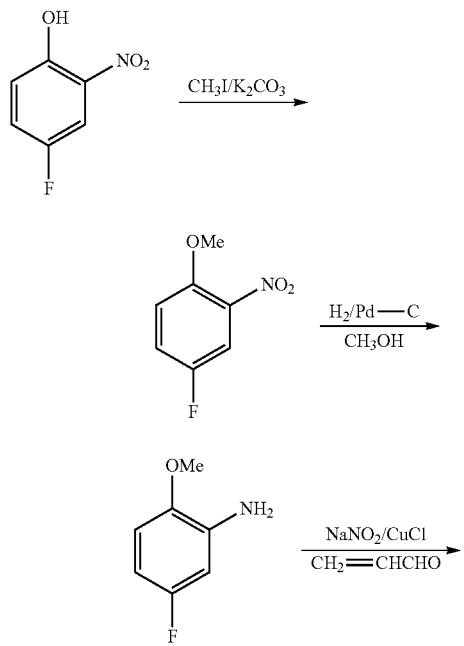

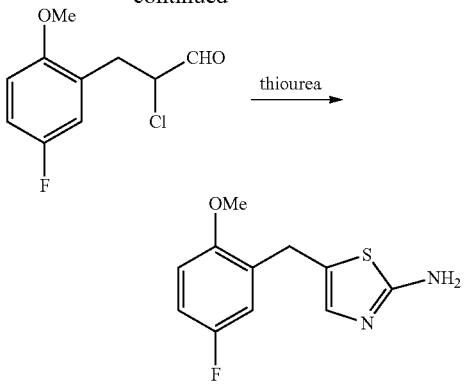

a) 4-Fluoro-1-methoxy-2-nitro-benzene A solution of methyl iodide (127.8 g, 0.9004 mol) in acetonitrile (100 mL) was slowly added to a solution of 5-fluoro-2-nitrophenol (94.2 g, 0.600 mol) and potassium carbonate (20g, 1.50 mol) in acetonitrile (450 mL). The mixture was heated to reflux for 15 hours. The mixture was allowed to cool, filtered, and washed twice with dichloromethane (100 mL). The combined filtrated was evaporated to dryness to give the desired product (96 g, 0.56 mol, 93%), which was used directly in the next step.

b) 5-Fluoro-2-methoxy-phenylamine A solution of 4-fluoro-1-methoxy-2-nitro-benzene (85 g, 0.50 mol) in methanol (300 mL) containing palladium on carbon (10%, 8 g) was stirred for 15 hours under an atmosphere of hydrogen. The catalyst was filtered and the filtrate was evaporated to dryness to give the crude product (61.5 g, 0.436 mol, 87%), which was used directly in the next step.

c) 2-Chloro-3-(5-fluoro-2-methoxy-phenyl)-propionaldehyde A solution of sodium nitrite (36 g, 0.51 mole) in water (50 mL) was slowly added to a solution of 5-fluoro-2-methoxy-phenylamine (61.5 g, 0.48 mol) in hydrochloric acid (20% aqueous solution, 115 mL) at 0° C. After stirring for 10 minutes, a cooled (0° C.) solution of acrolein (50 mL, 0.75 mol) in acetone (100 mL) containing calcium oxide (0.56 g, 0.010 mol) was added slowly to the reaction mixture. This was then followed by a solution of cuprous chloride (5 g, 0.05 mol) in acetone (100 mL) containing hydrochloric acid (20% aqueous solution, 10 mL). The mixture was stirred at 0 to 30° C. for 3 hours, and then extracted three times with dichloromethane (300 mL). The combined organic layers were washed with a saturated aqueous solution of sodium bicarbonate, a saturated, aqueous solution of sodium chloride, dried over sodium sulfate, filtered, and evaporated to dryness to give a black viscous oil. The crude product was passed through a short silica column to give the crude product, which was used directly in the next step.

d) 5-(5-Fluoro-2-methoxy-benzyl)-thiazol-2-ylamine A mixture of 2-chloro-3-(5-fluoro-2-methoxy-phenyl)-propionaldehyde (crude from above) and thiourea (29.2 g, 0.384 mol) in ethanol (400 mL) was heated to reflux for 15 hours. The solvent was removed and the residue was diluted with dichloromethane (300 mL), sodium hydroxide (10% aqueous solution, 150 mL) and water (200 mL). The aqueous phase was extracted twice with dichloromethane (150 mL). The combined organic layer was washed with water, a saturated aqueous solution of sodium chloride, dried over sodium sulfate, and evaporated to dryness. The crude product was recrystallized from a mixture of ethyl acetate and hexanes to give the pure product (6.5 g, 0.027 mol, 6.2% from 5-fluoro-2-methoxy-phenylamine). ESI-MS m/z calc. 238.1, found 239.2 (M+1)+ 1H NMR (CDCl3): δ 6.90-6.81 (m, 2 H), 6.79-6.76 (m, 2 H), 4.75 (br, 2 H), 3.91 (s, 2 H), 3.82 (s, 3 H).

2)

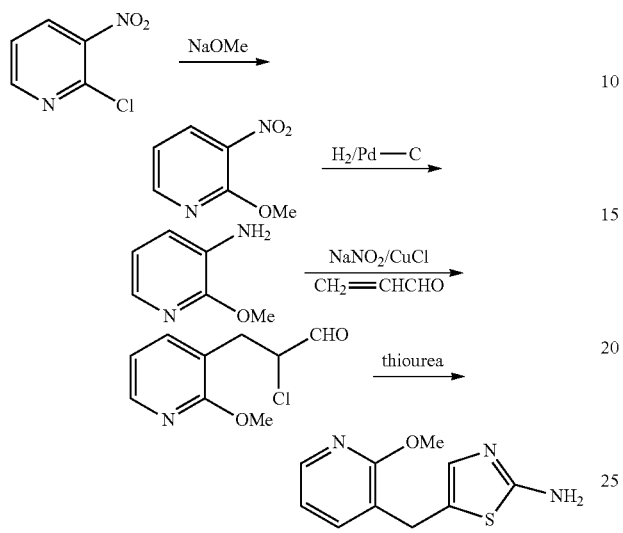

a) 2-Methoxy-3-nitro-pyridine A suspension of sodium methoxide (40.5 g, 0.750 mol) in 200 mL of methanol was slowly added to a solution of 2-chloro-3-nitro-pyridine (79.3 g, 0.500 mol) in 800 mL of methanol at 0° C. The reaction mixture was stirred for 4 hours and then poured into 1000 g of ice. The resulting-precipitate was filtered, washed with water, and dried to give 2-methoxy-3-nitro-pyridine (70. g, 0.45 mmol, 90%) as a white solid.

b) 2-Methoxy-pyridin-3-ylamine A solution of 2-methoxy-3-nitro-pyridine (70. g, 0.45 mol) in methanol (700 mL) containing palladium on carbon (7 g, 10%) was stirred under an atmosphere of hydrogen for 15 hours. The catalyst was filtered and washed with methanol. The filtrate was evaporated to dryness to give crude 2-methoxy-pyridin-3-ylamine (48 g, 0.39 mol, 87%), which was used directly in the next step.

c) 2-Chloro-3-pyridin-3-yl-propionaldehyde A solution of sodium nitrite (20. g, 0.28 mol) in water (100 mL) was slowly added to a solution of 2-methoxy-pyridin-3-ylamine (36 g, 0.25 mol) in hydrochloric acid (20% aqueous solution, 60 mL) at 0° C. After stirring for 10 minutes, a cooled (0° C.) solution of acrolein (25 mL, 0.37 mol) in acetone (25 mL) containing calcium oxide (5 g, 0.09 mol) was slowly added to the reaction mixture. This was then followed by a solution of cuprous chloride (2.5 g, 0.025 mol) in acetone (25 mL) containing hydrochloric acid (20% aqueous solution, 5 mL). The mixture was stirred at 0 to 30° C. for 3 hours, and then extracted three times with dichloromethane (150 mL). The combined organic layers were washed with a saturated aqueous solution of sodium bicarbonate, a saturated aqueous solution of sodium chloride, dried over sodium sulfate, filtered, and evaporated to dryness to give a black viscous oil. The crude product was passed through a short silica column to give a crude product, which was used directly in the next step.

d) 5-(2-Methoxy-pyridin-3-ylmethyl)-thiazol-2-ylamine A mixture of 2-chloro-3-pyridin-3-yl-propionaldehyde (crude from above) and thiourea (14.8 g, 0.194 mol) in ethanol (200 mL) was heated to reflux overnight. The solvent was removed and the residue was diluted with dichoromethane (1.2 L) and then washed with sodium hydroxide (10% aqueous solution, 400 mL) and water (200 mL). The organic layer was extracted three times with hydrochloric acid (5% aqueous solution, 400 mL) and the combined aqueous layer was brought to between pH 9 and 10 with sodium hydroxide (10% aqueous solution). The resulting precipitate was filtered to give the crude product, which was recrystallized, from ethyl acetate and hexanes to give the pure product (5.1 g, 0.023 mol, 5.6% from 2-methoxy-pyridin-3-ylamine). ESI-MS m/z calc. 221.1, found 222.2 (M+1)+.

3)

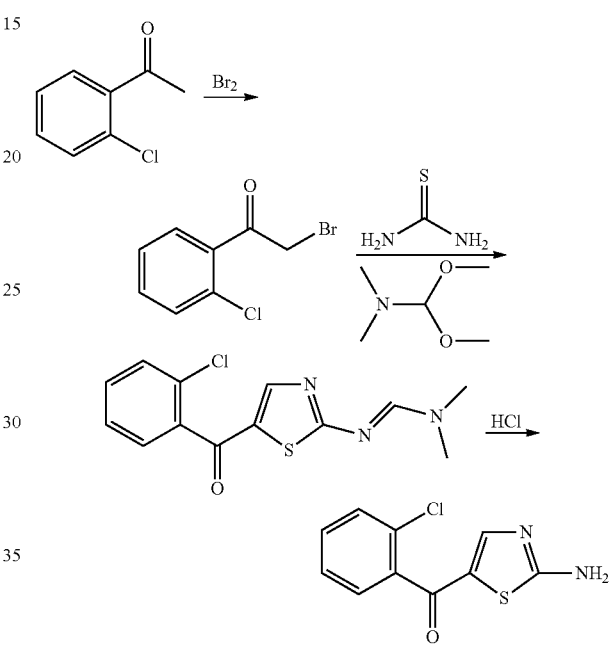

a) 2-Bromo-1-(chloro-phenyl)-ethanone Bromine (3.8 mL, 65 mmol) was added dropwise to a solution of 1-(2-chloro-phenyl)-ethanone (10. g, 65 mmol) in acetic acid (75 mL) at 0° C. The mixture was then warmed to room temperature and stirred overnight. The mixture was evaporated to dryness and used in the next step without further purification. N'-[5-(2-Chloro-benzoyl)-thiazol-2-yl]-N,N-dimethyl-formamidine. A mixture of thiourea (4.95 g, 65.0 mmol) and dimethoxymethyl-dimethyl-amine (23.2 g, 195 mmol) in methanol (80 mL) was heated under reflux for 30 minutes. After allowing the mixture to cool, triethylamine (19.8 g, 195 mmol) and a solution of 2-bromo-1-(chloro-phenyl)-ethanone (crude from last step) in methanol (50 mL) were added. The mixture was heated to reflux for 4 hours. The solvent was removed and the residue was used directly in the next procedure.

b) (2-Amino-thiazol-5-yl)-(2-chloro-phenyl)-methanone The crude N'-[5-(2-chloro-benzoyl)-thiazol-2-yl]-N,N-dimethyl-formamidine was dissolved in 10% aqueous hydrochloric acid (150 mL) and heated to 70° C. for 4 hours. The precipitate was filtered, washed with ether, and then suspended in a 10% aqueous sodium carbonate solution (250 mL). The suspension was stirred for 1 hour and the precipitate was filtered, washed with ether, and dried in air to give (2-amino-thiazol-5-yl)-(2-chloro-phenyl)-methanone as a brown solid (8.5 g, 36 mmol, 55% from 1-(2-chloro-phenyl)-ethanone). ESI-MS m/z calc. 238.0, found 239.3 (M+1)+ 1H NMR (DMSO): δ: 7.252 (s, 1 H), 7.420-7.553 (m, 4 H), 8.345 (s, 2 H).

4)

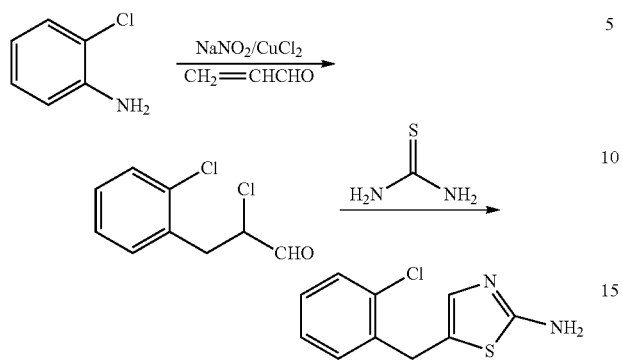

a) 2-Chloro-3-(2-chloro-phenyl)-propionaldehyde To a solution of 2-chloroaniline (12.7 g, 100 mmol) in hydrochloric acid (20% aqueous solution, 40 mL) was added dropwise a solution of sodium nitrite (7.5 g, 110 mmol) in water (20 mL) at 0 to 5° C. After stirring for 10 minutes, a cooled (0° C.) solution of acrolein (15 g, 270 mmol) in acetone (100 mL) containing calcium oxide (2.0 g, 36 mmol) was added gradually, and then followed by a solution of cuprous chloride (1 g, 10 mmol) in acetone (10 mL) containing hydrochloric acid (20% aqueous solution, 2 mL). The mixture was stirred at 0 to 30° C. for 3 hours and then extracted three times with dichloromethane (100 mL). The combined organic layers were washed with a saturated aqueous solution of sodium bicarbonate followed by a saturated aqueous solution of sodium chloride. The organic layer was separated, dried over sodium sulfate, and evaporated to dryness to give a black viscous oil. The crude product was passed through a short silica gel column to give 12 g of crude product, which was used directly in the next step.

b) 5-(2-Chloro-benzyl)-thiazol-2-ylamine A mixture of 2-chloro-3-(2-chloro-phenyl)-propionaldehyde (12 g, crude from above) and urea (6.0 g, 0.10 mol) in ethanol (120 mL) was heated to reflux overnight. The solvent was evaporated to dryness. The residue was diluted with dichloromethane (120 mL) and then washed with sodium hydroxide (10% aqueous solution, 50 mL) and water (30 mL). The organic layer was extracted three times with hydrochloric acid (5% aqueous solution, 120 mL). The combined aqueous layer was adjusted with a 10% aqueous solution of sodium hydroxide to between pH 9 and 10 and then extracted three times with dichloromethane (150 mL). The organic layers were combined, dried over sodium sulfate, evaporated to dryness, and purified by silica gel column chromatography to yield a yellow solid. (5.2 g, 0.023 mol, 23% from 2-chloroaniline). ESI-MS m/z calc. 224.0, found 225.2 (M+1)$^+$ $^1$H NMR (CDCl$_3$) δ 4.07 (s, 2H), 4.90 (bs, 2H), 6.80 (s, 1H), 7.37-7.15 (m, 4H).

6) 5-(2-methoxy-benzyl)-thiazol-2-ylamine

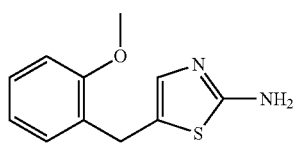

5-(2-methoxy-benzyl)-thiazol-2-ylamine was prepared in a manner analogous to that of 5-(2-chloro-benzyl)-thiazol-2-ylamine. ESI-MS m/z calc. 220.1, found 221.2 (M+1)$^+$ $^1$H NMR (CDCl$_3$) δ 7.26-7.19 (m, 1H), 7.15 (d, J=6.8 Hz, 1H), 6.90-6.85 (m, 2H), 6.79 (s, 1H), 4.77 (bs, 2H), 3.93 (s, 2H), 3.84 (s, 3H).

7) 5-(3-Chloro-benzyl)-thiazol-2ylamine

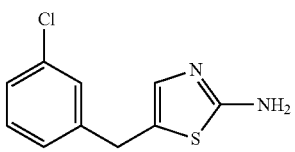 [SMILES: Nc1ncc(Cc2cccc(Cl)c2)s1]

5-(3-Chloro-benzyl)-thiazol-2-ylamine was prepared in a manner analogous to that of 5-(2-chloro-benzyl)-thiazol-2-ylamine. ESI -MS m/z calc. 224.0, found 225.2 (M+1)$^+$ $^1$H NMR (CDCl$_3$) δ 7.26-7.21 (m, 3H), 7.10 (d, J=6.8 Hz, 1H), 6.81 (s, 1H), 4.82 (bs, 2H), 3.93 (s, 2H).

8) 5-(4-Chloro-benzyl)-thiazol-2-ylamine

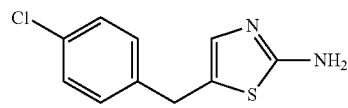 [SMILES: Nc1ncc(Cc2ccc(Cl)cc2)s1]

5-(4-Chloro-benzyl)-thiazol-2-ylamine was prepared in a manner analogous to that of 5-(2-chloro-benzyl)-thiazol-2-ylamine. ESI-MS m/z calc. 224.0, found 225.2 (M+1)$^+$ $^1$H NMR(CDCl$_3$) δ 7.26 (d, J=8.4 Hs, 2H), 7.14 (d, J=8.4 Hz, 2H), 6.79 (s, 1H), 4.85 (bs, 2H), 3.92 (s, 2H).

9) 5-(2-Cyano-benzyl)-thiazol-2-ylamine

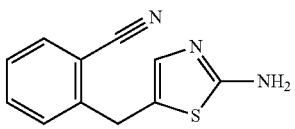 [SMILES: N#Cc1ccccc1Cc1cnc(N)s1]

5-(2-Cyano-benzyl)-thiazol-2-ylamine was prepared in a manner analogous to that of 5-(2-chloro-benzyl)-thiazol-2-ylamine (12 g, 56 mmol, 11% from 2-cyanoaniline). ESI-MS m/z calc. 215.05, found 216.16 (M+1)$^+$ $^1$H NMR(CDCl$_3$): δ 7.64 (d, 1H), 7.54 (t, 1H), 7.34 (m, 2H), 6.87 (s, 1H), 4.89 (br, 2H), 4.19 (s, 2H).

10)

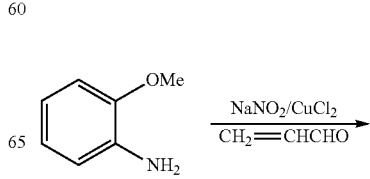

-continued

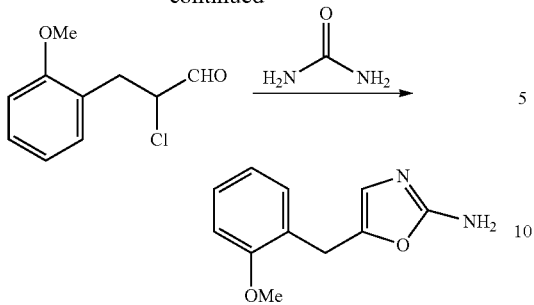

a) 2-Chloro-3-(2-methoxy-phenyl)-propionaldehyde. A solution of 2-methoxyaniline (24.6 g, 0.200 mol) in hydrochloric acid (20% aqueous solution, 80 mL) was slowly added to a solution of sodium nitrite (15 g, 0.22 mol) in water (40 mL) at 0 to 5° C. After stirring for 10 minutes, a cooled (0° C. solution of acrolein (30 g, 0.56 mol) in acetone (200 mL) containing calcium oxide (4.0 g, 72 mmol) was slowly added, followed by a solution of cuprous chloride (2.0 g, 20 mmol) in acetone (20 mL) containing hydrochloric acid (20% aqueous solution, 4 mL). The mixture was stirred at 0 to 30° C. for 3 hours, and then extracted with three 150 mL portions of dichloromethane. The combined organic layers were washed with a saturated aqueous solution of sodium bicarbonate, a saturated aqueous solution of sodium chloride, dried over sodium sulfate, filtered, and concentrated to give a black viscous oil. The crude product was passed through a short silica column to give 10 g of crude product, which was used directly in the next procedure.

b) 5-(2-methoxy-benzyl)-oxazol-2-ylamine. A mixture of 2-chloro-3-(2-methoxylphenyl)-propionaldehyde (10 g, crude from above) and urea (9.6 g, 0.16 mol) was dissolved in ethanol (250 mL) and then heated to reflux overnight. The solvent was evaporated to dryness. The residue was diluted with dichloromethane (250 mL) and then washed with sodium hydroxide (10% aqueous solution, 100 mL) and water (50 mL). The organic layer was extracted three times with hydrochloric acid (5% aqueous solution, 250 mL). The combined aqueous layers were adjusted to pH 9 to 10 with a 10% aqueous solution of sodium hydroxide and then extracted three times with dichloromethane (300 mL). The organic layer was separated, dried over sodium sulfate, and evaporated to dryness. The crude product was purified by silica gel column chromatography to yield the yellow-red solid product, (0.72 g, 0.35% from 2-methoxyaniline). ESI-MS m/z calc. 204.1, found 205.1 (M+1)+ 1H NMR(CDCl3) δ 7.26-7.20 (m, 1H), 7.14 (d, J=7.2 Hz, 1H), 6.91-6.86 (m, 2H), 6.35 (s, 1H), 4.49 (bs, 2H), 3.85 (s, 2H), 3.82 (s, 3H).

11)

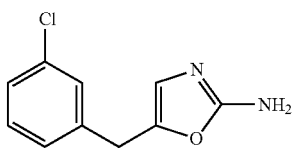 [SMILES: Nc1ncc(Cc2cccc(Cl)c2)o1]

5-(2-Chloro-benzyl)-oxazol-2-ylamine 5-(2-Chloro-benzyl)-oxazol-2-ylamine was prepared in a manner analogous to that of the preparation of 5-(2-methoxy-benzyl)-oxazol-2-ylamine to yield the product as a yellow solid. (3.5 g, 8.4% from 2-chloroaniline). ESI-MS m/z calc. 208.0, found 209.1 (M+1)+ 1H NMR (CDCl3) δ 7.37-7.18 (m, 4H), 6.40 (s, 1H), 4.66 (bs, 2H), 3.97 (s, 2H).

12)

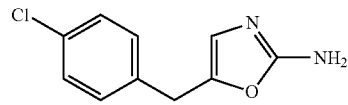 [SMILES: Nc1ncc(Cc2ccc(Cl)cc2)o1]

5-(3-Chloro-benzyl)-oxazol-2-ylamine 5-(3-Chloro-benzyl)-oxazol-2-ylamine was prepared in a manner analogous to that of the preparation of 5-(2-methoxy-benzyl)-oxazol-2-ylamine to yield the product as a yellow solid (1.2 g, 2.9% from 3-chloroaniline), ESI-MS m/z calc. 208.0, found 209.2 1H NMR(CDCl3) δ 7.26-7.22 (m, 3H), 7.10 (d, J=6.0 Hz, 1H, 6.44 (s, 1H), 4.73 (bs, 2H), 3.82 (s, 2H).

13)

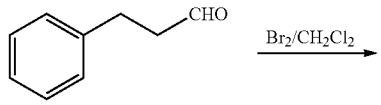

5-(4-Chloro-benzyl)-oxazol-2-ylamine 5-(4-Chloro-benzyl)-oxazol-2-ylamine was prepared in a manner analogous to that of the preparation of 5-(2-methoxy-benzyl)-oxazol-2-ylamine to yield the product as a yellow solid (1.6 g, yield 3.86% from 4-chloroaniline). ESI-MS m/z calc. 208.0, found 209.1 1H NMR (CDCl3) δ 7.27 (d, J=8.4 Hz, 2H), 7.17 (d, J=8.0 Hz, 2H), 6.38 (s, 1H), 4.66 (bs, 2H), 3.81 (s, 2H).

14)

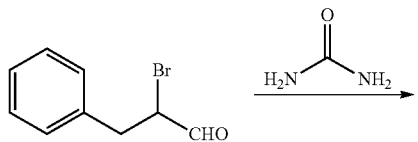

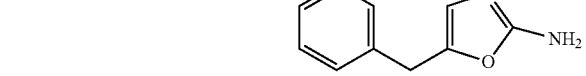

a) 2-Bromo-3-phenylpropionaldehyde A solution of bromine (15.2 g, 95.1 mmol) in 30 mL of dichloromethane was added to a solution of 3-phenyl-propionaldehyde (13.4 g, 100 mmol) in dichloromethane (150 mL) at 0° C. over 20 minutes. The reaction mixture was allowed to stir for 2 hours and then a saturated aqueous solution of sodium bicarbonate (100 mL) was added to the mixture. The organic layer was separated and the aqueous layer was washed with dichloromethane (50 mL). The combined organic layers were washed with water, a saturated aqueous solution of sodium chloride, and then evaporated to dryness to give an orange oil (14.2 g), which was used directly in the next step.

b) 5-Benzyl-oxazol-2-ylamine A mixture of 2-bromo-3-phenylpropionaldehyde (14.2 g, crude from above) and urea (7.2 g, 0.12 mol) were heated to reflux for 15 hours in 200 mL of ethanol. The solvent was evaporated to dryness and the residue was diluted with dichloromethane (250 mL) and then washed with sodium hydroxide (10% aqueous solution, 100 mL) and water (50 mL). The organic layer was extracted three times with hydrochloric acid (5% aqueous solution, 250 mL). The combined aqueous layers were adjusted to between pH 9 to 10 with a 10% aqueous solution of sodium hydroxide and then extracted three times with dichloromethane (300 mL). The organic layer was dried over sodium sulfate, evaporated to dryness, and purified by silica gel column chromatography to give a pale yellow solid. (1.6 g, 9.2 mmol, 9.2% from 3-phenyl-propionaldehyde). ESI-MS m/z calc. 174.1, found 175.1 $^1$H NMR (CDCl$_3$) δ 7.32-7.22 (m, 5H), 6.39 (s, 1H), 4.72 (bs, 2H), 3.84 (s, 2H).

15)

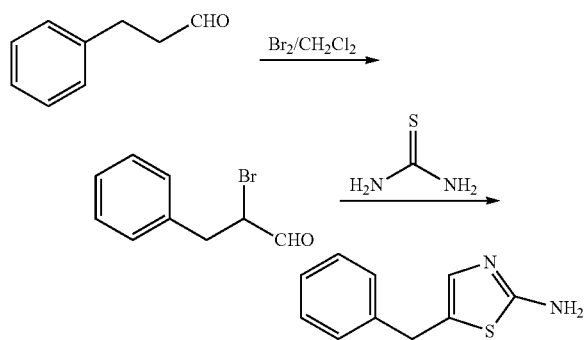

a) 2-Bromo-3-phenylpropionaldehyde A solution of bromine (15.2 g, 95.1 mmol) in 30 mL of dichloromethane was added to a solution of 3-phenyl-propionaldehyde (13.4 g, 100 mmol) in dichloromethane (150 mL) at 0° C. over 20 minutes. The reaction mixture was allowed to stir for 2 hours and then a saturated aqueous solution of sodium bicarbonate (100 mL) was added to the mixture. The organic layer was separated and the aqueous layer was washed with dichloromethane (50 mL). The combined organic layers were washed with water, a saturated aqueous solution of sodium chloride, and then evaporated to dryness to give an orange oil (14.2 g), which was used directly in the next step.

b) 5-benzyl-thiazol-2-ylamine A mixture of 2-bromo-3-phenylpropionaldehyde (14.2 g, crude from above) and urea (7.2 g, 0.12 mol) were heated to reflux for 15 hours in 200 mL of ethanol. The solvent was evaporated to dryness and the residue was diluted with dichloromethane (250 mL) and then washed with sodium hydroxide (10% aqueous solution, 100 mL) and water (50 mL). The organic layer was extracted three times with hydrochloric acid (5% aqueous solution, 250 mL). The combined aqueous layers were brought to pH 9 to 10 with a 10% aqueous solution of sodium hydroxide and then extracted three times with dichloromethane (300 mL). The organic layer was dried over sodium sulfate, evaporated to dryness, and purified by silica gel column chromatography to give a pale yellow solid. (5.2 g, 27 mmol, 27% from 3-phenyl-propionaldehyde). ESI-MS m/z calc. 190.1, found 191.2 $^1$H NMR (CDCl$_3$) δ 7.32-7.21 (m, 5H), 6.79 (s, 1H), 4.91 (bs, 2H), 3.95 (s, 2H).

16)

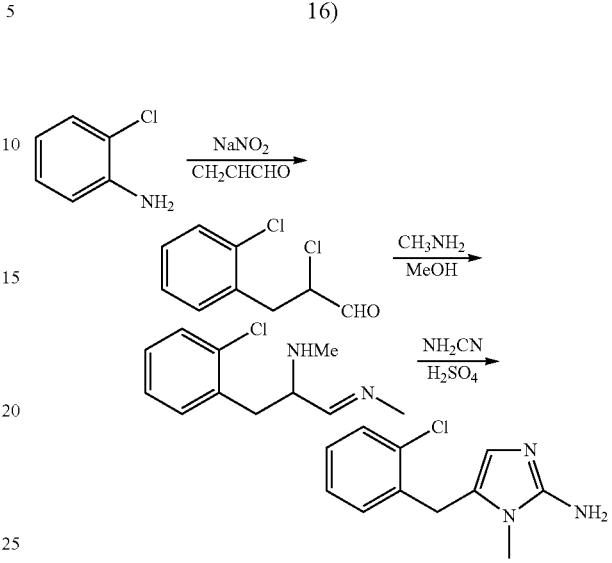

a) 2-Chloro-3-(2-chloro-phenyl)-propionaldehyde. A solution of sodium nitrite (15 g, 0.22 mol) in water (40 mL) was slowly added to a solution of 2-chloroaniline (25.5 g, 0.200 mol) in hydrochloric acid (20% aqueous solution, 100 mL) at 0 to 5° C. The mixture was stirred for ten minutes and then poured into a cooled (0° C.) solution of acrolein (30. g, 0.56 mol) in acetone (200 mL) containing calcium oxide (4.0 g, 72 mmol), followed by a solution of cuprous chloride (2.0 g, 20 mmol) in acetone (20 mL) containing hydrochloric acid (20% aqueous solution, 4 mL). The mixture was stirred for 3 hours at room temperature, and then extracted three times with dichloromethane (150 mL). The combined organic layers were washed with a solution of saturated aqueous sodium chloride, dried over sodium sulfate, filtered, and evaporated to dryness to give a black viscous oil that was used directly in the next procedure.

b) [2-(2-Chloro-phenyl)-1-methyliminomethyl-ethyl]-methyl-amine. A solution of methylamine in methanol (27%, 69 g) was slowly added to a solution of 2-chloro-3-(2-chloro-phenyl)-propionaldehyde in dichloromethane (20 mL). The reaction mixture was allowed to stir for 12 hours and then used immediately in the next procedure.

c) 5-(2-Chloro-benzyl)-1-methyl-1H-imidazol-2-ylamine. A solution of cyanamide in water (50%, 150 mL) was added to a boiling solution of [2-(2-chloro-phenyl)-1-methylimi-nomethyl-ethyl]-methyl-amine in methanol and dichloromethane. The pH was brought to 4.5 by the continual addition of an aqueous solution of sulfuric acid (9 M). The mixture was refluxed for 2 hours, allowed to cool to room temperature, and adjusted to pH 9 through the addition of powdered sodium bicarbonate. The mixture was extracted three times with dichloromethane (200 mL) and the combined organic layers were extracted three times with hydrochloric acid (20% aqueous solution, 150 mL). The aqueous solution was adjusted to pH 10 with sodium hydroxide (10% aqueous solution) and extracted three times with dichloromethane (150 mL). The combined organic layers were washed with a saturated aqueous solution of sodium chloride, dried over sodium sulfate, filtered, and evaporated to dryness to give a black solid which was purified by column chromatography to yield the product (5.0 g, 0.23 mmol, 11% from 2-chloroaniline) as a brown solid. ESI-MS m/z calc. 221.1, found 222.3 (M+1)+ 1H NMR (CDCl3): δ 7.30-7.37 (m, 1 H), 7.15-7.18 (m, 2 H), 7.03-7.06 (m, 1 H), 6.43 (s, 1 H), 3.94 (s, 2H), 3.80 (br, 2H), 3.15 (s, 3 H).

17)

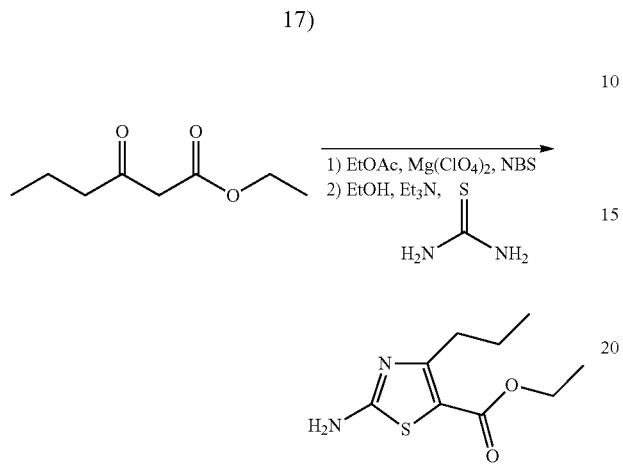

a) 2-Bromo-3-oxo-hexanoic acid ethyl ester 3-Oxo-hexanoic acid ethyl ester (4.0 mL, 25 mmol) and magnesium perchlorate (1.7 g, 7.6 mmol) were placed in 500 mL of ethyl acetate and allowed to stir for 5 minutes. N-Bromosuccinimide (4.7 g, 26 mmol) was added and the reaction mixture was allowed to stir for 15 minutes, at which time thin-layer chromatography (10% ethyl acetate in hexanes, silica gel, 254 nm irradiation) indicated the reaction was complete. The reaction mixture was diluted with 500 mL of ethyl ether and washed three times with an equal volume of saturated aqueous sodium chloride. The organic layer was then dried over sodium sulfate and evaporated to dryness. This material was used in the next step without further purification.

b) Amino-4-propyl-thiazole-5-carboxylic acid ethyl ester 2-Bromo-3-oxo-hexanoic acid ethyl ester (5.9 g, 25 mmol), was dissolved in 60 mL of ethanol containing triethylamine (4.2 mL, 30 mmol) and thiourea (1.9 g, 25 mmol). The colorless solution was protected from light and allowed to stir for 16 hours. The resulting red suspension was evaporated to dryness and dissolved in a minimum of dichloromethane. This solution was washed three times with an equal volume of a saturated aqueous solution of sodium bicarbonate, followed by a saturated aqueous solution of sodium chloride. The organic layer was separated and filtered to remove a fine red precipitate which remained suspended in the organic phase. The solvent was removed and then the solid was dissolved in a minimum of 50/50 (v/v) ethyl acetate and 1 N aqueous solution of hydrochloric acid. The layers were separated and the aqueous layer was washed with an equal volume of ethyl acetate. After discarding the organic layers, the aqueous layer was then placed in an ice bath with an equal volume of ethyl acetate. Sodium hydroxide (1N) was then slowly added with vigorous swirling until the aqueous phase was basic. The layers were separated and the aqueous layer was washed two additional times with ethyl acetate. The combined organic layers were washed three times with an equal volume of a solution of saturated aqueous sodium bicarbonate followed by a solution of saturated aqueous sodium chloride. The organic layer was then dried over sodium sulfate and evaporated to dryness to yield a pale yellow solid (1.8 g, 8.4 mmol, 34%) ESI-MS m/z calc. 214.1, found 215.3 (M+1)+ Retention time 1.90 minutes.

18) 4-(2-Methoxy-phenyl)-thiazol-2-ylamine.

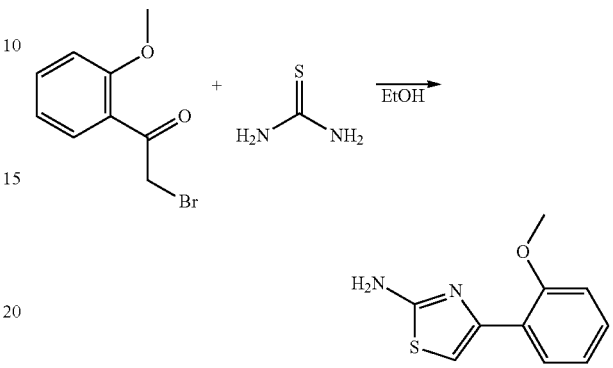

2Bromo-1-(2-methoxy-phenyl)-ethanone (0.6388 g, 2.789 mmol) and thiourea (0.2289 g, 3.007 mmol) were dissolved in a 20 mL of ethanol. The reaction mixture was allowed to stir overnight at room temperature. The ethanol was evaporated to dryness and the crude product was dissolved in a minimum of dichloromethane. The crude product was then extracted twice with 1M sodium hydroxide and once with a saturated aqueous solution of sodium chloride. The organic layer was then dried over sodium sulfate, filtered, and evaporated to dryness to yield the pure product (0.529 g, 2.56 mmol, 92.0%). ESI-MS m/z calc. 206.3, found 207.1 (M+1)+ Retention time 1.86 minutes. 1H NMR (400 MHz, CD3CN) δ 3.91 (s, 3H), 5.54 (s, 2H), 6.97-7.02 (m, 1H), 7.03-7.06 (m, 1H), 7.23 (s, 1H), 7.24-7.29 (m, 1H), 8.06 (dd, J=7.8, 1.8 Hz, 1H).

19) 4-(3-Methoxy-phenyl)-thiazol-2-ylamine.

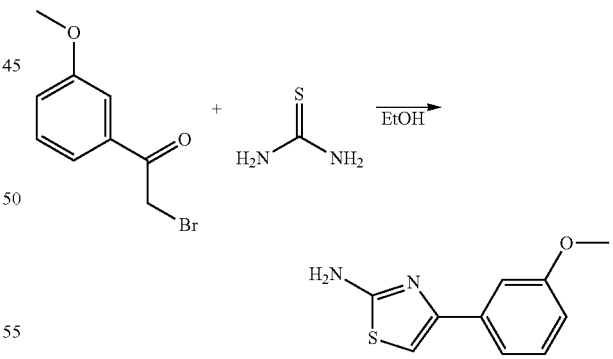

2-Bromo-1-(3-methoxy-phenyl)-ethanone (0.7291 g, 3.183 mmol) and thiourea (0.2665 g, 3.501 mmol) were dissolved in a 20 mL of ethanol. The reaction mixture was allowed to stir overnight at room temperature. The ethanol was evaporated to dryness and the crude product was dissolved in a minimum of dichloromethane. The crude product was then extracted twice with 1M sodium hydroxide and once with a saturated aqueous solution of sodium chloride. The organic layer was then dried over sodium sulfate, filtered, and evaporated to dryness to yield the product (0.619 g, 3.00 mmol, 94.3%). ESI-MS m/s calc. 206.3, found 207.0 (M+1)+ Retention time 1.86 minutes. ¹H NMR (400 MHz, CD₃CN) δ 3.84 (s, 3H), 5.67 (s, 2H), 6.85-6.91 (m, 2H), 7.31 (t, J=7.9 Hz, 1H), 7.36-7.43 (m, 2H).

20) 4-Phenyl-thiazol-2-ylamine

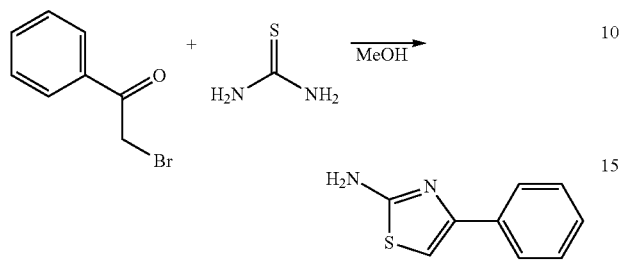

2-Bromo-1-phenyl-ethanone (19.9 g, 0.100 mol) and thiourea (7.9 g, 0.10 mol) were mixed in a 150 mL of methanol. The reaction mixture was warmed to dissolves the reagents and then allowed to stir overnight at room temperature. The methanol was evaporated to dryness and the crude product was dissolved in a minimum of ethyl acetate. The crude product was then extracted twice with 1M sodium hydroxide and once with a saturated aqueous solution of sodium chloride. The organic layer was then dried over sodium sulfate, filtered, and evaporated to dryness to yield the pure product (16.8 g, 0.0953 mol, 95.3%) of product. ESI-MS m/z calc. 176.0, found 177.2 (M+1)+ Retention time 1.41 minutes. ¹H NMR (400 MHz, CD₃CN) δ 5.73 (s, 2H), 6.87 (s, 1H), 7.28-7.34 (m, 1H), 7.36-7.43 (m, 2H), 7.79-7.85 (m, 2H).

21)

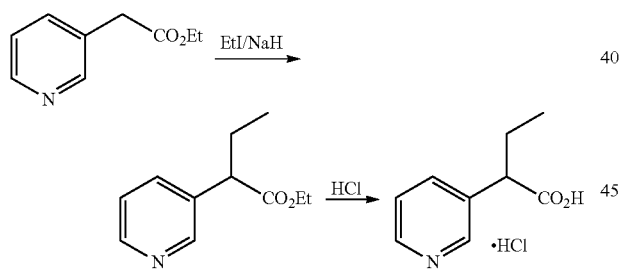

a) 2-Pyridin-3-yl-butyric acid ethyl ester Pyridin-3-yl-acetic acid ethyl ester (22.5 g, 0.136 mol) in tetrahydrofuran (50 mL) was slowly added to a suspension of sodium hydride (60% in mineral oil, 6 g, 0.4 mol) in tetrahydrofuran (50 mL) at 0° C. A solution of ethyl iodide (23.4 g, 0.150 mol) in tetrahydrofuran (50 mL) was added to and the reaction mixture was allowed to stir overnight at room temperature. The mixture was poured into ice and the aqueous layer was extracted three times with ethyl acetate. The organic layer washed with a saturated aqueous solution of sodium chloride, dried over sodium sulfate, and evaporated to dryness. The crude residue was purified by preparative reverse phase liquid chromatography (13.5g, 0.0699 mol, 51.3%). ESI-MS m/z calc. 193.1, found 194.2 (M+1)+ ¹H NMR (CDCl₃) δ: 9.42-9.39 (m, 2 H), 8.58-8.55 (m, 1 H), 8.17-8.13 (m, 1 H), 5.09-4.97 (m, 2 H), 4.35 (t, 1 H, J=7.6 Hz), 3.04-2.95 (m, 1 H), 2.74-2.65 (m, 1 H), 2.10 (t, 3 H, J=7.2 Hz), 1.79 (t, 3 H, J=7.6 Hz).

b) 2-Pyridin-3-yl-butyric acid A mixture of 2-Pyridin-3-yl-butyric acid ethyl ester (8 g, 0.04 mol) and a 20% aqueous solution of hydrochloric acid (50 mL) was heated to reflux for 3 hours. The solvent evaporated to dryness to yield the desired product (5 g, 0.02 mol, 50%), ESI-MS m/z calc. 165.1, found 166.5 (M+1)+ ¹H NMR (DMSO-d₆): δ 8.86 (s, 1 H), 8.80 (d, 1 H, J=5.6 Hz), 8.47 (d, 1 H, J=8.0 Hz), 7.97 (dd, 1 H, J=5.6, 8.0 Hz), 3.83 (t, 1 H, J=8.0 Hz), 2.07-2.04 (m, 1 H), 1.82-1.80 (m, 1 H), 0.80 (t, 3 H, J=7.6 Hz).

22) N-{5-[(2-Chloro-phenyl)-hydroxy-methyl]-thiazol-2-yl}-2-phenyl-butyramide

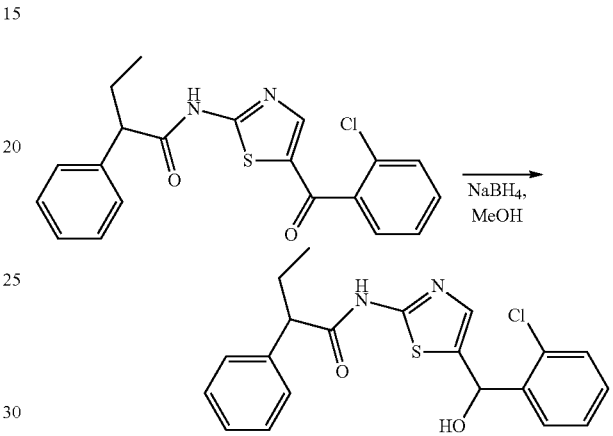

N-[5-(2-Chloro-benzoyl)-thiazol-2-yl]-2-phenyl-butyramide (102 mg, 0.265 mmol) was suspended in 1 mL of anhydrous methanol. Sodium borohydride (30.3 mg, 0.801 mmol) was slowly added and the resulting pale yellow solution was allowed to stir for 1 hour at room temperature. After stirring for one hour a second aliquot of sodium borohydride (30.3 mg, 0.801 mmol) was added. The reaction mixture was allowed to stir for an additional hour and then the crude product was evaporated to dryness and then dissolved in a minimum of ethyl acetate. The organic layer was washed three times with an equal volume of 1N hydrochloric acid, saturated aqueous sodium bicarbonate, and saturated aqueous sodium chloride. The organic layer was then dried over sodium sulfate, filtered, and evaporated to dryness. The crude product was further purified by reverse-phase preparative liquid chromatography to yield the pure product (46 mg, 0.12 mmol, 45%) ESI-MS m/z calc. 386.1, found 387.3 (M+1)+ Retention time 3.83 minutes.

23) N-[5-(2-Chloro-benzyl)-thiazol-2-yl]-2,2-diphenyl-acetamide

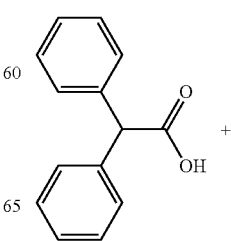

-continued

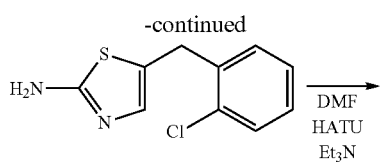

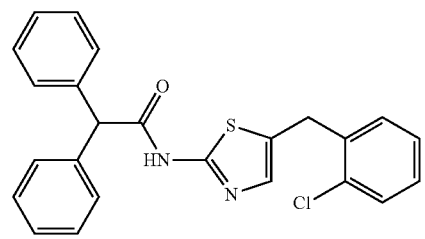

5-(2-Chloro-benzyl)-thiazol-2-ylamine (45 mg, 0.20 mmol) and diphenyl-acetic acid (42 mg, 0.20 mmol) were dissolved in N,N-dimethylformamide (1 mL) containing triethylamine (84.1 μL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (10.3 mg, 0.0246 mmol, 12%), ESI-MS m/z calc. 418.1, found 419.2 (M+1)$^+$ Retention time 3.85 minutes. $^1$H NMR (400 MHz, DMSO-d$_6$) δ 4.19 (s, 2H), 5.30 (s, 1H), 7.23-7.47 (m, 15H).

24) N-(7-Oxo-4,5,6,7-tetrahydro-benzothiazol-2-yl)-2-phenyl-butyramide

2-Amino-5,6-dihydro-4H-benzothiazol-7-one (34 mg, 0.20 mmol) and 2-phenyl-butyric acid (33 mg, 0.20 mmol) were dissolved in N,N-dimethylformamide (1 mL) containing triethylamine (84.1 μL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (31 mg, 0.099 mmol, 49%). ESI-MS m/z calc. 314.1, found 315.3 (M+1)$^+$ Retention time 2.90 minutes.

25) (2-Diphenylacetylamino-thiazol-4-yl)-acetic acid methyl ester

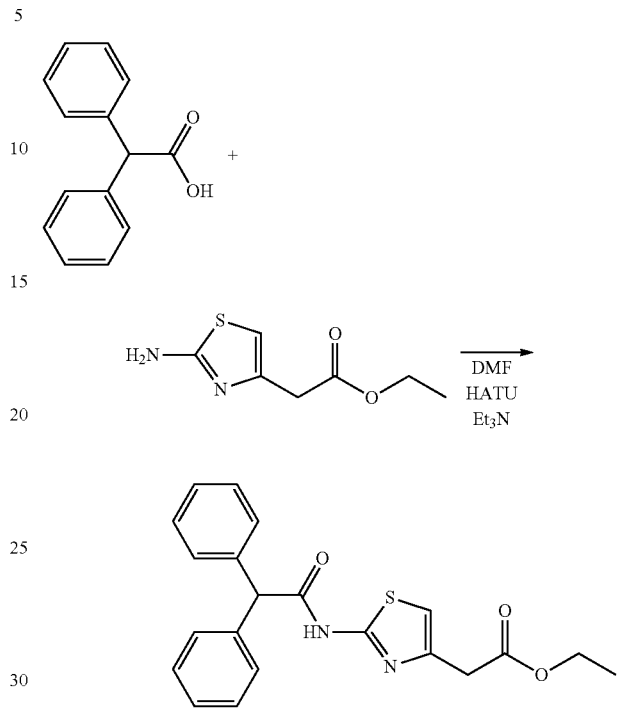

(2-Amino-thiazol-4-yl)-acetic acid methyl ester (45 mg, 0.20 mmol) and diphenyl-acetic acid (37 mg, 0.20 mmol) were dissolved in N,N-dimethylformamide (2 mL) containing triethylamine (84.1 μL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (29.4 mg, 0.0802 mmol, 40%). ESI-MS m/z calc. 380.1, found 381.3 (M+1)$^+$ Retention time 3.28 minutes.

26) 2-Diphenylacetylamino-thiazole-4-carboxylic acid ethyl ester

-continued

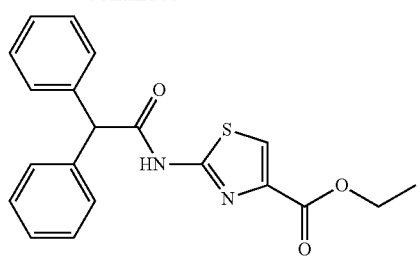

2-Amino-thiazole-4-carboxylic acid methyl ester (32 mg, 0.20 mmol) and diphenyl-acetic acid (42 mg, 0.20 mmol) were dissolved in N,N-dimethylformamide (1 mL) containing triethylamine (84.1 µL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (19 mg, 0.052 mmol, 26%). ESI-MS m/z calc. 366.1, found 367.1 (M+1)$^+$ Retention time 3.34 minutes.

27) N-[5-(2-Methoxy-pyridin-3-ylmethyl)-thiazol-2-yl]-2-phenyl-butyramide

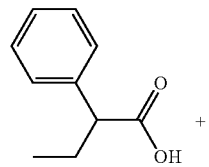

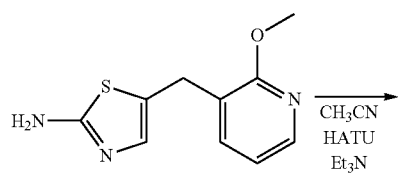

5-(2-Methoxy-pyridin-3-ylmethyl)-thiazol-2-ylamine (44 mg, 0.20 mmol) and 2-phenyl-butyric acid (33 mg, 0.20 mmol) were dissolved in acetonitrile (1 mL) containing triethylamine (84.1 µL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (15 mg, 0.041 mmol, 21%). ESI-MS m/z calc. 367.1, found 368.1 (M+1)$^+$ Retention time 3.24 minutes.

28) 2-Bromo-N-[5-(2-chloro-benzyl)-thiazol-2-yl]-2-phenyl-acetamide

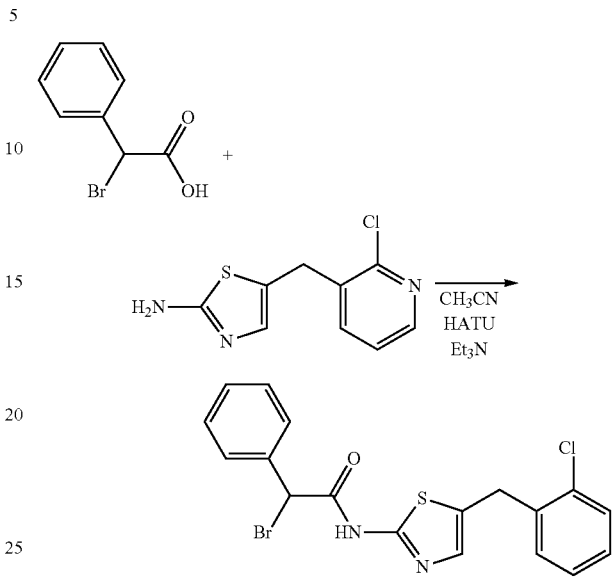

5-(2-Chloro-benzyl)-thiazol-2-ylamine (450 mg, 2.0 mmol) and bromo-phenyl-acetic acid (430 mg, 2.0 mmol) were dissolved in acetonitrile (20 mL) containing triethylamine (280 µL, 2.0 mmol). O-(7-Azabenzotriazol-1-yl)-N,N,N',N'-tetramethyluronium hexafluorophosphate (836 mg, 2.2 mmol) was added and the solution was allowed to stir for 16 hours. The crude product was purified by silica gel chromatography using a gradient of 10-30% ethyl acetate in hexanes to yield a pale yellow solid (633 mg, 1.50 mmol, 75.0%). ESI-MS m/z calc. 420.0, found 421.2 (M+1)$^+$ Retention time 3.63 minutes.

29) 2-Bromo-N-[5-(2-chloro-benzyl)-triazol-2-yl]-2-phenyl-acetamide

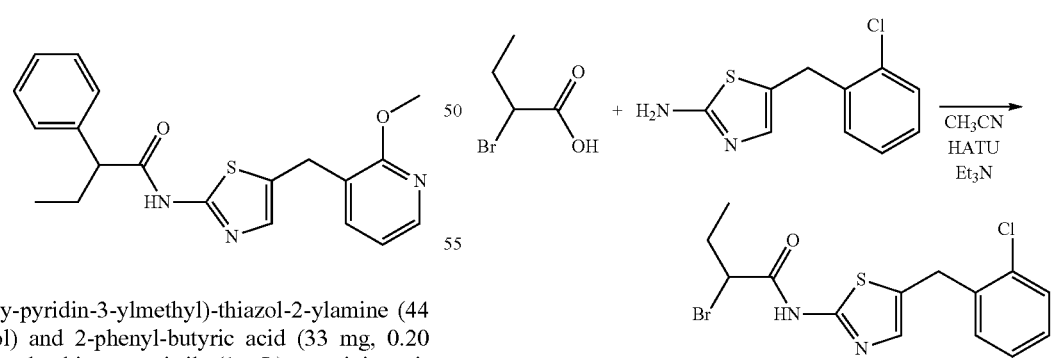

5-(2-Chloro-benzyl)-thiazol-2-ylamine (0.484 g, 2.16 mmol) and 2-bromo-butyric acid (0.360 g, 2.16 mmol) were dissolved in acetonitrile (20 mL) containing triethylamine (302 µL, 2.16 mmol). O-(7-Azabenzotriazol-1-yl)-N,N,N'N'-tetramethyluronium hexafluorophosphate (1.15 g, 3.02 mmol) was added and the solution was allowed to stir for 16

30) N-[5-(4-Chloro-benzyl)-oxazol-2yl]-2-cyclopentyl-2-phenyl-acetamide

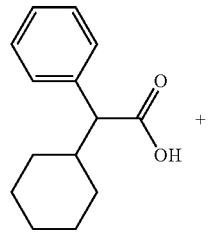

+

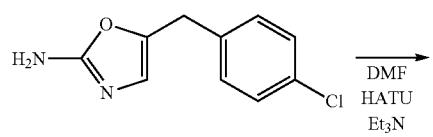

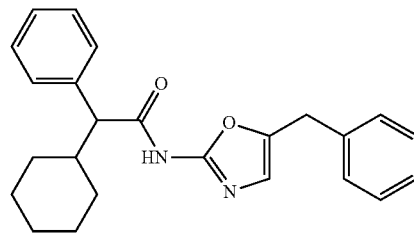

5-(4-Chloro-benzyl)-oxazol-2-ylamine (42 mg, 0.20 mmol) and cyclohexyl-phenyl-acetic acid (44 mg, 0.20 mmol) were dissolved in N,N-dimethylformamide (1 mL) containing triethylamine (84.1 μL, 0.600 mmol). O-(7-Azabenzotriazol-1-yl)-N,N,N',N'-tetramethyluronium hexafluorophosphate (84 mg, 0.22 mmol) was added, and the solution was allowed to stir for 16 hours. The crude product was purified by reverse-phase preparative liquid chromatography (9.6 mg, 0.023 mmol, 12%). ESI-MS m/z calc. 408.9, found 409.4 (M+1)⁺ Retention time 3.76 minutes.

31) N-[5-(2-Chloro-benzyl)-1-methyl-1H-imidazol-2-yl]-2-phenyl-butyramide

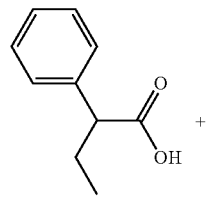

+

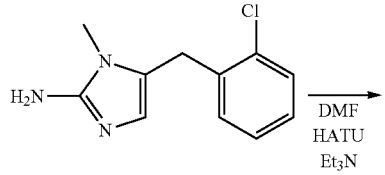

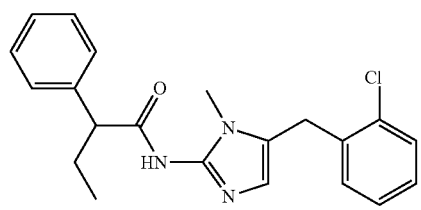

5-(2-Chloro-benzyl)-1-methyl-1H-imidazol-2-ylamine (44 mg, 0.20 mmol) and 2-phenyl-butyric acid (33 mg, 0.20 mmol) were dissolved in N,N-dimethylformamide (1 mL) containing triethylamine (84.1 μL, 0.600 mmol). O-(7-Azabenzotriazol-1-yl)-N,N,N',N'-tetramethyluronium hexafluorophosphate (84 mg, 0.22 mmol) was added and the solution was allowed to stir for 16 hours. The crude product was purified by reverse-phase preparative liquid chromatography (13 mg, 0.035 mmol, 18%), ES(-MS m/z calc. 367.2, found 368.1 (M+1)⁺ Retention time 2.42 minutes.

32)
N-(6-Ethoxy-benzothiazol-2yl)-2-phenyl-butyramide

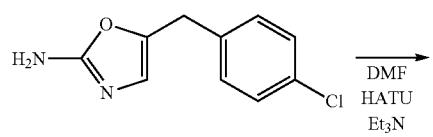

+

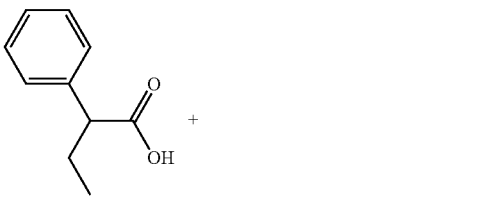

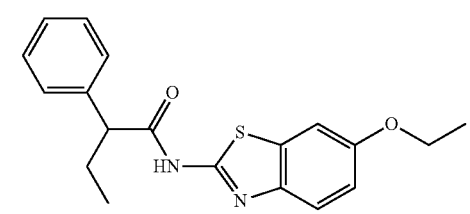

6-Ethoxy-benzothiazol-2-ylamine (39 mg, 0.20 mmol) and 2-phenyl-butyric acid (33 mg, 0.20 mmol) were dissolved in N,N-dimethylformamide (1 mL) containing triethylamine (84.1 μL, 0.600 mmol). O-(7-Azabenzotriazol-1-yl)-N,N,N', N'-tetramethyluronium hexafluorophosphate (84 mg, 0.22 mmol) was added and the solution was allowed to stir for 16 hours. The crude product was purified by reverse-phase preparative liquid chromatography (17 mg, 0.050 mmol, 25%), ESI-MS m/z calc. 340.1, found 340.9 (M+1)+ Retention time 3.55 minutes.

33) 4-Methyl-N-(4-phenyl-thiazol-2yl)-benzamide

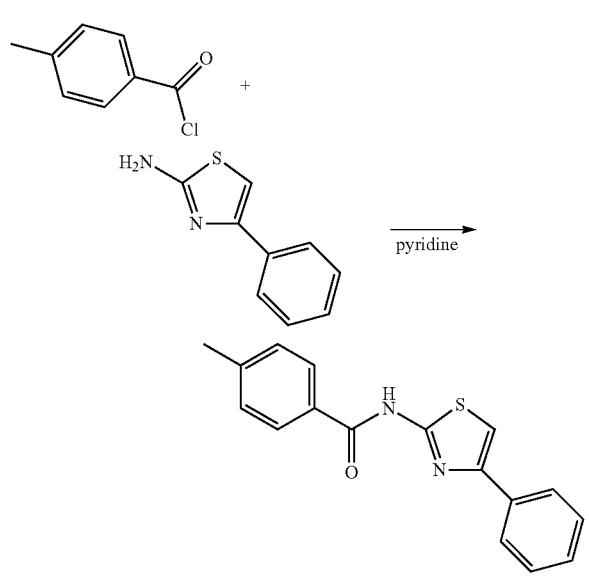

4-Phenyl-thiazol-2-ylamine (35.2 mg, 0.200 mmol) and 4-methyl-benzoyl chloride (30.9 mg, 0.200 mmol) were dissolved in 1 mL of pyridine. The reaction mixture was stirred at room temperature overnight and then purified by reverse-phase preparative liquid chromatography (20.6 mg, 0.0635 mmol, 31.8%). ESI-MS m/z calc. 294.1, found 295.2 (M+1)+ Retention time 3.55 minutes.

34) 4-Methyl-N-(4-phenyl-thiazol-2-yl)-benza

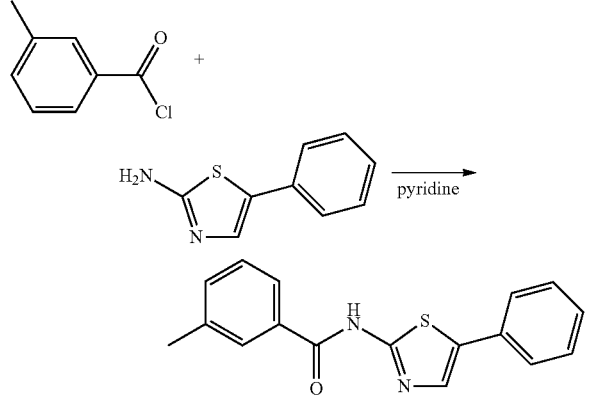

mide 5-Phenyl-thiazol-2-ylamine (35.2 mg, 0.200 mmol) and 4-methyl-benzoyl chloride (30.9 mg, 0.200 mmol) were dissolved in 1 mL of pyridine. The reaction mixture was stirred at room temperature overnight and then purified by reverse-phase preparative liquid chromatography (10.4 mg, 0.0353 mmol, 17.7%). ESI-MS m/z calc. 294.1, found 295.4 (M+1)+ Retention time 3.40 minutes.

35) N-[4-(2-Methoxy-phenyl)-thiazol-2-yl]-4-methyl-benzamide

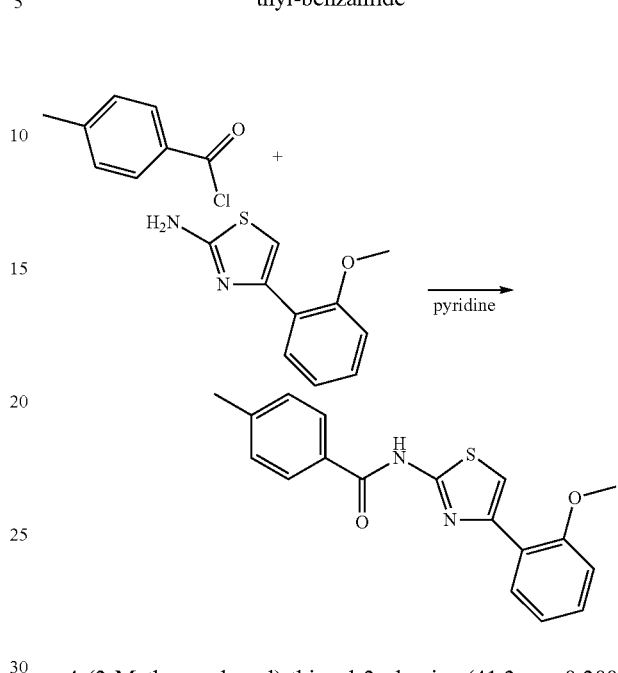

4-(2-Methoxy-phenyl)-thiazol-2-ylamine (41.3 mg, 0.200 mmol) and 4-methyl-benzoyl chloride (30.9 mg, 0.200 mmol) were dissolved in 1 mL of pyridine. The reaction mixture was stirred at room temperature overnight and then purified by reverse-phase preparative liquid chromatography (7.32 mg, 0.0226 mmol, 11.3%). ESI-MS m/z calc. 324.1, found 325.2 (M+1)+ Retention time 3.75 minutes.

36) N-[4-(2-Methoxy-phenyl)-thiazol-2yl]-benzamide

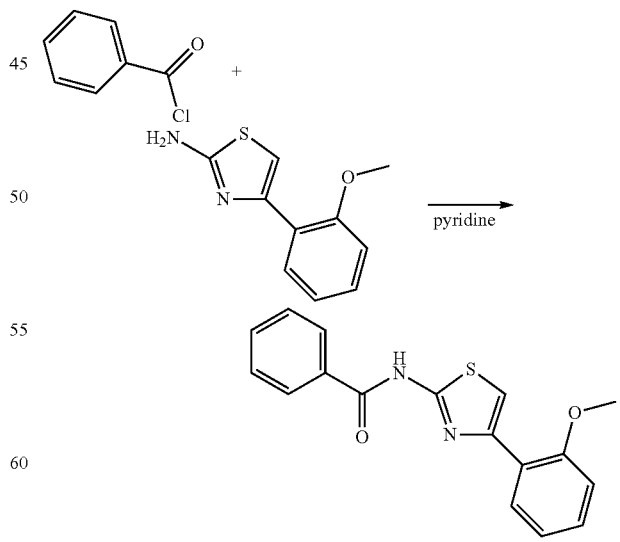

4-(2-Methoxy-phenyl)-thiazol-2-ylamine (41.3 mg, 0.200 mmol) and benzoyl chloride (28.1 mg, 0.200 mmol) were dissolved in 1 mL of pyridine. The reaction mixture was stirred at room temperature overnight and then purified by reverse-phase preparative liquid chromatography (11.4 mg, 0.0367 mmol, 18.4%) ESI-MS m/z calc. 310.1, found 311.2 (M+1)+ Retention time 3.55 minutes.

37) N-(4,5-Diphenyl-thiazol-2-yl)-benzamide

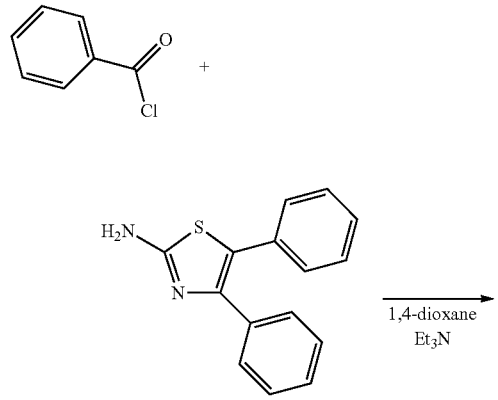

4,5-Diphenyl-thiazol-2-ylamine (50.5 mg, 0.200 mmol) and benzoyl chloride (28.1 mg, 0.200 mmol) were dissolved in 1,4-dioxane (2 mL) containing triethylamine (84.1 µL, 0.600 mmol). The reaction mixture was subjected to microwave irradiation for 5 minutes at 200° C. The crude product was filtered, evaporated to dryness, dissolved in 1 mL of dimethylsulfoxide and purified by reverse-phase preparative liquid chromatography (7.21 mg, 0.0202 mmol, 10.1%). ESI-MS m/z calc. 356.1, found 357.2 (M+1)+ Retention time 3.95 minutes.

38) N-(4,5-Diphenyl-thiazol-2-yl)-4-methyl-benzamide

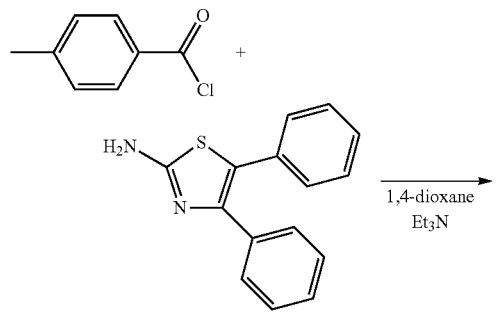

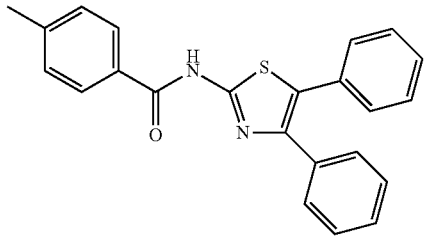

4,5-Diphenyl-thiazol-2-ylamine (50.5 mg, 0.200 mmol) and 4-methyl-benzoyl chloride (30.9 mg, 0.200 mmol) were dissolved in 1,4-dioxane (2 mL) containing triethylamine (84.1 µL, 0.600 mmol). The reaction mixture was subjected to microwave irradiation for 5 minutes at 200° C. The crude product was filtered, evaporated to dryness, dissolved in 1 mL of dimethylsulfoxide and purified by reverse-phase preparative liquid chromatography (18.6 mg, 0.0502 mmol, 25.1%). ESI-MS m/z calc. 370.1, found 371.2 (M+1)+ Retention time 4.13 minutes.

39) N-(4,5-Diphenyl-thiazol-2-yl)-4-methoxy-benzamide

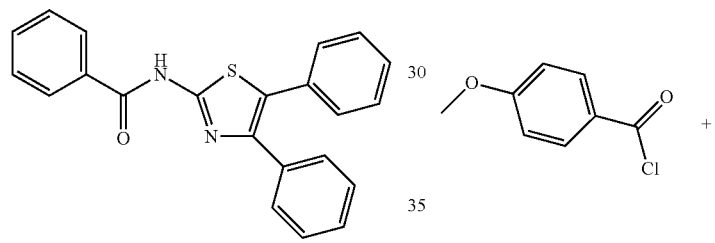

4,5-Diphenyl-thiazol-2-ylamine (50.5 mg, 0.200 mmol) and 4-methoxy-benzoyl chloride (34.1 mg, 0.200 mmol) were dissolved in 1,4-dioxane (2 mL) containing triethylamine (84.1 µL, 0.600 mmol). The reaction mixture was stirred overnight at room temperature. The crude product was filtered, evaporated to dryness, dissolved in 1 mL of dimethylsulfoxide and purified by reverse-phase preparative liquid chromatography (12.5 mg, 0.0323 mmol, 16.2%). ESI-MS m/z calc. 386.1, found 387.2 (M+1)+ Retention time 3.95 minutes.

40) 4-Methyl-N-(4-p-tolyl-thiazol-2-yl)-benzamide

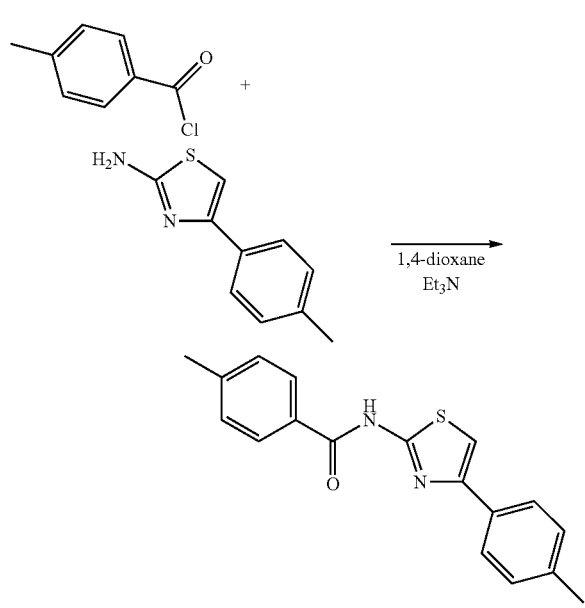

4-p-Tolyl-thiazol-2-ylamine (38.1 mg, 0.200 mmol) and 4-methyl-benzoyl chloride (30.5 mg, 0.200 mmol) were dissolved in 1,4-dioxane (2 mL) containing triethylamine (84.1 μL, 0.600 mmol). The reaction mixture was stirred overnight at room temperature. The crude product was filtered, evaporated to dryness, dissolved in 1 mL of dimethylsulfoxide and purified by reverse-phase preparative liquid chromatography (13.5 mg, 0.0438, 21.9%). ESI-MS m/z calc. 308.1, found 309.0 (M+1)+ Retention time 3.72 minutes.

41) 4-Methyl-N-(5-methyl-thiazol-2-yl)-benzamide

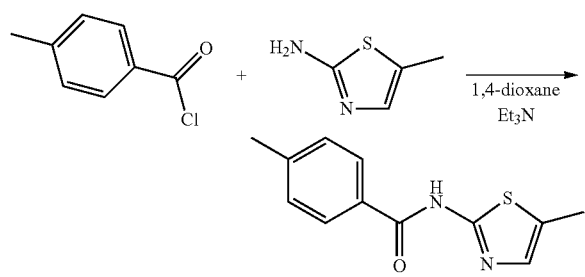

5-Methyl-thiazol-2-ylamine (22.8 mg, 0.200 mmol) and 4-methyl-benzoyl chloride (30.9 mg, 0.200 mmol) were dissolved in 1,4-dioxane (2 mL) containing triethylamine (84.1 μL, 0.600 mmol). The reaction mixture was stirred overnight at room temperature. The crude product was filtered, evaporated to dryness, dissolved in 1 mL of dimethylsulfoxide and purified by reverse-phase preparative liquid chromatography (9.29 mg, 0.400, 20.0%). ESI-MS m/z calc. 232.1, found 233.2 (M+1)+ Retention time 2.65 minutes.

42) N-[5-(2-Chloro-benzyl)-thiazol-2-yl]-2-methoxy-2-phenyl-acetamide

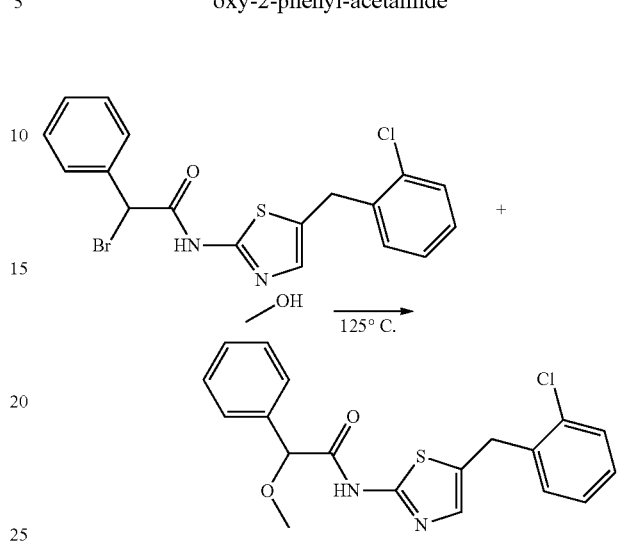

2-Bromo-N-[5-(2-chloro-benzyl)-thiazol-2-yl]-2-phenyl-acetamide (42 mg, 0.10 mmol) was dissolved in 5 mL of methanol. The reaction vessel was sealed and then subjected to microwave irradiation for 15 minutes at 125° C. The crude mixture was evaporated to dryness, dissolved in 1 mL of dimethylsulfoxide and purified by reverse-phase preparative liquid chromatography (16 mg, 0.043, 43%). ESI-MS m/z calc. 372.1, found 373.2 (M+1)+ Retention time 3.43 minutes. $^1$H NMR (400 MHz, CD$_3$CN) δ 3.42 (s, 3H), 4.23 (s, 2H), 4.94 (s, 1H), 7.21-7.53 (m, 10H)

43) N-[5-(2-Chloro-benzyl)-thiazol-2-yl]-2-methylamino-2-phenyl-acetamide

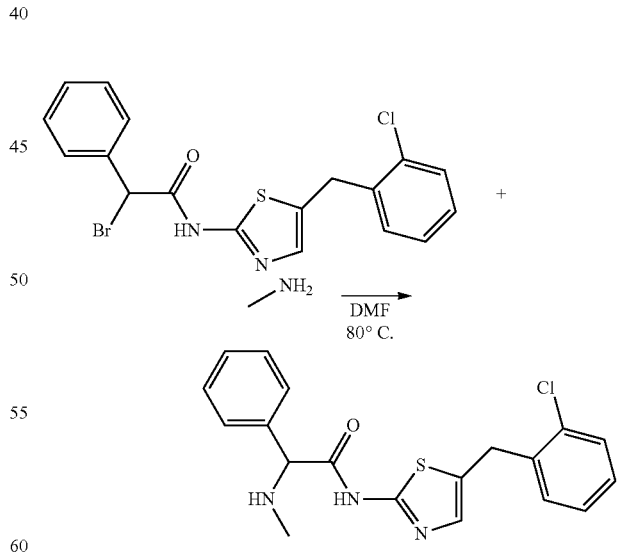

2-Bromo-N-[5-(2-chloro-benzyl)-thiazol-2-yl]-2-phenyl-acetamide (42 mg, 0.10 mmol) was dissolved in 0.5 mL of N,N-dimethylformamide containing 1.0 mL of methylamine (2.0 M in tetrahydrofuran, 2.0 mmol). The reaction vessel was sealed and then subjected to microwave irradiation for 5 minutes at 80° C. The crude mixture was evaporated to dryness, dissolved in 1 mL of dimethylsulfoxide and purified by reverse-phase preparative liquid chromatography (29 mg, 0.078, 78%). ESI-MS m/z calc. 371.1, found 372.2 (M+1)+ Retention time 2.33 minutes. $^1$H NMR (400 MHz, MeOD) δ 2.66 (s, 3H), 4.23 (s, 2H), 5.09 (s, 1H), 7.13-7.56 (m, 10H).

44) N-[5-(2-Chloro-benzyl)-thiazol-2-yl]-2-morpholin-4-yl-2-phenyl-acetamide

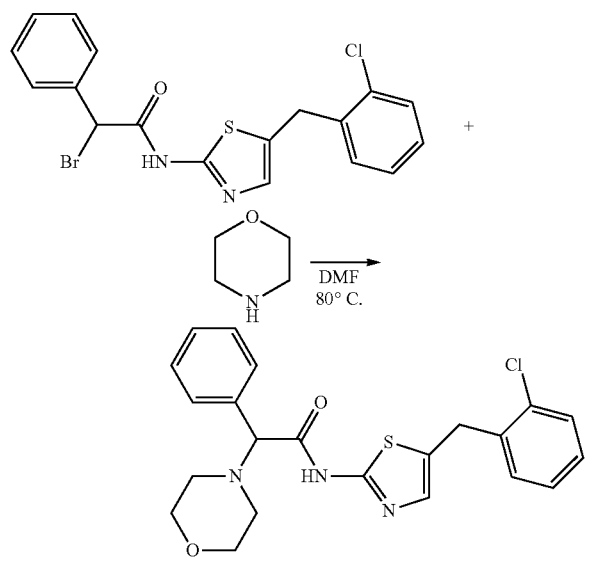

2-Bromo-N-[5-(2-chloro-benzyl)-thiazol-2-yl]-2-phenyl-acetamide (42 mg, 0.10 mmol) was dissolved in 0.5 mL of N,N-dimethylformamide containing morpholine (174 mg, 2.00 mmol). The reaction vessel was sealed and then subjected to microwave irradiation for 5 minutes at 80° C. The crude mixture was evaporated to dryness and purified by reverse-phase preparative liquid chromatography (31 mg, 0.072, 72%). ESI-MS m/z calc. 427.1, found 428.0 (M+1)+ Retention time 2.40 minutes.

45) N-[5-(2-Chloro-benzyl)-thiazol-2-yl]-2-dimethylamino-2-phenyl-acetamide

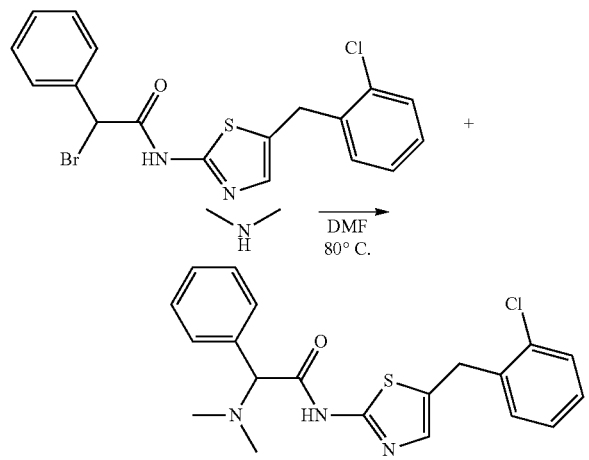

2-Bromo-N-[5-(2-chloro-benzyl)-thiazol-2-yl]-2-phenyl-acetamide (42 mg, 0.10 mmol) was dissolved in 0.5 mL of N,N-dimethylformamide containing dimethylamine (90.2 mg, 2.00 mmol). The reaction vessel was sealed and then subjected to microwave irradiation for 5 minutes at 80° C. The crude mixture was evaporated to dryness and purified by reverse-phase preparative liquid chromatography (13 mg, 0.034, 34%). ESI-MS m/z calc. 385.1, found 386.0 (M+1)+ Retention time 2.40 minutes.

46) N-[5-(2-Chloro-benzyl)-thiazol-2-yl]-2-dimethylamino-2-phenyl-acetamide

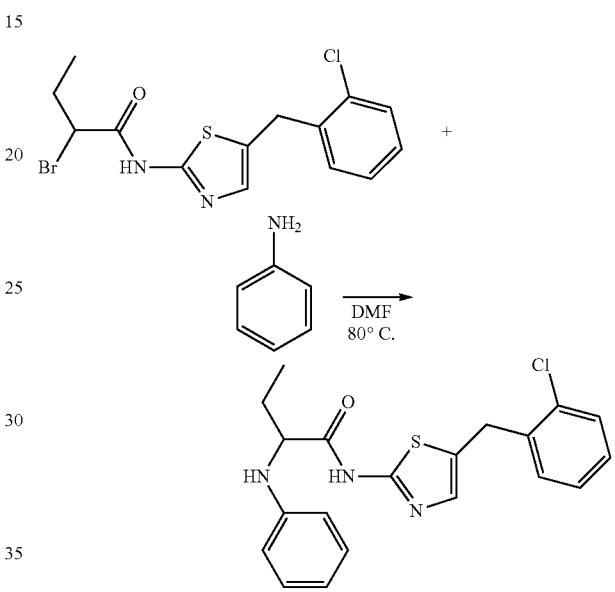

2-Bromo-N-[5-(2-chloro-benzyl)-thiazol-2-yl]-butyramide (37 mg, 0.10 mmol) was dissolved in 0.5 mL of N,N-dimethylformamide containing aniline (186 mg, 2.00 mmol). The reaction vessel was sealed and then subjected to microwave irradiation for 5 minutes at 80° C. The crude mixture was evaporated to dryness and purified by reverse-phase preparative liquid chromatography (24 mg, 0.062, 62%). ESI-MS m/z calc. 385.1, found 386.1 (M+1)+ Retention time 3.48 minutes.

47) N-[5-(2-Chloro-benzyl)-thiazol-2-yl]-2-ethylamino-butyramide

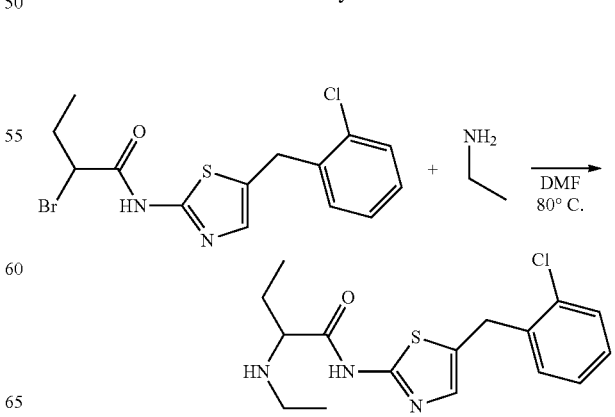

2-Bromo-N-[5-(2-chloro-benzyl)-thiazol-2-yl]-butyramide (37 mg, 0.10 mmol) was dissolved in 0.5 mL of N,N-dimethylformamide containing ethylamine (2 M in tetrahydrofuran, 1.00 mL, 2.00 mmol). The reaction vessel was sealed and then subjected to microwave irradiation for 5 minutes at 80° C. The crude mixture was evaporated to dryness and purified by reverse-phase preparative liquid chromatography (19 mg, 0.056, 56%). ESI-MS m/z calc. 337.1, found 338.0 (M+1)$^+$ Retention time 2.08 minutes.

48) N-[5-(2-Chloro-benzyl)-thiazol-2-yl]-2-piperidin-1-yl-butyramide

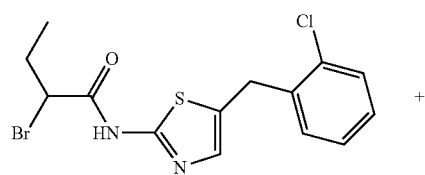

+

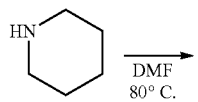

$\xrightarrow{\text{DMF}}_{\text{80° C.}}$

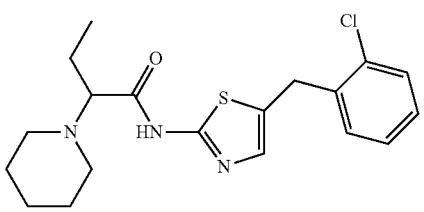

2-Bromo-N-[5-(2-chloro-benzyl)-thiazol-2-yl]-butyramide (37 mg, 0.10 mmol) was dissolved in 0.5 mL of N,N-dimethylformamide containing piperidine (170 mg, 2.0 mmol). The reaction vessel was sealed and then subjected to microwave irradiation for 5 minutes at 80° C. The crude mixture was evaporated to dryness and purified by reverse-phase preparative liquid chromatography (31 mg, 0.082, 82%). ESI-MS m/z calc. 377.1, found 378.2 (M+1)$^+$ Retention time 2.21 minutes.

49) N-[5-(2-Chloro-benzyl)-thiazol-2-yl]-2-diethylamino-butyramide

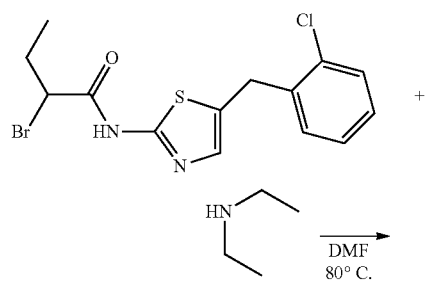

+

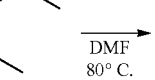

$\xrightarrow{\text{DMF}}_{\text{80° C.}}$

-continued

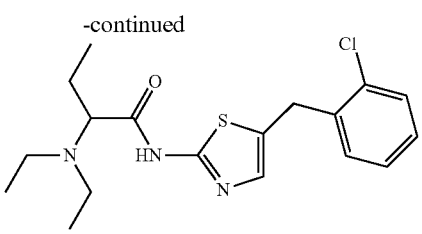

2-Bromo-N-[5-(2-chloro-benzyl)-thiazol-2-yl]-butyramide (37 mg, 0.10 mmol) was dissolved in 0.5 mL of N,N-dimethylformamide containing diethylamine (146 mg, 2.00 mmol). The reaction vessel was sealed and then subjected to microwave irradiation for 5 minutes at 80° C. The crude mixture was evaporated to dryness and purified by reverse-phase preparative liquid chromatography (14 mg, 0.038, 38%). ESI-MS m/z calc. 365.1, found 366.2 (M+1)$^+$ Retention time 2.18 minutes.

Analytical data for exemplary compounds of the present invention is recited below in Table 2 below.

TABLE 2

| Cmpd # | LC/MS | LC/RT |
|---|---|---|
| 2 | 309.00 | 3.00 |
| 4 | 325.00 | 3.63 |
| 5 | 325.20 | 3.53 |
| 6 | 341.00 | 3.42 |
| 7 | 341.00 | 3.47 |
| 18 | 281.20 | 3.20 |
| 21 | 280.80 | 3.35 |
| 23 | 329.00 | 3.38 |
| 24 | 310.90 | 3.58 |
| 25 | 385.20 | 3.67 |
| 28 | 329.00 | 3.37 |
| 29 | 335.00 | 3.50 |
| 31 | 343.20 | 3.33 |
| 32 | 309.00 | 3.13 |
| 34 | 374.00 | 1.83 |
| 35 | 338.00 | 1.27 |
| 37 | 419.20 | 3.92 |
| 38 | 419.20 | 3.85 |
| 39 | 385.30 | 4.24 |
| 47 | 309.00 | 3.72 |
| 48 | 295.20 | 2.83 |
| 49 | 311.00 | 3.41 |
| 50 | 309.20 | 2.01 |
| 51 | 387.40 | 2.96 |
| 52 | 371.20 | 4.13 |
| 53 | 315.00 | 3.63 |
| 55 | 287.00 | 3.53 |
| 58 | 324.20 | 2.05 |
| 66 | 247.00 | 2.73 |
| 67 | 295.20 | 3.52 |
| 68 | 357.20 | 3.95 |
| 69 | 311.00 | 3.43 |
| 70 | 371.20 | 4.11 |
| 71 | 371.20 | 3.94 |
| 72 | 387.20 | 3.95 |
| 73 | 425.20 | 4.41 |
| 74 | 391.20 | 4.18 |
| 75 | 295.00 | 3.45 |
| 76 | 311.00 | 3.52 |
| 77 | 314.80 | 3.38 |
| 78 | 311.20 | 3.37 |
| 79 | 341.00 | 3.53 |
| 80 | 340.80 | 3.49 |
| 81 | 311.20 | 3.35 |
| 82 | 341.00 | 3.42 |
| 83 | 325.00 | 3.53 |
| 84 | 340.80 | 3.38 |
| 85 | 247.00 | 3.03 |
| 86 | 261.00 | 3.27 |
| 87 | 261.00 | 3.30 |

TABLE 2-continued

| Cmpd # | LC/MS | LC/RT |
|---|---|---|
| 88 | 295.00 | 3.55 |
| 89 | 399.40 | 3.63 |
| 90 | 433.40 | 3.79 |
| 91 | 425.20 | 4.24 |
| 92 | 375.40 | 3.57 |
| 93 | 383.20 | 3.57 |
| 94 | 383.40 | 3.42 |
| 95 | 487.00 | 4.27 |
| 96 | 337.20 | 3.53 |
| 97 | 371.00 | 3.72 |
| 98 | 365.00 | 3.85 |
| 99 | 399.40 | 4.02 |
| 100 | 349.20 | 3.28 |
| 101 | 377.40 | 3.89 |
| 102 | 411.40 | 4.07 |
| 103 | 385.20 | 3.85 |
| 104 | 391.20 | 2.70 |
| 105 | 387.20 | 2.78 |
| 106 | 391.20 | 3.03 |
| 107 | 371.20 | 2.55 |
| 108 | 323.20 | 2.30 |
| 109 | 323.20 | 2.33 |
| 110 | 337.20 | 2.58 |
| 111 | 321.20 | 1.98 |
| 112 | 337.00 | 3.27 |
| 113 | 349.20 | 3.33 |
| 114 | 363.20 | 3.57 |
| 115 | 351.00 | 2.88 |
| 116 | 351.00 | 2.51 |
| 117 | 425.20 | 4.25 |
| 118 | 489.00 | 4.32 |
| 119 | 357.20 | 3.53 |
| 120 | 371.20 | 3.72 |
| 121 | 399.40 | 4.02 |
| 122 | 411.40 | 4.09 |
| 123 | 385.20 | 3.87 |
| 124 | 419.20 | 3.84 |
| 125 | 487.20 | 4.27 |
| 126 | 355.20 | 3.43 |
| 127 | 357.20 | 3.52 |
| 128 | 371.00 | 3.70 |
| 129 | 399.20 | 4.00 |
| 130 | 411.20 | 4.09 |
| 131 | 433.40 | 3.75 |
| 132 | 421.20 | 4.05 |
| 133 | 413.40 | 3.57 |
| 134 | 483.20 | 4.10 |
| 135 | 353.00 | 3.32 |
| 136 | 367.20 | 3.50 |
| 137 | 395.20 | 3.84 |
| 138 | 381.20 | 3.67 |
| 139 | 391.20 | 4.09 |
| 140 | 429.40 | 3.62 |
| 141 | 279.00 | 2.66 |
| 142 | 409.40 | 3.76 |
| 143 | 403.40 | 3.42 |
| 144 | 417.20 | 3.58 |
| 145 | 339.00 | 3.02 |
| 146 | 355.00 | 3.22 |
| 147 | 383.40 | 3.52 |
| 148 | 395.00 | 3.57 |
| 149 | 327.40 | 2.91 |
| 150 | 313.20 | 2.91 |
| 151 | 409.40 | 3.72 |
| 152 | 339.00 | 3.00 |
| 153 | 341.00 | 3.03 |
| 154 | 355.00 | 3.20 |
| 155 | 383.20 | 3.52 |
| 156 | 395.00 | 3.57 |
| 157 | 327.40 | 2.90 |
| 158 | 313.00 | 2.90 |
| 159 | 315.00 | 2.81 |
| 160 | 315.00 | 2.96 |
| 161 | 306.20 | 2.48 |
| 162 | 341.00 | 2.65 |
| 163 | 350.20 | 2.53 |
| 164 | 325.20 | 2.51 |
| 165 | 391.20 | 3.68 |
| 166 | 309.20 | 2.80 |
| 167 | 323.20 | 3.05 |
| 168 | 337.20 | 3.22 |
| 169 | 363.20 | 3.53 |
| 170 | 351.20 | 3.43 |
| 171 | 339.00 | 2.68 |
| 172 | 385.20 | 3.45 |
| 173 | 399.20 | 3.70 |
| 174 | 413.40 | 3.87 |
| 175 | 439.40 | 4.15 |
| 176 | 427.40 | 4.05 |
| 177 | 453.40 | 4.30 |
| 178 | 415.20 | 3.40 |
| 179 | 405.40 | 3.55 |
| 180 | 399.20 | 3.27 |
| 181 | 335.40 | 2.83 |
| 182 | 337.00 | 2.86 |
| 183 | 351.20 | 3.03 |
| 184 | 379.40 | 3.37 |
| 185 | 309.20 | 2.73 |
| 186 | 409.40 | 3.70 |
| 187 | 471.20 | 3.85 |
| 188 | 339.20 | 2.96 |
| 189 | 341.20 | 3.02 |
| 190 | 355.20 | 3.18 |
| 191 | 383.20 | 3.50 |
| 192 | 395.00 | 3.55 |
| 193 | 369.20 | 3.32 |
| 194 | 327.40 | 2.86 |
| 195 | 313.20 | 2.85 |
| 196 | 563.40 | 2.65 |
| 197 | 567.20 | 3.03 |
| 198 | 547.40 | 2.83 |
| 199 | 537.40 | 2.51 |
| 200 | 396.20 | 3.38 |
| 201 | — | 3.83 |
| 202 | — | 99.00 |
| 204 | 371.00 | 3.67 |
| 205 | — | 99.00 |
| 206 | 309.20 | 3.25 |
| 207 | 293.00 | 2.96 |
| 208 | 281.20 | 2.86 |
| 209 | 321.20 | 3.35 |
| 210 | 295.20 | 3.07 |
| 211 | 386.00 | 2.24 |
| 212 | 414.20 | 2.31 |
| 213 | 386.20 | 2.24 |
| 214 | 428.00 | 2.40 |
| 215 | 426.00 | 2.33 |
| 216 | 373.20 | 3.48 |
| 217 | 372.20 | 2.33 |
| 218 | 324.40 | 2.03 |
| 219 | 325.20 | 3.15 |
| 220 | 338.00 | 2.08 |
| 221 | 366.20 | 2.18 |
| 222 | 338.00 | 2.03 |
| 223 | 380.00 | 2.11 |
| 224 | 396.00 | 2.33 |
| 225 | 378.20 | 2.21 |
| 226 | 295.40 | 3.40 |
| 227 | 345.00 | 3.62 |
| 228 | 329.00 | 3.70 |
| 229 | 349.00 | 3.79 |
| 230 | 329.00 | 3.65 |
| 231 | 325.20 | 3.48 |
| 232 | 344.80 | 3.60 |
| 233 | 315.00 | 2.91 |
| 234 | 387.20 | 3.64 |
| 235 | 409.40 | 3.44 |
| 236 | 383.20 | 5.11 |
| 237 | 366.70 | 3.48 |
| 238 | 370.90 | 3.67 |
| 239 | 400.30 | 2.46 |
| 240 | 454.30 | 2.70 |
| 241 | 412.30 | 2.48 |
| 242 | 426.10 | 2.55 |
| 243 | 440.10 | 2.61 |
| 244 | 456.30 | 2.41 |

TABLE 2-continued

| Cmpd # | LC/MS | LC/RT |
| --- | --- | --- |
| 245 | 498.30 | 2.76 |
| 246 | 440.10 | 2.63 |
| 247 | 498.10 | 2.70 |
| 248 | 442.30 | 2.45 |
| 249 | 505.30 | 2.78 |
| 250 | 426.30 | 2.63 |
| 251 | 386.10 | 3.48 |
| 252 | 387.10 | 3.62 |
| 253 | 498.30 | 3.66 |
| 254 | 462.00 | 3.02 |
| 255 | 371.90 | 3.48 |
| 256 | 416.30 | 4.54 |
| 257 | 348.10 | 4.14 |
| 258 | 362.10 | 4.22 |
| 259 | 390.30 | 4.42 |
| 260 | 402.50 | 4.44 |
| 261 | 376.30 | 4.32 |
| 262 | 385.00 | 3.80 |
| 263 | 387.00 | 3.83 |
| 264 | 375.10 | 3.07 |
| 265 | 340.90 | 3.55 |
| 266 | 327.30 | 3.38 |
| 267 | 325.10 | 3.70 |
| 268 | 311.10 | 3.67 |
| 269 | 415.30 | 3.38 |
| 270 | 401.30 | 3.10 |
| 271 | 371.10 | 3.00 |
| 272 | 400.10 | 1.62 |
| 273 | 397.30 | 2.93 |
| 274 | 367.10 | 2.85 |
| 275 | 396.10 | 1.41 |
| 276 | 362.10 | 2.56 |
| 277 | 391.10 | 0.71 |
| 278 | 368.10 | 2.42 |
| 279 | 309.10 | 3.14 |
| 280 | 367.10 | 3.34 |
| 281 | 381.30 | 3.28 |
| 282 | 416.50 | 3.41 |
| 283 | 368.10 | 3.24 |
| 284 | 367.00 | 3.51 |
| 285 | 385.00 | 3.60 |
| 286 | 367.00 | 3.49 |
| 287 | 409.30 | 3.93 |
| 288 | 361.10 | 3.84 |
| 289 | 315.30 | 2.90 |

EXAMPLE 6

Assays for Detecting and Measuring ΔF508-CFTR Correction and Potentiator Properties of Compounds A) Membrane Potential Optical Methods for Assaying ΔF508-CFTR Modulation Properties of Compounds The optical membrane potential assay utilized voltage-sensitive FRET sensors described by Gonzalez and Tsien (See, Gonzales, J. E. and R. Y. Tsien (1995) "Voltage sensing by fluorescence resonance energy transfer in single cells" *Biophys J* 69 (4): 1272-80, and Gonzalez, J. E. and R. Y. Tsien (1997) "Improved indicators of cell membrane potential that use fluorescence resonance energy transfer" *Chem Biol* 4 (4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4 (9): 431-439).

These voltage sensitive assays are based on the change in fluorescence resonant energy transfer (FRET) between the membrane-soluble, voltage-sensitive dye, $DiSBAC_2$ (3), and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 mM forskolin and the CFTR potentiator, genistein (20 mM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 □M forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

$DiSBAC_2(3)$: Prepared as a 10 mM stock in DMSO and stored at −20° C.

Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours.

B) Electrophysiological Assays for Assaying ΔF508-CFTR Modulation Properties of Compounds 1. Ussing Chamber Assay Ussing chamber experiments were performed on polarized epithelial cells expressing ΔF508-CFTR to further characterize the ΔF508-CFTR modulators identified in the optical assays. $FRT^{\Delta 508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 mM) and the PDE inhibitor, IBMX (100 mM), were applied followed by the addition of the CFTR potentiator, genistein (50 mM).

As observed in other cell types, incubation at low temperatures of FRT cells stably expressing ΔF508-CFTR increases the functional density of CFTR in the plasma membrane. To determine the activity of correction compounds, the cells were incubated with 10 mM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 µg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 mM) and all test compounds were added to both sides of the cell culture inserts. The efficacy of the putative ΔF508-CFTR potentiators was compared to that of the known potentiator, genistein.

Solutions

Basolateral solution (in mM): NaCl (135), CaCl₂ (1.2), MgCl₂ (1.2), K₂HPO₄ (2.4), KHPO₄ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% CO₂ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-cell Recordings

The macroscopic ΔF508-CFTR current ($I_{\Delta F508}$) in temperature and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 ml of saline and was continuously perifused at a rate of 2 ml/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 mM forskolin and 20 mM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 □M of the test compound for 24 hours at 37° C. and the current density was compared to the 27° C. and 37° C. controls (% activity). Prior to recording, the cells were washed 3× with extracellular recording medium to remove any remaining test compound. Preincubation with 10 ΔM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Box F508}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), MgCl₂ (1), HEPES (10), and 240 µg/ml amphotericin-B (pH adjusted to 7.35 with CsOH).

Extracellular solution (in mM): N-methyl-D-glucamine (NMDG)-Cl (150), MgCl₂ (2), CaCl₂ (2), HEPES (10) (pH adjusted to 7.35 with HCl).

Cell Culture

NIH3T3 mouse fibroblasts stably expressing ΔF508-CFTR are used for whole-cell recordings. The cells are maintained at 37° C. in 5% CO₂ and 90% humidity in Dulbecco's modified Eagle's medium supplemented with 2 mM glutamine, 10% fetal bovine serum, 1× NEAA, □-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp, Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Solutions

Extracellular solution (in mM): NMDG (150), aspartic acid (150), CaCl₂ (5), MgCl₂ (2), and HEPES (10) (pH adjusted to 7.35 with Tris base).

Intracellular solution (in mM): NMDG-Cl (150), MgCl₂ (2), EGTA (5), TES (10), and Tris base (14) (pH adjusted, to 7.35 with HCl).

Cell Culture

NIH3T3 mouse fibroblasts stably expressing ΔF508-CFTR are used for excised-membrane patch-clamp recordings. The cells are maintained at 37° C. in 5% CO₂ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

The compounds of the present invention were found to modulate CFTR activity when tested using the above methods. The activity of exemplary compounds of the present invention is recited below in Table 3.

EC50: "+++" means <10 uM; "++" means between 10 uM to 25 uM; "+" means between 25 uM to 60 uM.

% Efficacy: "+" means <25%; "++" means between 25% to 100%; "+++" means >100%.

TABLE 3

| Cmpd # | EC50 uM | % Activity |
|---|---|---|
| 1 | ++ | ++ |
| 2 | +++ | +++ |
| 3 | ++ | ++ |
| 4 | +++ | ++ |
| 5 | ++ | ++ |
| 6 | ++ | ++ |
| 7 | ++ | +++ |
| 8 | +++ | +++ |
| 9 | +++ | ++ |
| 10 | ++ | +++ |
| 11 | ++ | +++ |
| 12 | +++ | +++ |
| 13 | +++ | ++ |
| 14 | +++ | ++ |
| 15 | +++ | ++ |
| 16 | +++ | +++ |
| 17 | +++ | ++ |
| 18 | ++ | ++ |
| 19 | ++ | ++ |
| 20 | ++ | ++ |
| 21 | ++ | ++ |
| 22 | ++ | ++ |
| 23 | +++ | ++ |
| 24 | ++ | +++ |
| 25 | +++ | ++ |
| 26 | ++ | ++ |
| 27 | +++ | ++ |
| 28 | ++ | ++ |
| 29 | +++ | ++ |
| 30 | +++ | +++ |
| 31 | +++ | ++ |
| 32 | ++ | ++ |
| 33 | ++ | ++ |
| 34 | ++ | ++ |
| 35 | ++ | ++ |
| 36 | ++ | ++ |
| 37 | +++ | +++ |
| 38 | +++ | ++ |
| 39 | +++ | +++ |
| 40 | +++ | ++ |
| 41 | +++ | ++ |
| 42 | +++ | ++ |
| 43 | +++ | ++ |
| 44 | ++ | +++ |
| 45 | ++ | ++ |
| 46 | +++ | ++ |
| 47 | ++ | ++ |
| 48 | +++ | +++ |
| 49 | ++ | ++ |
| 50 | +++ | +++ |
| 51 | +++ | +++ |
| 52 | +++ | +++ |
| 53 | +++ | +++ |
| 54 | ++ | ++ |
| 55 | ++ | ++ |
| 56 | +++ | ++ |
| 57 | +++ | ++ |
| 58 | ++ | ++ |
| 59 | ++ | ++ |
| 60 | ++ | ++ |
| 61 | ++ | ++ |
| 62 | +++ | +++ |
| 63 | ++ | +++ |
| 64 | +++ | +++ |
| 65 | ++ | ++ |
| 66 | ++ | ++ |
| 67 | ++ | ++ |
| 68 | +++ | ++ |
| 69 | ++ | +++ |
| 70 | +++ | +++ |
| 71 | +++ | ++ |
| 72 | +++ | +++ |
| 73 | ++ | ++ |

TABLE 3-continued

| Cmpd # | EC50 uM | % Activity |
|---|---|---|
| 74 | ++ | ++ |
| 75 | ++ | ++ |
| 76 | ++ | +++ |
| 77 | ++ | ++ |
| 78 | ++ | ++ |
| 79 | ++ | ++ |
| 80 | ++ | ++ |
| 81 | ++ | ++ |
| 82 | ++ | ++ |
| 83 | ++ | +++ |
| 84 | ++ | ++ |
| 85 | ++ | ++ |
| 86 | ++ | ++ |
| 87 | ++ | ++ |
| 88 | ++ | +++ |
| 89 | +++ | +++ |
| 90 | +++ | +++ |
| 91 | +++ | +++ |
| 92 | +++ | ++ |
| 93 | +++ | +++ |
| 94 | +++ | ++ |
| 95 | +++ | ++ |
| 96 | ++ | ++ |
| 97 | +++ | +++ |
| 98 | +++ | ++ |
| 99 | +++ | +++ |
| 100 | ++ | ++ |
| 101 | +++ | ++ |
| 102 | +++ | +++ |
| 103 | +++ | +++ |
| 104 | +++ | ++ |
| 105 | +++ | +++ |
| 106 | +++ | ++ |
| 107 | +++ | +++ |
| 108 | +++ | ++ |
| 109 | +++ | ++ |
| 110 | +++ | +++ |
| 111 | +++ | +++ |
| 112 | +++ | ++ |
| 113 | +++ | ++ |
| 114 | +++ | ++ |
| 115 | +++ | +++ |
| 116 | +++ | ++ |
| 117 | +++ | +++ |
| 118 | +++ | ++ |
| 119 | +++ | +++ |
| 120 | +++ | ++ |
| 121 | +++ | +++ |
| 122 | +++ | +++ |
| 123 | +++ | +++ |
| 124 | +++ | ++ |
| 125 | +++ | ++ |
| 126 | + | ++ |
| 127 | +++ | ++ |
| 128 | +++ | +++ |
| 129 | +++ | ++ |
| 130 | +++ | +++ |
| 131 | +++ | +++ |
| 132 | +++ | ++ |
| 133 | +++ | ++ |
| 134 | +++ | ++ |
| 135 | +++ | ++ |
| 136 | +++ | ++ |
| 137 | +++ | ++ |
| 138 | +++ | ++ |
| 139 | +++ | ++ |
| 140 | +++ | ++ |
| 141 | ++ | ++ |
| 142 | +++ | ++ |
| 143 | + | ++ |
| 144 | + | ++ |
| 145 | ++ | ++ |
| 146 | +++ | ++ |
| 147 | +++ | ++ |
| 148 | +++ | ++ |
| 149 | ++ | ++ |
| 150 | ++ | ++ |
| 151 | +++ | ++ |
| 152 | ++ | ++ |
| 153 | +++ | ++ |
| 154 | +++ | ++ |
| 155 | +++ | ++ |
| 156 | +++ | ++ |
| 157 | +++ | ++ |
| 158 | +++4 | ++ |
| 159 | +++ | ++ |
| 160 | ++ | +++ |
| 161 | + | ++ |
| 162 | + | ++ |
| 163 | ++ | ++ |
| 164 | ++ | ++ |
| 165 | +++ | +++ |
| 166 | ++ | ++ |
| 167 | +++ | ++ |
| 168 | +++ | ++ |
| 169 | +++ | ++ |
| 170 | +++ | ++ |
| 171 | +++ | ++ |
| 172 | +++ | +++ |
| 173 | +++ | ++ |
| 174 | +++ | ++ |
| 175 | +++ | ++ |
| 176 | +++ | ++ |
| 177 | ++ | ++ |
| 178 | +++ | +++ |
| 179 | ++ | ++ |
| 180 | ++ | ++ |
| 181 | + | ++ |
| 182 | + | ++ |
| 183 | + | ++ |
| 184 | ++ | ++ |
| 185 | ++ | ++ |
| 186 | ++ | ++ |
| 187 | ++ | ++ |
| 188 | + | ++ |
| 189 | + | ++ |
| 190 | + | ++ |
| 191 | +++ | ++ |
| 192 | ++ | ++ |
| 193 | ++ | ++ |
| 194 | + | ++ |
| 195 | +++ | ++ |
| 196 | +++ | ++ |
| 197 | +++ | ++ |
| 198 | +++ | ++ |
| 199 | +++ | +++ |
| 200 | + | ++ |
| 201 | +++ | +++ |
| 202 | +++ | ++ |
| 203 | +++ | ++ |
| 204 | +++ | ++ |
| 205 | +++ | ++ |
| 206 | +++ | ++ |
| 207 | +++ | ++ |
| 208 | + | ++ |
| 209 | +++ | ++ |
| 210 | ++ | ++ |
| 211 | +++ | ++ |
| 212 | +++ | ++ |
| 213 | ++ | ++ |
| 214 | ++ | ++ |
| 215 | +++ | ++ |
| 216 | ++ | ++ |
| 217 | + | ++ |
| 218 | + | ++ |
| 219 | + | ++ |
| 220 | + | ++ |
| 221 | ++ | ++ |
| 222 | + | ++ |
| 223 | + | ++ |
| 224 | +++ | ++ |
| 225 | +++ | ++ |
| 226 | ++ | ++ |
| 227 | ++ | ++ |

TABLE 3-continued

| Cmpd # | EC50 uM | % Activity |
|---|---|---|
| 228 | ++ | ++ |
| 229 | ++ | ++ |
| 230 | +++ | +++ |
| 231 | ++ | +++ |
| 232 | ++ | ++ |
| 233 | + | ++ |
| 234 | ++ | ++ |
| 235 | +++ | ++ |
| 236 | +++ | ++ |
| 237 | +++ | +++ |
| 238 | +++ | +++ |
| 239 | +++ | ++ |
| 240 | +++ | ++ |
| 241 | +++ | ++ |
| 242 | +++ | +++ |
| 243 | +++ | +++ |
| 244 | +++ | ++ |
| 245 | +++ | ++ |
| 246 | +++ | ++ |
| 247 | +++ | +++ |
| 248 | +++ | ++ |
| 249 | +++ | ++ |
| 250 | +++ | ++ |
| 251 | +++ | ++ |
| 252 | ++ | ++ |
| 253 | + | ++ |
| 254 | +++ | ++ |
| 255 | +++ | ++ |
| 256 | +++ | ++ |
| 257 | + | ++ |
| 258 | ++ | ++ |
| 259 | +++ | ++ |
| 260 | +++ | ++ |
| 261 | +++ | ++ |
| 262 | + | ++ |
| 263 | +++ | ++ |
| 264 | + | ++ |
| 265 | +++ | +++ |
| 266 | +++ | ++ |
| 267 | +++ | ++ |
| 268 | +++ | ++ |
| 269 | +++ | ++ |
| 270 | +++ | ++ |
| 271 | +++ | ++ |
| 272 | +++ | +++ |
| 273 | +++ | ++ |
| 274 | + | ++ |
| 275 | + | ++ |
| 276 | + | ++ |
| 277 | + | ++ |
| 278 | +++ | ++ |
| 279 | + | ++ |
| 280 | +++ | ++ |
| 281 | ++ | ++ |
| 282 | +++ | ++ |
| 283 | +++ | ++ |
| 284 | +++ | ++ |
| 285 | +++ | ++ |
| 286 | +++ | ++ |
| 287 | +++ | ++ |
| 288 | +++ | ++ |
| 289 | + | ++ |

The invention claimed is:

1. A pharmaceutical composition comprising a compound of formula (II) or (III):

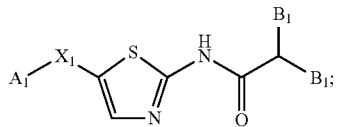

(II)

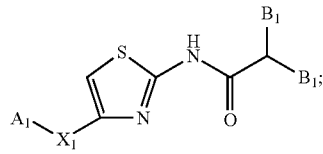

(III)

or a pharmaceutically acceptable salt thereof;

wherein:

$X_1$ is a bond, O, S, $CF_2$, $CH_2$, or NR;

R is H or $R^2$ $A_1$ is aryl or heteroaryl;

each $B_1$ is independently selected from 3-7 membered monocyclic, saturated, unsaturated or aromatic ring containing 0-4 heteroatoms selected from N, NH, S, or O;

wherein each $A_1$ is optionally substituted with up to 4 substituents independently selected from $R^1$, $R^3$, $R^4$, or $R^5$;

$R^1$ is ((C1-C4)aliphatic)$_n$-Y;

n is 0 or 1;

Y is halo, CN, $CF_3$, $OCF_3$, OH, $S(O)R^6$, $SO_2R^6$, $NH_2$, $NHR^6$, $N(R^6)_2$, COOH, $COOR^6$ or $OR^6$; or two $R^1$ on adjacent ring atoms, taken together, form 1,2-methylenedioxy or 1,2-ethylenedioxy;

$R^2$ is aliphatic, wherein each $R^2$ is optionally substituted with up to 2 substituents independently selected from $R^1$, $R^4$, or $R^5$;

$R^3$ is a cycloaliphatic, aryl, heterocyclic, or heteroaryl ring optionally substituted with up to 3 substituents, independently selected from $R^1$, $R^2$, $R^4$ or $R^5$;

$R^4$ is $OR^5$, $C(O)R^5$, $C(O)OR^5$, $C(O)R^6$, $C(O)OR^6$, $C(O)N(R^6)_2$, $C(O)N(R^5)_2$, or $C(O)N(R^5R^6)$;

$R^5$ is a cycloaliphatic, aryl, heterocyclic, or heteroaryl ring, optionally substituted with up to 3 $R^1$ substituents; and $R^6$ is H or aliphatic;

provided that for compounds of formula (II):

(i) when both $B_1$ are simultaneously phenyl and $X_1$ is $CH_2$, then $A_1$ is not 4-fluorophenyl, 4-phenyl-piperidyl, phenyl, 2,4-dichloro-phenyl, 4-methoxy-phenyl, 3,4-dichloro-phenyl, 2,5-dichloro-phenyl, 4-nitro-phenyl, 4-bromo-phenyl, 4-methyl-phenyl, 2-chloro-phenyl, 1-naphthyl, 3-trifluoromethyl-phenyl, 2,3-dichlorophenyl, N-morpholinyl, 4-chlorophenyl, 3-chloro-phenyl, or 3-nitro-phenyl;

(ii) when $X_1$ is a bond or $CH_2$, one $B_1$ is a substituted phenyl and the other $B_1$ is cycloaliphatic, then $A_1$ is not (C2-C8)aliphatic; and (iii) when $X_1$ is a bond, then $A_1$ is not an optionally substituted 6-membered heteroaryl ring with 1-3 nitrogen ring atoms; and provided that for compounds of formula (III):

(i) when $X_1$ is a bond, one $B_1$ is phenyl and the other $B_1$ is N-piperidyl, then $A_1$ is not:

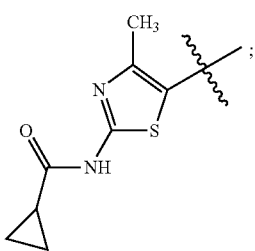 [SMILES: *c1sc(NC(=O)C2CC2)nc1C]

and (ii) when $X_1$ is a bond, then $A_1$ is not an optionally substituted 6-membered heteroaryl ring with 1-3 nitrogen ring atoms, and a pharmaceutically acceptable carrier.

2. The pharmaceutical composition according to claim 1, wherein $X_1$ is $CH_2$, $CF_2$, or O.

3. The pharmaceutical composition according to claim 1, wherein $X_1$ is $CH_2$.

4. The pharmaceutical composition according to claim 1, wherein $A_1$ is selected from phenyl, triazinyl, pyrazinyl, pyrimidinyl, pyridazinyl, pyridyl, pyrazolyl, quinolinyl, isoquinolinyl, or naphthyl.

5. The pharmaceutical composition according to claim 1, wherein each $B_1$ is independently selected from optionally substituted C6-C10 aryl.

6. The pharmaceutical composition according to claim 1, wherein each $B_1$ is independently an optionally substituted phenyl or naphthyl.

7. The pharmaceutical composition according to claim 1, wherein each $B_1$ is an unsubstituted phenyl.

8. The pharmaceutical composition according to claim 1, wherein each $B_1$ is independently selected from optionally substituted C5-C12 heteroaryl.

9. The pharmaceutical composition according to claim 1, wherein each $B_1$ is independently selected from optionally substituted C5-C7 heteroaryl.

10. The pharmaceutical composition according to claim 9, wherein each $B_1$ is independently selected from optionally substituted pyrazolyl or imidazolyl.

11. The pharmaceutical composition according to claim 1, wherein $B_1$ is selected from optionally substituted pyrrolinyl, pyrazolinyl, piperidinyl, morpholinyl, or piperazinyl.

12. The pharmaceutical composition according to claim 1, wherein $A_1$ is optionally substituted C6-C10 aryl ring.

13. The pharmaceutical composition according to claim 12, wherein $A_1$ is optionally substituted phenyl or naphthyl.

14. The pharmaceutical composition according to claim 1, wherein $A_1$ is optionally substituted C5-C12 heteroaryl ring.

15. The pharmaceutical composition according to claim 14, wherein $A_1$ is pyridinyl.

16. The pharmaceutical composition according to claim 1, wherein each $B_1$ is independently an optionally substituted 3-12 membered heterocyclic ring having up to 4 heteroatoms selected from O, S, or NR.

17. The pharmaceutical composition according to claim 16, wherein each $B_1$ is independently selected from optionally substituted pyrrolidyl, pyrrolinyl, pyranyl, piperidinyl, or morpholinyl.

* * * * *